US010633437B2

(12) United States Patent
Akita et al.

(10) Patent No.: US 10,633,437 B2
(45) Date of Patent: Apr. 28, 2020

(54) TREATMENT OF MYOCARDIAL INFARCTION USING TGF-β ANTAGONISTS

(71) Applicant: Genzyme Corporation, Cambridge, MA (US)

(72) Inventors: Geoffrey Y. Akita, Northborough, MA (US); Scott Lonning, Northbridge, MA (US); Richard C Gregory, Jr., Framingham, MA (US); Amelia B Kudej, Westborough, MA (US)

(73) Assignee: GENZYME CORPORATION, Cambridge, MA (US)

( * ) Notice: Subject to any disclaimer, the term of this patent is extended or adjusted under 35 U.S.C. 154(b) by 89 days.

(21) Appl. No.: 15/376,358

(22) Filed: Dec. 12, 2016

(65) Prior Publication Data

US 2017/0233465 A1    Aug. 17, 2017

Related U.S. Application Data

(63) Continuation of application No. 15/145,062, filed on May 3, 2016, now abandoned, which is a continuation of application No. 13/819,393, filed as application No. PCT/US2011/001536 on Sep. 1, 2011, now abandoned.

(60) Provisional application No. 61/379,315, filed on Sep. 1, 2010.

(51) Int. Cl.
| | |
|---|---|
| *A61P 9/10* | (2006.01) |
| *A61K 39/395* | (2006.01) |
| *G01N 33/50* | (2006.01) |
| *C07K 16/22* | (2006.01) |
| *A61K 45/06* | (2006.01) |
| *A61K 39/00* | (2006.01) |

(52) U.S. Cl.
CPC .......... *C07K 16/22* (2013.01); *A61K 39/3955* (2013.01); *A61K 45/06* (2013.01); *A61K 2039/505* (2013.01); *A61K 2039/545* (2013.01); *C07K 2317/21* (2013.01); *C07K 2317/56* (2013.01); *C07K 2317/76* (2013.01)

(58) Field of Classification Search
None
See application file for complete search history.

(56) References Cited

U.S. PATENT DOCUMENTS

| 7,723,486 B2 | 5/2010 | Ledbetter |
| 2010/0190731 A1 | 7/2010 | Olgin |

FOREIGN PATENT DOCUMENTS

| WO | 2005097832 A1 | 10/2005 |
| WO | WO 2006/037029 | 4/2006 |
| WO | 2006/083779 | 8/2006 |
| WO | WO 2006/086469 | 8/2006 |

OTHER PUBLICATIONS

Bujak et al, 2007. Cardivasc Res. 74(2): 184-195. (Year: 2007).*
Takeshita et al, 2004. American Journal of Pathology. 164(2): 449-456.*
Okamoto, 2006 (Mol Cell Biochem. 300:1-7).*
Lambert et al (2008. Int J Cardiol. 12: 130(2): 147-158; 24 pages as printed). (Year: 2008).*
Krijnen et al (2002. J Clin Pathol. 55: 801-811). (Year: 2002).*
Ellmers et al., *Transforming Growth Factor-β Blockade Down-Regulates the Renin-Angiotensin System and Modifies Cardiac Remodeling after Myocardial Infarction*, 149(11) Endocrinology 5828-5834 (2008).
Frantz et al., *Transforming growth factor beta inhibition increases mortality and left ventricular dilatation after myocardial infarction*, 103 Basic Res Cardiol 485-492 (2008).
Ikeuchi et al., *Inhibition of TGF-β signaling exacerbates early cardiac dysfunction but prevents late remodeling after infarction*, 64 Cardiovascular Research 526-535 (2004).
Okada et al., *Postinfarction Gene Therapy Against Transforming Growth Factor-β Signal Modulates Infarct Tissue Dynamics and Attenuates Left Ventricular Remodeling and Heart Failure*, 111(19) Circulation 2430-2437 (2008).
"Fresolimumab". IUPHAR/BPS Guide to Pharmacology. 1 page as printed. No date indicated, printed on Sep. 21, 2015. Available at http://www.guidetopharmacology.org/GRAC/LigandDisplayForward?ligandId=8264.
Wells (1990) Biochemistry 29(37): 8509-8517.
Ngo et al (1994) "The Protein Folding Problem and Tertiary Structure Prediction, Chapter 14: Computational Complexity Protein Structure Prediction, and the Levinthal Paradox" pp. 433-440 and 492-495 only.
Bork (2000) Genome Research 10:398.
Skolnick et al (2000) Trends in Biotech. 18(1 ): 34.
Doerks et al (1998) Trends in Genetics 14(6): 248.
Brenner (1999) Trends in Genetics 15(4): 132.
Vidal et al. 2005. European Journal of Cancer. 41: 2812-2818.
Pirollo et al, 2008. Cancer Res. 68(5): 1247-1250.
Bramlage et al, Aug. 2009. Expert Opin Pharmacother. 1 0(11 ): 1817-1831.

* cited by examiner

*Primary Examiner* — Zachary C Howard
(74) *Attorney, Agent, or Firm* — Steptoe & Johnson LLP; Z. Ying Li; Mauricio Alvarez

(57) ABSTRACT

Disclosed herein is a method of treating a patient suffering a myocardial infarction, particularly an acute myocardial infarction, or of reducing an adverse consequence of a myocardial infarction in a patient comprising administering an antagonist of TGF-β to the patient during the acute stage of the myocardial infarction.

20 Claims, 17 Drawing Sheets

Specification includes a Sequence Listing.

SEQUENCE LISTING

```
<160> NUMBER OF SEQ ID NOS: 31

<210> SEQ ID NO 1
<211> LENGTH: 360
<212> TYPE: DNA
<213> ORGANISM: Artificial sequence
<220> FEATURE:
<223> OTHER INFORMATION: Synthetic Nucleotide sequence encoding
      PET1073G12 VH

<400> SEQUENCE: 1
caggtgcagc tggtgcagtc tggggctgag gtgaagaagc ctgggtcctc ggtgaaggtc      60
tcctgcaagg cttctggata caccttcagt agcaatgtta tcagctgggt gcgccaggcc     120
cctggacaag gctcgagtg gatgggggg gtcatcccta ttgttgatat tgcgaactac      180
gcacagagat tcaagggcag agtcacgatt accgcggacg aatccactag tacaacttac     240
atggagttga gcagcctgag gtctgaggac acggccgtgt attactgtgc gagcacactt     300
ggtctcgtcc tggatgctat ggactactgg ggtcaggta cgttggtcac cgtctcctca     360

<210> SEQ ID NO 2
<211> LENGTH: 120
<212> TYPE: PRT
<213> ORGANISM: Artificial sequence
<220> FEATURE:
<223> OTHER INFORMATION: Synthetic Amino acid sequence of PET1073G12 VH

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Thr Leu Val Thr Val Ser Ser
        115                 120

<210> SEQ ID NO 3
<211> LENGTH: 5
<212> TYPE: PRT
<213> ORGANISM: Artificial sequence
<220> FEATURE:
<223> OTHER INFORMATION: Synthetic Amino acid sequence of PET1073G12
      HCDR1

<400> SEQUENCE: 3

Ser Asn Val Ile Ser
```

<210> SEQ ID NO 4
<211> LENGTH: 17
<212> TYPE: PRT
<213> ORGANISM: Artificial sequence
<220> FEATURE:
<223> OTHER INFORMATION: Synthetic Amino acid sequence of PET1073G12
      HCDR2

<400> SEQUENCE: 4

Gly Val Ile Pro Ile Val Asp Ile Ala Asn Tyr Ala Gln Arg Phe Lys
1               5                   10                  15
Gly

<210> SEQ ID NO 5
<211> LENGTH: 11
<212> TYPE: PRT
<213> ORGANISM: Artificial sequence
<220> FEATURE:
<223> OTHER INFORMATION: Synthetic Amino acid sequence of PET1073G12
      HCDR3

<400> SEQUENCE: 5

Thr Leu Gly Leu Val Leu Asp Ala Met Asp Tyr
1               5                   10

<210> SEQ ID NO 6
<211> LENGTH: 324
<212> TYPE: DNA
<213> ORGANISM: Artificial sequence
<220> FEATURE:
<223> OTHER INFORMATION: Synthetic Nucleotide sequence encoding
      PET1073G12 VL

<400> SEQUENCE: 6
gaaacggtac tcacgcagtc tccaggtacc ctgtctttgt ctccagggga aagagccacc        60
ctctcctgca gggccagtca gagtcttggc agcagctact tagcctggta tcagcagaaa       120
cctggtcagg ctcccaggct cctcatctat ggtgcatcca gcagggcacc tggcatccca       180
gacaggttca gtggcagtgg gtctggtacc gacttcactc tcaccatcag ccgactggag       240
cctgaagatt ttgcagttta ttactgtcag cagtatgctg actcaccgat caccttcggc       300
caagggacac gactggagat taaa                                              324

<210> SEQ ID NO 7
<211> LENGTH: 108
<212> TYPE: PRT
<213> ORGANISM: Artificial sequence
<220> FEATURE:
<223> OTHER INFORMATION: Synthetic Amino acid sequence of PET1073G12 VL

<400> SEQUENCE: 7

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Pro Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys
            100                 105

<210> SEQ ID NO 8
<211> LENGTH: 12
<212> TYPE: PRT
<213> ORGANISM: Artificial sequence
<220> FEATURE:
<223> OTHER INFORMATION: Synthetic Amino acid sequence of PET1073G12
      LCDR1

<400> SEQUENCE: 8

Arg Ala Ser Gln Ser Leu Gly Ser Ser Tyr Leu Ala
1               5                   10

<210> SEQ ID NO 9
<211> LENGTH: 7
<212> TYPE: PRT
<213> ORGANISM: Artificial sequence
<220> FEATURE:
<223> OTHER INFORMATION: Synthetic Amino acid sequence of PET1073G12
      LCDR2

<400> SEQUENCE: 9

Gly Ala Ser Ser Arg Ala Pro
1               5

<210> SEQ ID NO 10
<211> LENGTH: 9
<212> TYPE: PRT
<213> ORGANISM: Artificial sequence
<220> FEATURE:
<223> OTHER INFORMATION: Synthetic Amino acid sequence of PET1073G12
      LCDR3

<400> SEQUENCE: 10

Gln Gln Tyr Ala Asp Ser Pro Ile Thr
1               5

<210> SEQ ID NO 11
<211> LENGTH: 360
<212> TYPE: DNA
<213> ORGANISM: Artificial sequence
<220> FEATURE:
<223> OTHER INFORMATION: Synthetic Nucleotide sequence encoding
      PET1074B9 VH

<400> SEQUENCE: 11
caggtgcagc tggtgcagtc tggggctgag gtgaagaagc ctgggtcctc ggtgaaggtc      60
tcctgcaagg cttctggata caccttcagt agcaatgtta tcagctgggt gcgccaggcc    120
cctggacaag gctcgagtg gatggggggg gtcatcccta ttgttgatat tgcgaactac    180
gcacagagat tcaagggcag agtcacgatt accgcggacg aatccactag tacaacttac    240
atggagttga gcagcctgag gtctgaggac acggccgtgt attactgtgc gctgccacgc    300
gctttcgtcc tggatgctat ggactactgg ggtcagggta cgttggtgac cgtctcctca    360

<210> SEQ ID NO 12
<211> LENGTH: 120
<212> TYPE: PRT
<213> ORGANISM: Artificial sequence
<220> FEATURE:
<223> OTHER INFORMATION: Synthetic Amino acid sequence of PET1074B9 VH
```

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Leu Pro Arg Ala Phe Val Leu Asp Ala Met Asp Tyr Trp Gly Gln
            100                 105                 110

Gly Thr Leu Val Thr Val Ser Ser
        115                 120

<210> SEQ ID NO 13
<211> LENGTH: 5
<212> TYPE: PRT
<213> ORGANISM: Artificial sequence
<220> FEATURE:
<223> OTHER INFORMATION: Synthetic Amino acid sequence of PET1074B9
      HCDR1

<400> SEQUENCE: 13

Ser Asn Val Ile Ser
1               5

<210> SEQ ID NO 14
<211> LENGTH: 17
<212> TYPE: PRT
<213> ORGANISM: Artificial sequence
<220> FEATURE:
<223> OTHER INFORMATION: Synthetic Amino acid sequence of PET1074B9
      HCDR2

<400> SEQUENCE: 14

Gly Val Ile Pro Ile Val Asp Ile Ala Asn Tyr Ala Gln Arg Phe Lys
1               5                   10                  15

Gly

<210> SEQ ID NO 15
<211> LENGTH: 11
<212> TYPE: PRT
<213> ORGANISM: Artificial sequence
<220> FEATURE:
<223> OTHER INFORMATION: Synthetic Amino acid sequence of PET1074B9
      HCDR3

<400> SEQUENCE: 15

Pro Arg Ala Phe Val Leu Asp Ala Met Asp Tyr
1               5                   10

<210> SEQ ID NO 16
<211> LENGTH: 324
<212> TYPE: DNA
<213> ORGANISM: Artificial sequence
<220> FEATURE:
<223> OTHER INFORMATION: Synthetic Nucleotide sequence encoding
      PET1074B9 VL

<400> SEQUENCE: 16

```
gaaacggtac tcacgcagtc tccaggtacc ctgtctttgt ctccagggga aagagccacc    60
ctctcctgca gggccagtca gagtcttggc agcagctact tagcctggta tcagcagaaa   120
cctggtcagg ctcccaggct cctcatctat ggtgcatcca gcagggcacc tggcatccca   180
gacaggttca gtggcagtgg gtctggtacc gacttcactc tcaccatcag ccgactggag   240
cctgaagatt ttgcagttta ttactgtcag cagtatgctg actcaccgat caccttcggc   300
caagggacac gactggagat taaa                                          324
```

<210> SEQ ID NO 17
<211> LENGTH: 108
<212> TYPE: PRT
<213> ORGANISM: Artificial sequence
<220> FEATURE:
<223> OTHER INFORMATION: Synthetic Amino acid sequence of PET1074B9 VL

<400> SEQUENCE: 17

```
Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys
            100                 105
```

<210> SEQ ID NO 18
<211> LENGTH: 12
<212> TYPE: PRT
<213> ORGANISM: Artificial sequence
<220> FEATURE:
<223> OTHER INFORMATION: Synthetic Amino acid sequence of PET1074B9 LCDR1

<400> SEQUENCE: 18

```
Arg Ala Ser Gln Ser Leu Gly Ser Ser Tyr Leu Ala
1               5                   10
```

<210> SEQ ID NO 19
<211> LENGTH: 7
<212> TYPE: PRT
<213> ORGANISM: Artificial sequence
<220> FEATURE:
<223> OTHER INFORMATION: Synthetic Amino acid sequence of PET1074B9 LCDR2

<400> SEQUENCE: 19

```
Gly Ala Ser Ser Arg Ala Pro
1               5
```

<210> SEQ ID NO 20
<211> LENGTH: 9
<212> TYPE: PRT
<213> ORGANISM: Artificial sequence
<220> FEATURE:
<223> OTHER INFORMATION: Synthetic Amino acid sequence of PET1074B9
      LCDR3

<400> SEQUENCE: 20

Gln Gln Tyr Ala Asp Ser Pro Ile Thr
1               5

<210> SEQ ID NO 21
<211> LENGTH: 363
<212> TYPE: DNA
<213> ORGANISM: Artificial sequence
<220> FEATURE:
<223> OTHER INFORMATION: Synthetic Nucleotide sequence encoding
      PET1287A10 VH

<400> SEQUENCE: 21
caggtgcagc tggtgcagtc tggggctgag gtgaagaagc ctgggtcctc ggtgaaagtg        60
tcctgcaagg cttctggagg caccttcagc acctctttca tcaattgggt gcgacaggcc       120
cctggacaag gcttgagtg gatgggaggg atcatcccta tctttgatat aacaaactac       180
gcacagaaat tccagagcag agtcactatt accgcggaca aatccacgag caccgcctac       240
atggagctga gcagcctgcg ctctgaggac acggctgtgt attactgcgc acgcggaaat       300
ggtaactacg ccctggatgc tatggactac tggggtcagg gtacgttggt caccgtctcc       360
tca                                                                    363

<210> SEQ ID NO 22
<211> LENGTH: 121
<212> TYPE: PRT
<213> ORGANISM: Artificial sequence
<220> FEATURE:
<223> OTHER INFORMATION: Synthetic Amino acid sequence of PET1287A10 VH

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Ser
            20                  25                  30

Phe Ile Asn Trp Val Arg Gln Ala Pro Gly Gln Gly Leu Glu Trp Met
        35                  40                  45

Gly Gly Ile Ile Pro Ile Phe Asp Ile Thr Asn Tyr Ala Gln Lys Phe
    50                  55                  60

Gln Ser Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asn Gly Asn Tyr Ala Leu Asp Ala Met Asp Tyr Trp Gly
            100                 105                 110

Gln Gly Thr Leu Val Thr Val Ser Ser
        115                 120

<210> SEQ ID NO 23
<211> LENGTH: 5
<212> TYPE: PRT
<213> ORGANISM: Artificial sequence
<220> FEATURE:
<223> OTHER INFORMATION: Synthetic Amino acid sequence of PET1287A10
      HCDR1

<400> SEQUENCE: 23

Thr Ser Phe Ile Asn
1               5

<210> SEQ ID NO 24
<211> LENGTH: 17
<212> TYPE: PRT
<213> ORGANISM: Artificial sequence
<220> FEATURE:
<223> OTHER INFORMATION: Synthetic Amino acid sequence of PET1287A10
      HCDR2

<400> SEQUENCE: 24

Gly Ile Ile Pro Ile Phe Asp Ile Thr Asn Tyr Ala Gln Lys Phe Gln
1               5                   10                  15

Ser

<210> SEQ ID NO 25
<211> LENGTH: 12
<212> TYPE: PRT
<213> ORGANISM: Artificial sequence
<220> FEATURE:
<223> OTHER INFORMATION: Synthetic Amino acid sequence of PET1287A10
      HCDR3

<400> SEQUENCE: 25

Gly Asn Gly Asn Tyr Ala Leu Asp Ala Met Asp Tyr
1               5                   10

<210> SEQ ID NO 26
<211> LENGTH: 324
<212> TYPE: DNA
<213> ORGANISM: Artificial sequence
<220> FEATURE:
<223> OTHER INFORMATION: Synthetic Nucleotide sequence encoding
      PET1287A10 VL

<400> SEQUENCE: 26
gaaattgtgc tgactcagtc tccaggcacc ctgtctttgt ctccagggga aagagccacc      60
ctctcctgca gggccagtca gagtgttagc agcagctact tgcctggta ccagcagaaa      120 cctggccagg ctcccaggct cctcatctat ggtgcatcca gcagggccac tggcatccct     180
gacagattca gtggcagcgg gtctgggaca gatttcactc tcaccatcag ccgcctggag    240
cctgaagatt tcgcagttta ttactgtcag caatattatg atagtcccat caccttcggc   300
caagggacac gactggagat taaa                                            324

<210> SEQ ID NO 27
<211> LENGTH: 108
<212> TYPE: PRT
<213> ORGANISM: Artificial sequence
<220> FEATURE:
<223> OTHER INFORMATION: Synthetic Amino acid sequence of PET1287A10 VL

<400> SEQUENCE: 27

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Phe Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu

```
                65                  70                  75                  80
Pro Glu Asp Phe Ala Val Tyr Tyr Cys Gln Gln Tyr Tyr Asp Ser Pro
                        85                  90                  95

Ile Thr Phe Gly Gln Gly Thr Arg Leu Glu Ile Lys
                100                 105

<210> SEQ ID NO 28
<211> LENGTH: 12
<212> TYPE: PRT
<213> ORGANISM: Artificial sequence
<220> FEATURE:
<223> OTHER INFORMATION: Synthetic Amino acid sequence of PET1287A10
      LCDR1

<400> SEQUENCE: 28

Arg Ala Ser Gln Ser Val Ser Ser Ser Tyr Phe Ala
1               5                   10

<210> SEQ ID NO 29
<211> LENGTH: 7
<212> TYPE: PRT
<213> ORGANISM: Artificial sequence
<220> FEATURE:
<223> OTHER INFORMATION: Synthetic Amino acid sequence of PET1287A10
      LCDR2

<400> SEQUENCE: 29

Gly Ala Ser Ser Arg Ala Thr
1               5

<210> SEQ ID NO 30
<211> LENGTH: 9
<212> TYPE: PRT
<213> ORGANISM: Artificial sequence
<220> FEATURE:
<223> OTHER INFORMATION: Synthetic Amino acid sequence of PET1287A10
      LCDR3

<400> SEQUENCE: 30

Gln Gln Tyr Tyr Asp Ser Pro Ile Thr
1               5

<210> SEQ ID NO 31
<211> LENGTH: 11
<212> TYPE: PRT
<213> ORGANISM: Artificial sequence
<220> FEATURE:
<223> OTHER INFORMATION: Synthetic  Amino acid sequence of FR4

<400> SEQUENCE: 31

Trp Gly Gln Gly Thr Leu Val Thr Val Ser Ser
1               5                   10
```

TREATMENT OF MYOCARDIAL INFARCTION USING TGF-β ANTAGONISTS

CROSS REFERENCE TO RELATED APPLICATIONS

This application is a Continuation of application Ser. No. 15/145,062, filed May 3, 2016, which is a Continuation of application Ser. No. 13/819,393, filed Aug. 13, 2013, which is a U.S. National Stage of International Patent Application PCT/US2011/001536, filed on Sep. 1, 2011, which designated the United States and was published in the English language on Mar. 8, 2012, as WO 2012/030394 A1 and claims priority under 35 U.S.C. § 119e to U.S. Provisional Application No. 61/379,315, filed on Sep. 1, 2010; and the content of each is hereby expressly incorporated by reference in their entireties for all purposes and each is assigned to the assignee hereof.

BACKGROUND

Field of the Disclosure

This disclosure relates to methods of reducing adverse consequences of myocardial infarction.

Description of the Related Art

The problems and health consequences of heart disease are far reaching. Heart disease is the leading cause of death for both women and men in the United States. (Kung H C, Hoyert D L, Xu J, Murphy S L. Deaths: final data for 2005. National Vital Statistics Reports. 2008; 56(10)). Every 34 seconds a person in the United States dies from heart disease. More than 2,500 Americans die from heart disease each day. In 2005, 652,091 people died of heart disease (50.5% of them women). This was 27.1% of all U.S. deaths. Heart disease is the leading cause of death for American Indians and Alaska Natives, blacks, Hispanics, and whites. For Asians and Pacific Islanders, cancer is the leading cause of death (accounting for 27.5% of all deaths), heart disease is a close second (25.0%). (CDC. Deaths: leading causes for 2004. National Vital Statistics Reports. 2007; 56(5)). Almost 6 million hospitalizations each year (in the United States) are due to cardiovascular disease.

In 2009, heart disease is projected to cost more than $304.6 billion, including health care services, medications, and lost productivity. (American Heart Association. *Heart Disease and Stroke Statistics—2009 Update*. Dallas; AHA: 2009. Statistics Committee and Stroke Statistics Subcommittee. *Circulation.* 2008 Dec. 15.) Worldwide, coronary heart disease killed more than 7.6 million people in 2005. (World Health Organization. *The Global Burden of Disease: 2004 Update*. Geneva; WHO: 2008.) In 2003, approximately 37% of adults reported having two or more of six risk factors for heart disease and stroke (high blood pressure, high cholesterol, diabetes, current smoking, physical inactivity, and obesity). (Hayes D K, et al., Disparities in multiple risk factors for heart disease and stroke, 2003 *MMW.,* 2005; 54:113-116).

Myocardial infarction (MI) is cardiac tissue death caused by ischemia. "Ischemia" refers to local deficiency of blood supply, generally produced by vasoconstriction or local obstacles to blood flow. Restoration of blood flow to a previously ischemic tissue or organ, such as the heart is referred to as "reperfusion."

Acute myocardial infarction (AMI), or a "heart attack," occurs when localized myocardial ischemia causes the development of a defined region of tissue death. AMI is most often caused by rupture of an atherosclerotic lesion in a coronary artery. This causes the formation of a thrombus that plugs the artery, stopping it from supplying blood to the region of the heart that it supplies.

Severe and prolonged ischemia produces a region of necrosis spanning the entire thickness of the myocardial wall. Such a transmural infarct usually causes ST segment elevation. Less severe and protracted ischemia can arise when coronary occlusion is followed by spontaneous reperfusion; an infarct-related artery is not completely occluded; occlusion is complete, but an existing collateral blood supply prevents complete ischemia; or the oxygen demand in the affected zone of myocardium is smaller. Under these conditions, the necrotic zone may be mainly limited to the subendocardium, typically causing non-ST segment elevation MI.

Both infarcted and unaffected myocardial regions undergo progressive changes over the hours, days and weeks following an ischemic event. This process of postinfarct myocardial evolution leads to the occurrence of characteristic changes at predictable times after the initial event. Acute ischemia causes an immediate loss of contractility in the affected myocardium, a condition termed hypokinesis. Necrosis starts to develop in the subendocardium about 15-30 min after onset of acute ischemia. The necrotic region grows outward towards the epicardium over the next 3-6 h, eventually spanning the entire ventricular wall. At the edges of the infarct, the myocardium may be stunned (reversibly damaged) and will eventually recover if bloodflow is restored. Contractility in the remaining viable myocardium increases, a process termed hyperkinesis.

A progression of cellular, histological and gross changes develop within the infarct. Alterations in the gross appearance of infarcted tissue are not apparent for at least 6 h after the onset of cell death. However, cell biochemistry and ultrastructure begin to show abnormalities within 20 min. Cell damage is progressive, becomingly increasingly irreversible over about 12 h.

Between 4 and 12 h after cell death starts, the infarcted myocardium begins to undergo coagulation necrosis, a process characterized by cell swelling, organelle breakdown and protein denaturation. After about 18 h, neutrophils (phagocytic lymphocytes) enter the infarct. Their numbers reach a peak after about 5 days, and then decline. After 3-4 days, granulation tissue appears at the edges of the infarct zone. This consists of macrophages, fibroblasts (which lay down scar tissue), and new capillaries. The infarcted myocardium is especially soft between 4 and 7 days, and is therefore maximally prone to rupturing. As the granulation tissue migrates inward toward the centre of the infarct over several weeks, the necrotic tissue is engulfed and digested by the macrophages. The granulation tissue then progressively matures, with an increase in connective (scar) tissue and loss of capillaries. After 2-3 months, the infarct has healed, leaving a noncontracting region of the ventricular wall that is thinned, firm and pale grey.

Microscopic morphologic changes evolve over time as follows: Wavy myocardial fibers appear 1-3 hours after onset of ischemia. A staining defect with tetrazolium or basic fuchsin dye appears 2-3 hours after onset of ischemia. Coagulation necrosis with loss of cross striations, contraction bands, edema, hemorrhage, and early neutrophilic infiltrate appear 4-12 hours after onset of ischemia. Continuing coagulation necrosis, pyknosis of nuclei, and marginal contraction bands are apparent 18-24 hours after onset of ischemia. Total loss of nuclei and striations along with heavy neutrophilic infiltrate appears 24-72 hours after onset of ischemia. Macrophage and mononuclear infiltration, and, fibrovascular response begin 3-7 days after onset of ischemia. A fibrovascular response with prominent granulation tissue is apparent 10-21 days after onset of ischemia. Fibrosis is readily apparent 7 weeks or sooner after an ischemic event.

Complications can include: arrhythmias and conduction defects, extension of infarction or re-infarction, congestive heart failure, cardiogenic shock, pericarditis, mural thrombosis with possible embolization, myocardial wall rupture with possible tamponade, papillary muscle rupture with possible valvular insufficiency, and ventricular aneurysm formation.

SUMMARY

Disclosed herein is a method of reducing an adverse consequence of myocardial infarction in a patient comprising administering an antagonist of TGF-β to the patient during the acute stage of the myocardial infarction. In some embodiments, the myocardial infarction is an acute myocardial infarction. Administration of the antagonist of TGF-β may be commenced within 120 hours of onset of acute myocardial ischemia. In various embodiments, administration of the antagonist of TGF-β is commenced within about 72 hours, within about 48 hours, within about 24 hours, or within about 12 hours of onset of acute myocardial ischemia. Administration of the antagonist of TGF-β may be commenced prior to substantial macrophage and mononuclear infiltration of tissue affected by the myocardial infarction. In some embodiments, administration of the antagonist of TGF-β is commenced during a period characterized by neutrophilic infiltration of tissue affected by the myocardial infarction. In other embodiments, administration of the antagonist of TGF-β is commenced during a period characterized by necrosis of tissue affected by the myocardial infarction. Generally, the patient may be a human or a non-human mammal.

In some embodiments, the TGF-β antagonist may be selected from the group consisting of: (i) an antibody or antibody fragment that specifically binds to one or more isoforms of TGF-β; (ii) a TGF-β receptor or soluble fragment thereof; (iii) an antibody or antibody fragment that specifically binds to one or more TGF-β receptors; and (iv) an antisense or interfering RNA oligonucleotide.

In some embodiments, the method further comprises administering a compound that is capable of selectively restoring a desirable function of TGF-β to the patient. For example, a compound capable of selectively restoring a desirable function of TGF-β may be an anti-inflammatory drug, or an antagonist of TNF-α. In some embodiments, the method may include administering an ACE inhibitor to the patient. The ACE inhibitor may be selected from the group consisting of benazepril, captopril, fosinopril, moexipril, perindopril, quinapril, transdolapril, lisinopril, enalapril and ramipril. In other embodiments, the method may further comprise administering an angiotensin II receptor antagonist to the patient. The angiotensin II receptor antagonist may be selected from the group consisting of eprosartan, telmisartan, losartan, irbesartan, olmesartan, candesartan, and valsartan.

The TGF-β antagonist may be an antibody or antibody fragment that specifically binds to one or more isoforms of TGF-β and may neutralize one or more of human TGF-β1, TGF-β2 and TGF-β3. In some embodiments, the antibody or antibody fragment may comprise a PET1073G12 VH domain (SEQ ID NO: 2) with up to 5 mutations, or an antigen-binding portion thereof. In some embodiments, the antibody or antibody fragment comprises a PET1074B9 VH domain (SEQ ID NO: 12) with up to 5 mutations, or an antigen-binding portion thereof. In some embodiments, the antibody or antibody fragment comprises a PET1287A10 VH domain (SEQ ID NO: 22) with up to 5 mutations, or an antigen-binding portion thereof. In some embodiments, the antibody or antibody fragment comprises the PET1073G12 VL domain (SEQ ID NO: 7) with up to 5 mutations, or an antigen-binding portion thereof. In some embodiments, the antibody or antibody fragment comprises the PET1074B9 VL domain (SEQ ID NO: 17) with up to 5 mutations, or an antigen-binding portion thereof. In some embodiments, the antibody or antibody fragment comprises the PET1287A10 VL domain (SEQ ID NO: 27) with up to 5 mutations, or an antigen-binding portion thereof. In some embodiments, the antibody or antibody fragment comprises the PET 1073G12 VH domain (SEQ ID NO: 2) and the PET 1073G12 VL domain (SEQ ID NO: 7). In some embodiments, the antibody or antibody fragment comprises the PET 1074B9 VH domain (SEQ ID NO: 12) and the PET 1074B9 VL domain (SEQ ID NO: 17). In some embodiments, the antibody or antibody fragment comprises the PET 1287A10 VH domain (SEQ ID NO: 22) and the PET 1287A10 VL domain (SEQ ID NO: 27). In some embodiments, the antibody or antibody fragment comprises a set of CDRs (HCDR1, HCDR2 and HCDR3), wherein said HCDR3 has an amino acid sequence selected from the group consisting of SEQ ID NO: 5, SEQ ID NO: 15 and SEQ ID NO: 25. In some embodiments, the HCDR1, HCDR2 and HCDR3 of the VH domain are within a germline heavy chain framework. In some embodiments, the HCDR1, HCDR2 and HCDR3 of the VH domain are within a framework that comprises up to 12 mutations from the germline amino acid sequence. In some embodiments, the antibody or antibody fragment comprises a set of CDRs (LCDR1, LCDR2 and LCDR3), wherein said LCDR3 has an amino acid sequence selected from the group consisting of SEQ ID NO: 10, SEQ ID NO: 20 and SEQ ID NO: 30. In some embodiments, the LCDR1, LCDR2 and LCDR3 are within a germline heavy chain framework. In some embodiments, the LCDR1, LCDR2 and LCDR3 are within a framework that comprises up to 5 mutations from the germline amino acid sequence.

DETAILED DESCRIPTION

Figure 1:
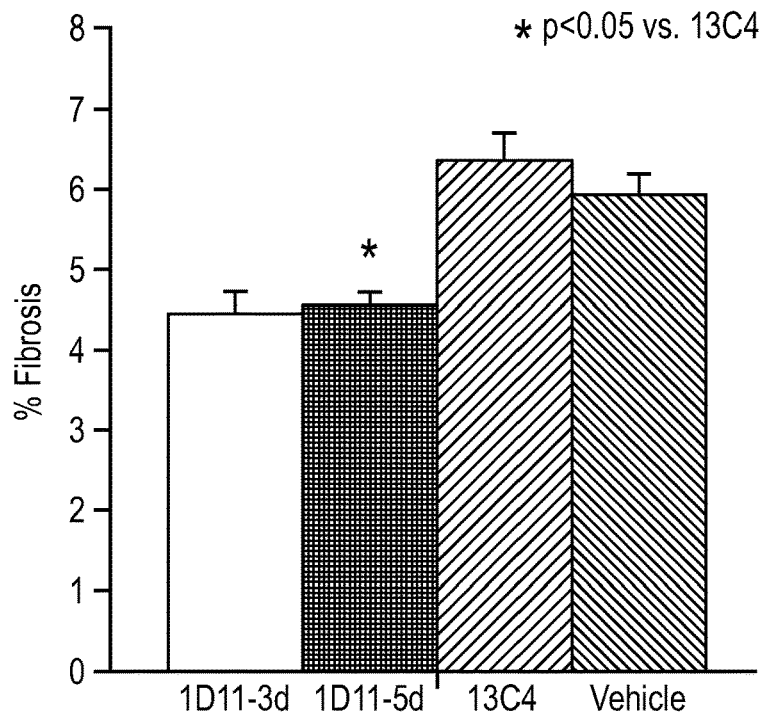
FIG. 1 shows a reduction in fibrosis with administration of 1D11-D3 and 1D11D-5 and 13C4.

After a MI, or heart attack, the heart starts to repair itself. This cardiac repair process can be separated into overlapping phases. The first phase is known as the inflammatory phase. Following the inflammatory phase is the proliferative phase. Ultimately, the maturation phase is the last phase of heart repair. (Bujak, M. and Frangogiannis, N G Cariovasc Res. 74:184-195 (2007)).

Immediately following a heart attack, the inflammatory phase is characterized by cardiomyocyte death, induction of cytokines and chemokines, and an influx of inflammatory cells to clear the dying tissue. During the proliferative phase, there is suppression of inflammatory mediators as well as an influx of cells that contribute to the formation of connective tissue fibers, fibroblasts, and endothelial cells into the infarcted area. Fibroblasts secrete extracellular matrix. The endothelial cells contribute to the formation of a microvascular network within the developing loose fibrous connective tissue, or granulation tissue. Infiltrated inflammatory cells then begin to undergo cell death, or what is known as apoptosis. Finally, during the maturation phase the granulation tissue from the proliferative phase organizes and matures into a dense fibrous connective tissue scar. This remodeling of the fibrotic response in the myocardium can be prolonged. In general, the inflammatory phase occurs from the time of infarction to 1-7 days post-MI. The proliferative phase occurs from approximately 5-14 days post-MI. Finally, the maturation phase starts from approximately 10-14 days post-MI and continues as long as cardiac remodeling occurs.

TGF-β is induced in infarcted myocardium and participates in all phases of post-MI repair, which has complicated attempts to define the role of this cytokine in cardiac repair. Thus, the precise role of TGF-β in cardiac repair following a MI has not been well understood. TGF-β is a multifunctional cytokine originally named for its ability to transform normal fibroblasts to cells capable of anchorage-independent growth. There are at least five forms of TGF-β currently identified: TGF-β1, TGF-β2, TGF-β3, TGF-β4, and TGF-β5. It is possible to purify this family of TGF-βs from various species including humans, mice, green monkeys, pigs, cows, chicks, and frogs. It is also possible to purify this family of TGF-βs from various body sources including bone, platelets, or placenta, for producing it in recombinant cell culture, and for determining its activity.

In humans, three isoforms, TGF-β1, TGF-β2 and TGF-β3, are known to exist. (Swiss Prot accession numbers P001137, P08112 and P10600 (respectively)). In their biologically active state, these three isoforms are 25 kDa homodimers comprising two 112 amino acid monomers joined by an inter-chain disulfide bridge. TGF-β1 differs from TGF-β2 by 27 amino acids, and from TGF-β3 by 22 amino acids. The differences are mainly conservative amino acid changes. The three-dimensional structure of TGF-β has been determined by X-ray crystallography and the receptor binding regions have been defined. Both human TGF-βs and mouse TGF-βs are similar. The human TGF-β1 has one amino acid difference from a mouse TGF-β1. Human TGF-β2 has only a three amino acid difference from mouse TGF-β2, and human and mice TGF-β3 are identical.

The term "TGF-β" or "transforming growth factor-beta" refers to the family of molecules described that have either the full-length, native amino acid sequence of any of the humans TGF-β isoforms. These include the latent forms ("latent TGF-β") and associated or unassociated complex of precursors and mature TGF-β. Reference to such TGF-β will be understood to be a reference to any one of the currently identified forms, including TGF-β1, TGF-β2, TGF-β3, TGF-β4, and TGF-β5 and latent versions thereof, as well as to human TGF-β species identified in the future, including polypeptides derived from the sequence of any known TGF-β and being at least about 75%, preferably at least about 80%, more preferably at least about 85%, still more preferably at least about 90%, and even more preferably at least about 95% homologous with the sequence. The specific terms "TGF-β1," "TGF-β2," and "TGF-β3," as well as "TGF-β4" and "TGF-β5," refer to the TGF-βs defined in the literature (e.g., Derynck et al., Nature, supra, Seyedin et al., J. Biol. Chem., 262, supra, and deMartin et al., supra). The term "TGF-β" refers to the gene encoding human TGF-β.

Members of the TGF-β family are proteins that have nine cysteine residues in the mature portion of the molecule, share at least 65% homology with other known TGF-β sequences in the mature region, and may compete for the same receptor. In addition, they all appear to be encoded as a larger precursor that shares a region of high homology near the N-terminus and shows conservation of three cysteine residues in the portion of the precursor that will later be removed by processing. TGF-β family members also appear to have a processing site with four or five amino acids.

An increase in the level of TGF-β activity is involved in a large number of pathologic conditions, including, but not limited to, the following: (i) fibrosis, scarring, and adhesion during wound healing; (ii) fibrotic diseases of the heart, lungs, liver, and kidneys; (iii) atherosclerosis and arteriosclerosis; (iv) certain types of cancer including cancer of the prostate, neuroendocrine tumors of the digestive system, cancer of the cervix, glioblastomas, and gastric cancer; (v) angiopathy, vasculopathy, nephropathy; (vi) systemic sclerosis; (vii) viral infection, such as hepatitis C and HIV; and (viii) immunological and inflammatory disorders and deficiencies, such as rheumatoid arthritis.

Initial studies into the role of TGF-β in cardiac injury indicate that a protective role occurs in the first or inflammatory phase of cardiac repair post-MI. In these initial studies, TGF-β was administered in models of myocardial ischemic injury within a few hours after ischemic injury. Lefer showed in isolated rat hearts that administration of TGF-β before, or immediately after ischemic cardiac injury reduced superoxide anions in coronary circulation, maintained endothelial-dependent coronary relaxation, reduced injury mediated from exogenous tumor necrosis factor (TNF), and prevented severe cardiac injury. (Lefer, et al. Science, 249:61, 1990). Lefer and colleagues went on to prove that TGF-β preserved endothelial function, particularly by maintenance of endothelium-derived relaxation factor (EDRF but now known as nitric oxide or NO) formation by the endothelium. (Lefer, A M. Biochem Pharmacol. 42: 1323-1327, 1991). Other studies with isolated cardiomyocytes or isolated heart preparations further elucidated mechanisms of TGF-β mediated cardioprotection.

Keller et al. (Journal of Cardiovascular Pharmacology, 30:197-204, 1997) showed that in canine cardiac I/R models when TGF-β was administered 30 min before ischemia/reperfusion, there was a 50% reduction in protein leak index (PLI) in the infarct zone immediately following reperfusion, as compared to untreated controls. However, no improvement in PLI was observed 48 hours post-reperfusion. In addition, TGF-β did not improve endothelial dependent relaxation in 1-hour or 48-hours post-reperfusion dogs. These results suggested that TGF-β may prevent increased coronary vascular permeability early in reperfusion but it may not prevent later coronary vascular injury. (Keller, et al., J Cardiovasc Pharmcol. 30:197-204, 1997).

More recently, the role of TGF-β in MI repair was investigated using TGF-β receptor antagonists to interrupt TGF-β signaling. In one study, Ikeuchi et al. (Cardiovascular Research, 64:526-35, 2004) blocked TGF-β signaling at the time of MI by intramuscular injection of a plasmid encoding the extracellular domain of the TGF-β type II receptor (TβIIR) in mice 7 days prior to MI. They observed increased mortality during the 24 hours after MI, increased inflammation, increased left ventricle (LV) dilation and contractile dysfunction despite no increase in infarct size as compared to untreated mice. To block TGF-β at a later stage post-MI, mice received intramuscular injections of TβIIR at either day 0 or day 7 after MI. Four weeks after MI, TβIIR treatment prevented LV dilatation, contractile dysfunction, cardiomyocyte hypertrophy and interstitial fibrosis in the noninfarcted myocardium. TGF-β was beneficial in early phase but the benefits were lost with sustained expression, leading to LV remodeling and failure.

In another study, Okada et al (Circulation, 11:2430-37, 2005) injected mice intramuscularly with an adenovirus encoding a soluble TGF-β type II receptor (Ad.CAGsTβRII) 3 days post-MI. In treated mice post-MI, survival was significantly improved. This was accompanied by significant attenuation of ventricular dilatation and improved cardiac function 4 weeks post-MI. MI size did not differ from control but MI thickness and circumference were smaller in treated animals. Apoptosis among infarct area myofibroblasts was less frequent in treated animals. Administration of Ad.CAG-sTβRII at 4 weeks post-MI was ineffective. Okada et al. considered that a critical window for inhibition of TGF-β occurred after three days and before four weeks. The injection in their study was purposely done at a time when it was considered that the treatment would not affect acute ischemic death of cardiomyocytes. Okada et al., believed that inhibition of TGF-β during the acute stage of MI is considered harmful.

Subsequent to these studies, TGF-β antagonism using an antagonist antibody effective against TGF-β1, 2 and 3, was investigated in MI repair. Frantz et al (Basic Research in Cardiology, 103:485-502, 2008) administered the TGF-β antagonist antibody or a negative-control antibody to mice starting at either 7 days prior to, or 5 days after, induction of MI by coronary artery ligation. The antibodies were administered every other day throughout the 8 week duration of the study. Mortality was significantly higher in the groups that received the anti-TGF-β antibody. In addition, both anti-TGF-β antibody treated groups demonstrated increased left ventricular dilatation. These authors concluded that anti-TGF-β treatment before or after coronary artery ligation increases mortality and worsens left ventricular remodeling. The authors suggest that differences in the duration of TGF-β antagonism and concentration of TGF-β antagonists may account for the difference in results between their study and those reported by Ikeuchi et al (2004) and Okada et al (2005).

Disclosed herein is a method of treating a patient suffering from myocardial infarction, particularly acute myocardial infarction, or of reducing an adverse consequence of myocardial infarction in a patient, the method comprising administering an antagonist of TGF-β to the patient during the acute stage of the myocardial infarction. The finding that administration of the antagonist of TGF-β may be advantageously commenced at a time less than 120 hours after the onset of acute myocardial ischemia is surprising. In some instances, the methods described herein contemplate that administration of the antagonist of TGF-β may be commenced within about 72 hours, within about 48 hours, within about 24 hours, or within about 12 hours of onset of acute myocardial ischemia. Generally, in the methods disclosed herein, a TGF-β antagonist is administered during the acute phase of MI. Administration of the antagonist of TGF-β may be commenced prior to substantial macrophage and mononuclear infiltration of tissue affected by the myocardial infarction. In some embodiments, administration of the antagonist of TGF-β is commenced during a period characterized by neutrophilic infiltration of tissue affected by the myocardial infarction. In other embodiments, administration of the antagonist of TGF-β is commenced during a period characterized by necrosis of tissue affected by the myocardial infarction.

"Treatment" refers to both therapeutic treatment and prophylactic or preventative measures. Those in need of treatment include those already with a treatable disorder as well as those in which the disorder is to be prevented. Treatment may or may not comprise a complete cure or recovery of normal function. Treatment may also comprise amelioration of undesired symptoms and/or a reduction in adverse consequences of a disorder. A "mammal" can be any animal classified as a mammal, including humans, domestic and farm animals, and zoo, sports, or pet animals, such as dogs, horses, cats, cows, etc. Preferably, the mammal is a primate, such as a monkey, ape, or human, for example. The term "effective amount" refers to an amount of a drug effective to treat a disease or disorder in a mammal.

Although certain TGF-β functions may be desired in the early phase post-MI, antagonism of TGF during the acute period and beyond can result in improved cardiac remodeling and function. However, where it is desired to restore one or more selected functions of TGF-β, one may wish to co-administer with a TGF-β antagonist, another compound that is capable of selectively restoring a desirable function of TGF-β. For example, a compound capable of selectively restoring a desirable function of TGF-β may be an anti-inflammatory drug, or an antagonist of TNF-α. It may also be desirable to co-administer another treatment, for example, the method may include administering an ACE inhibitor to the patient. The ACE inhibitor may be selected from the group consisting of benazepril, captopril, fosinopril, moexipril, perindopril, quinapril, transdolapril, lisinopril, enalapril and ramipril. In other embodiments, the method may further comprise administering an angiotensin II receptor antagonist to the patient. The angiotensin II receptor antagonist may be selected from the group consisting of eprosartan, telmisartan, losartan, irbesartan, olmesartan, candesartan, and valsartan.

Neutralizing antibodies can be used as TGF-β antagonists. An "antibody" is an immunoglobulin whether natural or partly or wholly synthetically produced. The term also covers any polypeptide or protein comprising an antigen-binding domain of an antibody. Antibody fragments which comprise an antigen-binding domain are molecules, such as Fab, scFv, Fv, dAb, Fd and diabodies. The term "antibody" is used in the broadest sense and specifically covers intact monoclonal antibodies, polyclonal antibodies, multispecific antibodies (e.g., bispecific antibodies) formed from at least two intact antibodies, and antibody fragments, so long as they exhibit the desired biological activity. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, monoclonal antibodies may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352: 624-628 (1991) and Marks et al., J. Mol. Biol., 222: 581-597 (1991), for example.

"Antibody fragments" comprise a portion of an intact antibody, preferably comprising the antigen-binding or variable region thereof. Examples of antibody fragments include Fab, Fab', F(ab')2, and Fv fragments; diabodies; linear antibodies; single-chain antibody molecules; and multispecific antibodies formed from antibody fragment(s). The terms "Fc receptor" or "FcR" are used to describe a receptor that binds to the Fc region of an antibody. The preferred FcR is a native-sequence human FcR.

The term "variable" in the context of an antibody or antibody fragment refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light-chain and the heavy-chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The term "hypervariable region" refers to the amino acid residues of an antibody that are responsible for antigen-binding. The hypervariable region generally comprises amino acid residues from a "complementarity-determining region" or "CDR." "Framework Region" or "FR" residues are those variable-domain residues other than the hypervariable region residues as herein defined.

"Fv" is the minimum antibody fragment that contains a complete antigen-recognition and antigen-binding site. This region consists of a dimer of one heavy-chain and one light-chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy-chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments that have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains. "Single-chain Fv" or "scFv" antibody fragments comprise the VH and VL domains of antibody, wherein these domains are present in a single polypeptide chain.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody), such as mouse, rat, rabbit, or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. (Jones et al., Nature, 321: 522-525 (1986); Riechmann et al., Nature, 332: 323-329 (1988); and Presta, Curr. Op. Struct. Biol., 2: 593-596 (1992).)

A "TGF-β antibody" refers to an antibody that binds to any of the isoforms of TGF-β, preferably binding to either TGF-β1, TGF-β2, or TGF-β3, or to any combination thereof, more preferably at least TGF-β1, or at least TGF-β2, and most preferably TGF-β1, or TGF-β1 together with TGF-β2. Optionally, the antibody may bind to at least TGF-β3.

One neutralizing mouse monoclonal antibody that binds TGF-β1, TGF-β2 and TGF-β3 isoforms is known as 1D11 and is available from R&D Systems (Catalog No. MAB-1835) of through the ATCC (Accession No. HB 9849). A mouse monoclonal antibody directed against human TGF-β1 is also available from R&D Systems. Neutralizing mouse monoclonal antibodies have also been generated from mice immunized with human TGF-β1 peptides comprising amino acid positions 48 to 60 (antibody reactive with TGF-β1, TGF-β2 and TGF-β3) and amino acid positions 86 to 101 (antibody specific for TGF-β1). (Hoefer and Anderer, Cancer Immunol. Immunother., 41: 302-308 (1995)). GC1008 is a humanized monoclonal IgG4 antibody that neutralizes all TGF-β isoforms and is suitable for therapeutic use in humans.

1D11 is a murine pan-specific anti-TGF-β antibody that neutralizes mouse TGF-β1, TGF-β2 and TGF-β3 and human TGF-β1 and TGF-β2 in a wide range of in vitro assays (U.S. Pat. No. 5,571,714; R&D System product sheet for MAB1835). In animal models of fibrosis, 1D11 has proven efficacious. However, 1D11 is a murine monoclonal antibody and may be unsuitable for therapeutic use in humans. Thus, in some embodiments a human antibody or a modified antibody comprising human sequence elements may be desired.

In some embodiments, methods of treating MI can comprise administration of antibodies against TGF-β to treat acute fibrosis that is associated with overproduction of TGF-β in TGF-β related diseases. The body responds to injury or disease by regenerating destroyed tissues. When the injury is prolonged or extensive, the destroyed tissue may be replaced by specialized fibrotic connective tissue. The deposition of this fibrotic tissue may result in an impairment of the affected tissue or organ function in the patient. Administration of an effective amount of anti-TGF-β antibody during the acute phase can reduce the subsequent development of fibrosis. Moreover, an effective amount of anti-TGF-β antibody may also be administered during the period of post-MI recovery that is typically characterized by fibrosis to neutralize the biologic activity of TGF-β, thereby reducing fibrotic development.

In some embodiments, the TGF-β antagonist may be selected from the group consisting of: (i) an antibody or antibody fragment that specifically binds to one or more isoforms of TGF-β; (ii) a TGF-β receptor or soluble fragment thereof; (iii) an antibody or antibody fragment that specifically binds to one or more TGF-β receptors; and (iv) an antisense or interfering RNA oligonucleotide. Anti-TGF-β antibodies that specifically bind and neutralize a TGF-β molecule are particularly useful as TGF-β antagonists. Examples of such antibodies are described in U.S. Patent Application Publication No. 2006/0251658. Anti-TGF-β antibodies include specific antibodies for TGF-β, in particular human TGF-β including specific antibodies that are directed to TGF-β1, TGF-β2 and TGF-β3.

As antibodies can be modified in a number of ways, the term "antibody molecule" should be construed as covering any antibody or substance having an antigen-binding site of an antibody with the required specificity. Thus, this term covers antibody fragments and derivatives, including any polypeptide comprising an antigen-binding domain, whether natural or wholly or partially synthetic. Chimeric molecules comprising an antigen-binding domain of an antibody, or equivalent, fused to another polypeptide are therefore included. Cloning and expression of chimeric antibodies are described in EP-A-0120694 and EP-A-0125023, and a large body of subsequent literature. This is why, unless specifically limited, the term anti-TGF-β antibody is broadly used herein to include whole antibodies (e.g., IgG, such as IgG1 or IgG4), antibody fragments (e.g., scFv, Fab, dAb), or molecules comprising an anti-TGF-β antigen-binding site derived from an anti-TGF-β antibody or components thereof.

Antagonists of TGF-β include humanized monoclonal anti-TGF-β antibodies having one or more amino acid residues and introducing into it from a source that is non-human. Humanization can be performed following the method of Winter and co-workers (Jones et al, Nature, 321: 522-525 (1986); Riechmann et al., Nature, 332: 323-327 (1988); Verhoeyen et al., Science, 239: 1534-1536 (1988)), by substituting hypervariable region sequences for the corresponding sequences of a human antibody. Accordingly, such "humanized" antibodies may be chimeric antibodies (for example, as described in U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al., J. Immunol., 151: 2296 (1993); Chothia et al, J. Mol. Biol., 196: 901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151: 2623 (1993)).

Preferably, humanized antibodies retain high affinity for the antigen and other favorable biological properties. To achieve this goal, humanized antibodies can be prepared by a process comprising analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Anti-TGF-β antibodies typically comprise antibody VH and VL domains. Within VH and VL domains are complementarity determining regions, CDRs, which may be comprised within different framework regions, FR's, to form VH or VL domains as the case may be. An antigen-binding site may consist of an antibody VH domain and/or a VL domain or antigen-binding portions thereof.

An anti-TGF-β antibody can comprise an HCDR set, an LCDR set, or both and/or a human antibody VH domain, VL domain or both.

A set of HCDR1, HCDR2 and HCDR3 may have sequences selected from the following sets:
HCDR1 SEQ ID NO: 3, HCDR2 SEQ ID NO: 4, HCDR3 SEQ ID NO: 5 (referred to herein as the "PET1073G12 set of HCDRs");
HCDR1 SEQ ID NO: 13, HCDR2 SEQ ID NO: 14, HCDR3 SEQ ID NO: 15 (referred to herein as the "PET1074B9 set of HCDRs");
HCDR1 SEQ ID NO: 23, HCDR2 SEQ ID NO: 24, HCDR3 SEQ ID NO: 25 (referred to herein as the "PET1287A10 set of HCDRs").

A set of LCDR1, LCDR2 and LCDR3 may have sequences selected from the following sets:
LCDR1 SEQ ID NO: 8, LCDR2 SEQ ID NO: 9, LCDR3 SEQ ID NO: 10 (referred to herein as the "PET1073G12 set of LCDRs");
LCDR1 SEQ ID NO: 18, LCDR2 SEQ ID NO: 19, LCDR3 SEQ ID NO: 20 (referred to herein as the "PET1074B9 set of LCDRs");
LCDR1 SEQ ID NO: 28, LCDR2 SEQ ID NO: 29, LCDR3 SEQ ID NO: 30 (referred to herein as the "PET1287A10 set of LCDRs").

The PET set of HCDRs together with the PET set of LCDRS is herein referred to as the PET1073G12 set of CDRs. The PET1074B9 set of HCDRs together with the PET1074B9 set of LCDRS is herein referred to as the PET1074B9 set of CDRs. The PET1287A10 set of HCDRs together with the PET1287A10 set of LCDRS is herein referred to as the PET1287A10 set of CDRs. A VH domain comprising a set of HCDRs as disclosed herein may comprise separately a VL domain comprising a set of LCDRs as disclosed herein. Preferably such a VH domain is paired with such a VL domain, and most preferably the VH and VL domain pairings are the same as in the clones as set out herein.

A VH domain of an anti-TGF-β antibody can contain a set of HCDRs HCDR1, HCDR2 and HCDR3 wherein the set of HCDRs corresponds to that for PET1073G12, PET1074B9 or PET1287A10 with one or two amino acid substitutions.

An anti-TGF-β antibody can comprise a VL domain comprising a set of LCDRs LCDR1, LCDR2 and LCDR3 wherein the set of CDRs corresponds to that for PET1073G12, PET1074B9 or PET1287A10 with one or two amino acid substitutions.

Following the lead of computational chemistry in applying multivariate data analysis techniques to the structure/property-activity relationships (Wold, et al. Multivariate data analysis in chemistry. Chemometrics—Mathematics and Statistics in Chemistry (Ed.: B. Kowalski), D. Reidel Publishing Company, Dordrecht, Holland, 1984 (ISBN 90-277-1846-6)) quantitative activity-property relationships of antibodies can be derived using well-known mathematical techniques, such as statistical regression, pattern recognition and classification (Norman et al. Applied Regression Analysis. Wiley-Interscience; 3rd edition (April 1998) ISBN: 0471170828; Abraham Kandel, Eric Backer. Computer-Assisted Reasoning in Cluster Analysis. Prentice Hall PTR; (May 11, 1995), ISBN: 0133418847; Wojtek Krzanowski. Principles of Multivariate Analysis: A User's Perspective (Oxford Statistical Science Series, No 22 (Paper)). Oxford University Press; (December 2000), ISBN: 0198507089; Ian H. Witten, Eibe Frank. Data Mining: Practical Machine Learning Tools and Techniques with Java Implementations. Morgan Kaufmann; (Oct. 11, 1999), ISBN: 1558605525; David G. T. Denison (Editor), Christopher C. Holmes, Bani K. Mallick, Adrian F. M. Smith. Bayesian Methods for Nonlinear Classification and Regression (Wiley Series in Probability and Statistics). John Wiley & Sons; (July 2002), ISBN: 0471490369; Amp K. Ghose, Vellarkad N. Viswanadhan. Combinatorial Library Design and Evaluation Principles, Software, Tools, and Applications in Drug Discovery. ISBN: 0-8247-0487-8). The properties of antibodies can be derived from empirical and theoretical models of antibody sequence, functional and three-dimensional structures (for example, analysis of likely contact residues or calculated physicochemical property) and these properties can be considered singly and in combination.

Analysis of antibodies of known atomic structure has elucidated relationships between the sequence and three-dimensional structure of antibody binding sites (Chothia C. et al. Journal Molecular Biology (1992) 227, 799-817; Al-Lazikani, et al. Journal Molecular Biology (1997) 273 (4), 927-948). These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions (Chothia et al. and Al-Lazikani et al., supra).

The sequence-structure relationship can be used for prediction of those residues in an antibody of known sequence, but of an unknown three-dimensional structure, which are important in maintaining the three-dimensional structure of its CDR loops and hence in maintaining binding specificity. These predictions can be confirmed by comparison of the predictions to the output from lead optimization experiments. In a structural approach, a theoretical model can be created of the antibody molecule (Chothia, et al. Science, 223, 755-758 (1986)) using any freely available or commercial package, such as WAM (Whitelegg, N. R. u. and Rees, A. R (2000) Prot. Eng., 12, 815-824). A protein visualisation and analysis software package, such as Insight II (Accelerys, Inc.) or Deep View (Guex, N. and Peitsch, M. C. Electrophoresis (1997) 18, 2714-2723) may then be used to evaluate possible substitutions at each position in the CDR and FR. This information may then be used to make substitutions likely to have a minimal or beneficial effect on activity. The techniques required to make substitutions within amino acid sequences of CDRs, antibody VH or VL domains and specific antibodies generally is available in the art. Variant sequences may be made, with substitutions that may or may not be predicted to have a minimal or beneficial effect on activity.

Thus, an anti-TGF-β antibody can comprise a defined set of CDRs, in particular the set of CDRs of PET1073G12, PET1074B9 and PET1287A10, and sets of CDRs of PET1073G12, PET1074B9 or PET1287A10 with one or two substitutions within the set of CDRs. The relevant set of CDRs is provided within antibody framework regions or other protein scaffolds, e.g., fibronectin or cytochrome B. Preferably antibody framework regions are employed.

The heavy chain of an anti-TGF-β antibody can utilize a human $V_H1$ family gene. In various embodiments, the heavy chain framework amino acid sequence contains 1-12, preferably 3-12 and more preferably 3-8 amino acid differences as compared to the germline amino acid sequence of the human $V_H1$ family gene. In some embodiments, the heavy chain framework sequence is the germline sequence. In particularly preferred embodiments, the antibody framework region for the heavy chain may be human DP-10 ($V_H$ 1-69) or human DP-88 ($V_H1$-e) from the $V_H1$ family. Some embodiments utilizing a human DP-10 gene have a non-germline amino acid at residues 27, 78 and 94. In some embodiments, residue 27 is tyrosine, residue 78 is threonine and residue 94 is serine or leucine. In some embodiments, the light chain utilizes a human Vκ3 family gene with 1-5, 1-4, more preferably 1-3 amino acid differences as compared to the germline amino acid sequence. In some embodiments, the light chain framework sequence is the germline human $V_κ3$ family gene sequence. In particularly preferred embodiments, the framework region for the light chain may be human DPK-22 (A27). In some such embodiments, residue 2 is a non-germline amino acid. In some embodiments residue 2 is a threonine.

In a highly preferred embodiment, a VH domain is provided with the amino acid sequence of SEQ ID NO: 2, this being termed "PET1073G12 VH domain," or SEQ ID NO: 12, this being termed "PET1074B9 VH domain," or SEQ ID NO: 22, this being termed "PET1287A10 VH domain."

In some embodiments, a VL domain comprises the amino acid sequence of SEQ ID NO: 7, this being termed "PET1073G12 VL domain" or SEQ ID NO: 17, this being termed "PET1074B9 VL domain," or SEQ ID NO: 27, this being termed "PET1287A10 VL domain". One example anti-TGF-β antibody is composed of the PET1073G12 VH domain, SEQ ID NO: 2, and the PET1073G12 VL domain, SEQ ID NO: 7. Another example is composed of the PET1074B9 VH domain, SEQ ID NO: 12, and the PET1074B9 VL domain, SEQ ID NO: 17. Another example is composed of the PET1287A10 VH domain, SEQ ID NO: 22, and the PET1287A10 VL domain, SEQ ID NO: 27. These or any other antibody TGF-β-binding site may be comprised within any desired antibody molecule format, e.g., scFv, Fab, IgG1, IgG4, dAb etc., as is discussed further elsewhere herein. Another example is an IgG4 antibody molecule comprising the PET1073G12, PET1074B9 or PET1287A10 VH domain, preferably also comprising the corresponding PET1073G12, PET1074B9 or PET1287A10 VL domain.

Other IgG4 or other antibody molecules comprising the PET1073G12, PET1074B9 or PET1287A10 VH domain, and/or the PET1073G12, PET1074B9 or PET1287A10 VL domain, are further examples as are other antibody molecules comprising the PET1073G12, PET1074B9 or PET1287A10 set of HCDRs within an antibody VH domain, and/or the PET1073G12, PET1074B9 or PET1287A10 set of LCDRs within an antibody VL domain.

An anti-TGF-β antibody may be an antibody which binds all three isoforms of human TGF-β. Such an anti-TGF-β antibody can comprise the PET1073G12, PET1074B9 or PET1287A10 VH and/or VL domain or antigen-binding portions of those domains. In some embodiments, a VH domain from one of the above is paired with a VL domain from one of the above to provide an antigen-binding site. For example, the PET1073G12 VH domain (SEQ ID NO: 2) can be paired with the PET1073G12 VL domain (SEQ ID NO: 7), so that an antigen-binding site is formed comprising both the PET1073G12 VH and VL domains. In another embodiment, the PET1074B9 VH domain (SEQ ID NO: 12) is paired with the PET1074B9 VL domain (SEQ ID NO: 17), so that an antigen-binding site is formed comprising both the PET1074B9 VH and VL domains. In another embodiment, the PET1287A10 VH domain (SEQ ID NO: 22) is paired with the PET1287A10 VL domain (SEQ ID NO: 27), so that an antigen-binding site is formed comprising both the PET1287A10 VH and VL domains. In other embodiments, a PET1073G12, PET1074B9 or PET1287A10 VH domain is paired with a VL domain other than the corresponding PET1073G12, PET1074B9 or PET1287A10 VL.

Similarly, any set of HCDRs disclosed herein can be provided in a VH domain that is used as a specific antibody alone or in combination with a VL domain. A VH domain may be provided with a set of HCDRs as disclosed herein, and if such a VH domain is paired with a VL domain, then the VL domain may be provided with a set of LCDRs disclosed herein. A pairing of a set of HCDRs and a set of LCDRs may be as disclosed herein for the PET1073G12, PET1074B9 and PET1287A10 antibodies. The framework regions of the VH and/or VL domains may be germline frameworks. Frameworks regions of the heavy chain domain may be selected from the VH-1 family, and a preferred $V_{H-1}$ framework is DP-10 or DP-88 framework. Framework regions of the light chain may be selected from the $V_κ3$ family, and a preferred such framework is DPK-22.

One or more CDRs may be taken from a VH or VL domain of which the sequence is disclosed herein and incorporated into a suitable framework. This is discussed further herein. The same applies for other CDRs and sets of CDRs of antibodies as obtained using methods described herein.

An antibody VH domain, an antibody VL domain, a set of HCDRs, a set of LCDRs, a set of CDRs, one or more HCDRs, e.g., an HCDR3, and/or one or more LCR's, e.g., an LCDR3, may be employed in a TGF-β antagonist.

Variants of the VH and VL domains and CDRs, including those for which amino acid sequences are set out herein, and which can be employed in specific antibodies for TGF-β can be obtained by means of methods of sequence alteration or mutation and screening.

Variable domain amino acid sequence variants of any of the VH and VL domains whose sequences are specifically disclosed herein may be employed in the methods disclosed herein. Particular variants may include one or more amino acid sequence alterations (addition, deletion, substitution and/or insertion of an amino acid residue), may be less than about 20 alterations, less than about 15 alterations, less than about 10 alterations or less than about 5, 4, 3, 2 or 1 alteration. Alterations may be made in one or more framework region and/or one or more CDR.

A human, humanized, chimeric or synthetic specific antibody that competes or cross-competes for binding to antigen with any specific antibody that both binds the antigen and comprises a specific antibody antigen-binding region, VH and/or VL domain disclosed herein, set of CDRs or HCDR3 disclosed herein, or a variant of any of these can be used in the methods disclosed herein. Competition between antibodies may be assayed easily in vitro, for example, using ELISA and/or by tagging a specific reporter molecule to one antibody which can be detected in the presence of other untagged antibody(s), to enable identification of specific antibodies which bind the same epitope or an overlapping epitope. Cross-competition between antibodies may be readily assayed by running the reverse assay, e.g., by reversing the tagged and the untagged antibodies to identify pairs that block binding in both directions.

An antibody comprising an antigen-binding site of an antibody that competes or cross-competes with a PET1073G12, PET1074B9 or PET1287A10 antibody molecule, in particular PET1073G12, PET1074B9 or PET1287A10 scFv and/or IgG4 can be used for antagonizing TGF-β. In various embodiments, the antibody is a human, humanized, chimeric or synthetic antibody. In further aspects, an antibody can be used comprising an antigen-binding site of a human, humanized, chimeric or synthetic antibody which competes or cross-competes with an antigen-binding site described herein for binding to TGF-β, wherein the antigen-binding site of the human, humanized, chimeric or synthetic antibody is composed of a VH domain and a VL domain, and wherein the VH and VL domains comprise a set of CDRs as disclosed herein.

Given the information disclosed herein, various methods are available in the art for making human, humanized, chimeric or synthetic antibodies against TGF-β and which may compete or cross-compete with a PET1073G12, PET1074B9 or PET1287A10 antibody molecule, an antibody molecule with a PET1073G12, PET1074B9 or PET1287A10 set of CDRs, an antibody molecule with a set of PET1073G12, PET1074B9 or PET1287A10 HCDRs, or an antibody molecule with a set of PET1073G12, PET1074B9 or PET1287A10 LCDRs, for use as a TGF-β antagonist.

One or more specific antibodies able to bind TGF-β1, TGF-β2 and TGF-β3, may be obtained by a method including bringing into contact a library of antibodies and TGF-βs, and selecting one or more specific antibodies of the library able to bind all of said TGF-βs. The library may be displayed on the surface of bacteriophage particles, each particle containing nucleic acid encoding the antibody VH variable domain displayed on its surface, and optionally also a displayed VL domain if present. Following selection of specific antibodies able to bind the antigen and displayed on bacteriophage particles, nucleic acid may be taken from a bacteriophage particle displaying a said selected specific antibody. Such nucleic acid may be used in subsequent production of a specific antibody or an antibody VH variable domain (and optionally an antibody VL variable domain) by expression from a nucleic acid with the sequence of nucleic acid taken from a bacteriophage particle displaying a said selected specific antibody.

An antibody VH domain with the amino acid sequence of an antibody VH domain of a said selected specific antibody may be provided in isolated form, as may a specific antibody comprising such a VH domain. Ability to bind all three isoforms of TGF-β may be further tested, also ability to compete or cross-compete with PET1073G12, PET1074B9 or PET1287A10 (e.g., in scFv format and/or IgG format, e.g., IgG4) for binding to all three human isoforms of TGF-β.

An antibody for use as a TGF-β antagonist may bind TGF-β1, TGF-β2 and/or TGF-β3 with the affinity of a PET1073G12, PET1074B9 or PET1287A10 antibody molecule, e.g., scFv, or preferably IgG4, or with an affinity that is greater than one of the above molecules. A useful antibody may neutralize TGF-β1, TGF-β2 and/or TGF-β3 with the potency of a PET1073G12, PET1074B9 or PET1287A10 antibody molecule, e.g., scFv, or preferably PET1073G12, PET1074B9 or PET1287A10 IgG4, or with a potency that is greater than one of the above molecules.

An antibody for use as a TGF-β antagonist may neutralize naturally-occurring TGF-β with the potency of a PET1073G12, PET1074B9 or PET1287A10 antibody molecule, e.g., scFv, or preferably IgG4, or with a potency that is greater than one of the above molecules. Binding affinity and neutralization potency of different specific antibodies can be as compared under appropriate conditions.

An antibody for use as a TGF-β antagonist includes human, humanized, chimeric or synthetic antibodies that can neutralize naturally-occurring TGF-β with a potency that is equal to or greater than the potency of a TGF-β antigen-binding site formed by PET1073G12, PET1074B9 or PET1287A10 VH domain and the corresponding PET1073G12, PET1074B9 or PET1287A10 VL domain.

In addition to antibody sequences, an antibody for use as a TGF-β antagonist may comprise other amino acids, e.g., forming a peptide or polypeptide, such as a folded domain, or to impart to the molecule another functional characteristic in addition to ability to bind antigen. Specific antibodies may carry a detectable label, or may be conjugated to a toxin or a targeting moiety or enzyme (e.g., via a peptidyl bond or linker).

An antigen-binding antibody comprises an antigen-binding site. An antigen-binding site may also be provided by means of arrangement of CDRs on non-antibody protein scaffolds, such as fibronectin or cytochrome B, etc. Koide et al., (1998) Journal of Molecular Biology, 284:1141-1151; Nygren et al. (1997) Current Opinion in Structural Biology, Vol. 7:463-469). Scaffolds for engineering novel binding sites in proteins have been reviewed in detail by Nygren et al., supra. Protein scaffolds for antibody mimics are disclosed in WO 00/34784, which describes proteins (antibody mimics) that include a fibronectin type III domain having at least one randomised loop. A suitable scaffold into which to graft one or more CDRs, e.g., a set of HCDRs, may be provided by any domain member of the immunoglobulin gene superfamily. The scaffold may be a human or non-human protein.

An advantage of a non-antibody protein scaffold is that it may provide an antigen-binding site in a conserved framework region that is smaller and/or easier to manufacture than at least some antibody molecules. Small size of an antibody may confer useful physiological properties, such as an ability to enter cells, penetrate deep into tissues or reach targets within other structures, or to bind within protein cavities of the target antigen.

Typical are proteins having a stable backbone and one or more variable loops, in which the amino acid sequence of the loop or loops is specifically or randomly mutated to create an antigen-binding site having specificity for binding the target antigen. Such proteins include the IgG-binding domains of protein A from *S. aureus*, transferrin, tetranectin, fibronectin (e.g., 10th fibronectin type III domain) and lipocalins. Other approaches include synthetic "Microbodies" (Selecore GmbH), which are based on cyclotides—small proteins having intra-molecular disulphide bonds.

In addition to antibody sequences and/or an antigen-binding site, an antibody may comprise other amino acids, e.g., forming a peptide or polypeptide, such as a folded domain, or to impart to the molecule another functional characteristic in addition to ability to bind antigen. Antibodies may carry a detectable label, or may be conjugated to a toxin or a targeting moiety or enzyme (e.g., via a peptidyl bond or linker). For example, an antibody may comprise a catalytic site (e.g., in an enzyme domain) as well as an antigen-binding site, wherein the antigen-binding site binds to the antigen and thus targets the catalytic site to the antigen. The catalytic site may inhibit biological function of the antigen, e.g., by cleavage.

Although, as noted, CDRs can be carried by scaffolds, such as fibronectin or cytochrome B (Haan & Maggos, 2004 BioCentury, 12(5): A1-A6; Koide et al., supra; Nygren et al., supra), the structure for carrying a CDR or a set of CDRs will generally be of an antibody heavy or light chain sequence or substantial portion thereof in which the CDR or set of CDRs is located at a location corresponding to the CDR or set of CDRs of naturally-occurring VH and VL antibody variable domains encoded by rearranged immunoglobulin genes. The structures and locations of immunoglobulin variable domains may be determined by reference to Kabat, et al., 1987, and updates thereof, now available on the Internet (URL: immuno.bme.nwu.edu or find "Kabat" using any search engine).

It is possible to take monoclonal and other antibodies and use techniques of recombinant DNA technology to produce other antibodies or chimeric molecules which retain the specificity of the original antibody. Such techniques may involve joining DNA encoding an immunoglobulin variable region to a constant region, or introducing the complementarity determining regions (CDRs), of an antibody into the constant region plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

Further techniques available in the art of antibody engineering have made it possible to isolate human and humanized antibodies. For example, human hybridomas can be made as described by Kontermann et al. (Kontermann R and Dubel Stefan; Antibody Engineering, Springer-Verlag New York, LLC; 2001, ISBN: 3540413545). Phage display, another established technique for generating antibodies has been described in detail in many publications, such as Kontermann et al., supra, and WO 92/01047 (discussed further below). Transgenic mice in which the mouse antibody genes are inactivated and functionally replaced with human antibody genes while leaving intact other components of the mouse immune system, can be used for isolating human antibodies to human antigens (Mendez et al., 1997). Human antibodies, either monoclonal or polyclonal, can also be made in other transgenic animals, such as goats, cows, sheep, rabbits, etc.

Synthetic antibody molecules created by expression from genes generated by means of oligonucleotides synthesized and assembled within suitable expression vectors, for example, as described by Knappik et al., supra or Krebs et al., Journal of Immunological Methods 254:67-84 (2001), can be used as TGF-β antagonists.

Fragments of a whole antibody can perform the function of binding antigens. Examples of binding fragments are (i) the Fab fragment consisting of VL, CL, VH and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989), McCafferty et al. (1990) Nature, 348, 552-554), which consists of a VH domain; (v) isolated CDR regions; (vi) F(ab')2 fragments, a bivalent fragment comprising two linked Fab fragments; (vii) single chain Fv molecules (scFv), wherein a VH domain and a VL domain are linked by a peptide linker which allows the two domains to associate to form an antigen-binding site (Bird et al., Science, 242, 423-426, 1988; Huston et al., Proc. Natl. Acad. Sci USA 85, 5879-5883; 1998; (viii) bispecific single chain Fv dimers (PCT/US92/09665); and (ix) "diabodies," multivalent or multi-specific fragments constructed by gene fusion (WO/13804); F. Holliger et al., Proc. Natl. Acad. Sci. USA 90 6444-6448, 1993). Fv, scFv or diabody molecules may be stabilized by the incorporation of disulphide bridges linking the VH and VL domains (Y. Reiter et al., Nature Biotech, 14, 1239-1245, 1996). Minibodies comprising a scFv joined to a CH3 domain may also be made (S. Hu et al., Cancer Res., 56, 3055-3061, 1996).

A dAb (domain antibody) is a small monomeric antigen-binding fragment of an antibody, namely the variable region of an antibody heavy or light chain (Holt et al., 2003). VH dabs occur naturally in camelids (e.g., camel, llama) and may be produced by immunising a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. An antibody may be a dAb comprising a VH or VL domain substantially as set out herein, or a VH or VL domain comprising a set of CDRs substantially as set out herein.

Where bispecific antibodies are to be used, these may be conventional bispecific antibodies, which can be manufactured in a variety of ways (Holliger, P. and Winter G. Current Opinion Biotechnol. 4, 446-449 (1993)), e.g., prepared chemically or from hybrid hybridomas, or may be any of the bispecific antibody fragments mentioned above. Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides, such as antibody fragments) of appropriate binding specificities can be readily selected using phage display (WO94/13804) from libraries. If one arm of the diabody is to be kept constant, for instance, with a specificity directed against TGF-β, then a library can be made where the other arm is varied and an antibody of appropriate specificity selected. Bispecific whole antibodies may be made by knobs-into-holes engineering (C. E. B. Ridgeway et al., Protein Eng., 9, 616-621, 1996).

Antibodies may be glycosylated, either naturally or by systems of various eukaryotic cells (e.g., CHO or NS0 (ECACC 85110503) cells, or they may be (for example, if produced by expression in a prokaryotic cell) unglycosylated. Glycosylation may also be intentionally altered, for example, by inhibiting fucosylation, increase ADCC activity of the resulting antibody. Accordingly, antibodies may be expressed so as to minimize or eliminate fucosylation.

In some embodiments, the CDR or VH or VL domain will be either identical or highly similar to the specified regions of which the sequence is set out herein. It is contemplated that from 1 to 5, preferably from 1 to 4 or 1 or 2, or 3 or 4, amino acid substitutions may be made in the CDR and/or VH or VL domains. VH or VL domains and CDRs and sets of CDRs that are highly similar to those for which sequences are given herein are encompassed by aspects, as are those with sequences that are substantially as set out herein.

The structure for carrying a CDR or a set of CDRs will generally be of an antibody heavy or light chain sequence or substantial portion thereof in which the CDR or set of CDRs is located at a location corresponding to the CDR or set of CDRs of naturally-occurring VH and VL antibody variable domains encoded by rearranged immunoglobulin genes. The structures and locations of immunoglobulin variable domains may be determined by reference to Kabat, E. A. et al., Sequences of Proteins of Immunological Interest. 4th Edition. US Department of Health and Human Services. 1987, and updates thereof, now available on the Internet (URL: immuno.bme.nwu.edu or find "Kabat" using any search engine). CDRs are defined according to Kabat et al. CDRs can also be carried by other scaffolds, such as fibronectin or cytochrome B.

Preferably, a CDR amino acid sequence substantially as set out herein is carried as a CDR in a human variable domain or a substantial portion thereof. The HCDR3 sequences substantially as set out herein represent preferred embodiments and it is preferred that each of these is carried as a HCDR3 in a human heavy chain variable domain or a substantial portion thereof.

Variable domains employed may be obtained or derived from any germ-line or rearranged human variable domain, or may be a synthetic variable domain based on consensus or actual sequences of known human variable domains. A CDR sequence (e.g., CDR3) may be introduced into a repertoire of variable domains lacking a CDR (e.g., CDR3), using recombinant DNA technology. Preferred germline frameworks have been identified already herein.

Marks et al. (Bio/Technology, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VK variable domains lacking a CDR2. Marks et al. further describe how this repertoire may be combined with a CDR2 of a particular antibody. Using analogous techniques, the CDR3-derived sequences may be shuffled with repertoires of VH or VL domains lacking a CDR3, and the shuffled complete VH or VL domains combined with a cognate VL or VH domain to provide antibodies. The repertoire may then be displayed in a suitable host system, such as the phage display system of WO92/01047 or any of a subsequent large body of literature, including Kay, B. K., Winter, J., and McCafferty, J. (1996) Phage Display of Peptides and Proteins: A Laboratory Manual, San Diego: Academic Press, so that suitable antibodies may be selected. A repertoire may consist of from $10^4$ individual members upwards, for example, from $10^6$ to $10^8$ or $10^{10}$ members. Other suitable host systems include yeast display, bacterial display, T7 display, ribosome display, covalent display and so on.

Analogous shuffling or combinatorial techniques are also disclosed by Stemmer (Nature, 1994, 370:389-391), who describes the technique in relation to a β-lactamase gene but observes that the approach may be used for the generation of antibodies.

A further alternative is to generate novel VH or VL regions carrying CDR-derived using random mutagenesis of one or more selected VH and/or VL genes to generate mutations within the entire variable domain. Such a technique is described by Gram et al. Proc. Natl. Acad. Sci., USA, 89:3576-3580), who used error-prone PCR. In preferred embodiments one or two amino acid substitutions are made within a set of HCDRs and/or LCDRs. Another method which may be used is to direct mutagenesis to CDR regions of VH or VL genes. Such techniques are disclosed by Barbas et al., (1994, Proc. Natl. Acad. Sci., USA, 91:3809-3813) and Schier et al. J. Mol. Biol. 263:551-567). Given the disclosure provided herein, the skilled person will be able to use such techniques to obtain additional antibodies using routine methodology in the art. The PET1073G12, PET1074B9 or PET1287A10 VH domain may be subject to mutation to provide one or more VH domain amino acid sequence variants which may be combined with one or more VL domains.

The VH domain may have a germline sequence, and in preferred embodiments is DP-10 or DP-88. A VL domain sequence may have a germline sequence, and in preferred embodiments is DPK-22. One or more of PET1073G12, PET1074B9 or PET1287A10 HCDR1, HCDR2 and HCDR3, or the PET1073G12, PET1074B9 or PET1287A10 set of HCDRs, may be employed, and/or one or more of PET1073G12, PET1074B9 or PET1287A10 LCDR1, LCDR2 and LCDR3, or the PET1073G12, PET1074B9 or PET1287A10 set of LCDRs.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally-occurring variable domain regions. For example, construction of antibodies made by recombinant DNA techniques may result in the introduction of N- or C-terminal residues encoded by linkers introduced to facilitate cloning or other manipulation steps. Other manipulation steps include the introduction of linkers to join variable domains to further protein sequences including immunoglobulin heavy chains, other variable domains (for example, in the production of diabodies) or protein labels.

Antibodies comprising a pair of VH and VL domains are preferred, single binding domains based on either VH or VL domain sequences may also be used. It is known that single immunoglobulin domains, especially VH domains, are capable of binding target antigens in a specific manner. In the case of either of the single specific binding domains, these domains may be used to screen for complementary domains capable of forming a two-domain antibody able to bind the three isoforms of human TGF-β.

This may be achieved by phage display screening methods using the so-called hierarchical dual combinatorial approach as disclosed in WO92/01047, in which an individual colony containing either an H or L chain clone is used to infect a complete library of clones encoding the other chain (L or H) and the resulting two-chain antibody is selected in accordance with phage display techniques, such as those described in that reference.

Anti-TGF-β antibodies may further comprise antibody constant regions or parts thereof. For example, a VL domain may be attached at its C-terminal end to antibody light chain constant domains including human $C_\kappa$ or $C_\lambda$ chains, preferably $C_\kappa$ chains. Similarly, an antibody based on a VH domain may be attached at its C-terminal end to all or part (e.g., a CH1 domain) of an immunoglobulin heavy chain derived from any antibody isotype, e.g., IgG, IgA, IgE and IgM and any of the isotype sub-classes, particularly IgG1 and IgG4. IgG4 is preferred. IgG4 is preferred for some applications because it does not bind complement has reduced effector functions. Where effector function is desired, IgG1 is preferred. Effector function may also be increased by manipulating the glycosylation state of the antibody, such as by decreasing the fucose content, by methods which are known in the art. The heavy chain may or may not have a C-terminal lysine residue. Any synthetic or other constant region variant that has these properties and stabilizes variable regions may also be used in some embodiments.

Heterogeneous preparations of the antibodies or antigen-binding fragments thereof may be useful. For example, such preparations may be mixtures of antibodies with full-length heavy chains and antibodies with heavy chains lacking the C-terminal lysine, with various degrees of glycosylation, with derivatized amino acids, such as cyclization of an N-terminal glutamic acid to form a pyroglutamic acid residue and/or with deamidated forms of the heavy and or light chain.

Compositions comprising TGF-β antibodies may be administered to individuals in need thereof, preferably in a "therapeutically effective amount," this being sufficient to show benefit to a patient. Such benefit may be at least amelioration of at least one symptom of a particular disease or disorder. The actual amount administered, and rate and time-course of administration, will depend on the nature and severity of the disease being treated. Prescription of treatment, e.g., decisions on dosage etc, may be determined based on preclinical and clinical, studies the design of which is well within the level of skill in the art.

Antibodies may be administered by injection (for example, subcutaneously, intravenously, intracavity (e.g., after tumor resection), intralesionally, intraperitoneally or intramuscularly), by inhalation, or topically (for example, intraocular, intranasal, rectal, into wounds, on skin), or orally. The route of administration can be determined by the physicochemical characteristics of the product, by special considerations for the disease, by dose or dose interval or by the requirement to optimise efficacy or to minimise side-effects.

It is envisaged that anti-TGF-β treatment need not be restricted to administration by healthcare professionals. Therefore, subcutaneous injection, especially using a needle-free device may be appropriate.

The precise dose will depend upon a number of factors, including, the condition and medical history of the patient, the precise nature of the antibody (e.g., whole antibody, fragment or diabody), and the nature of any detectable label or other molecule attached to the antibody. A typical antibody dose will be in the range 100 μg to 1 gm for systemic applications, and 1 μg to 1 mg for topical applications. Typically, the antibody will be a whole antibody, preferably the IgG4 isotype. This is a dose for a single treatment of an adult patient, which may be proportionally adjusted for children and infants, and also adjusted for other antibody formats in proportion to molecular weight and activity. Treatments may be repeated at daily, twice-weekly, weekly, monthly or other intervals, at the discretion of the physician.

Antibodies will usually be administered in the form of a pharmaceutical composition, which may comprise at least one component in addition to the antibody. Pharmaceutical compositions for use in methods of treating AMI, may comprise, in addition to active ingredient, a pharmaceutically-acceptable excipient, carrier, buffer, stabiliser or other materials well known to those skilled in the art. Such materials should be non-toxic and should not interfere with the efficacy of the active ingredient. Such materials could include, for example, any and all solvents, dispersion media, coatings, antibacterial and antifungal agents, isotonic and absorption delaying agents, and the like that are physiologically compatible. Some examples of pharmaceutically-acceptable carriers are water, saline, phosphate buffered saline, dextrose, glycerol, ethanol and the like, as well as combinations thereof. In many cases, it will be preferable to include isotonic agents, for example, sugars, polyalcohols, such as mannitol, sorbitol, or sodium chloride in the composition. Additional examples of pharmaceutically-acceptable substances are wetting agents or minor amounts of auxiliary substances, such as wetting or emulsifying agents, preservatives or buffers, which enhance the shelf life or effectiveness of the antibody. The precise nature of the carrier or other material will depend on the route of administration, which may be oral, topical, by inhalation or by injection, e.g., intravenous. In a preferred embodiment, the antibody is administered by intravenous infusion or injection. In another preferred embodiment, the antibody is administered by intramuscular or subcutaneous injection.

Pharmaceutical compositions for oral administration may be in tablet, capsule, powder or liquid form for example, with an inert diluent or an assimilable edible carrier. A tablet may comprise a solid carrier, such as gelatin or an adjuvant. Liquid pharmaceutical compositions generally comprise a liquid carrier, such as water, petroleum, animal or vegetable oils, mineral oil or synthetic oil. Physiological saline solution, dextrose or other saccharide solution or glycols, such as ethylene glycol, propylene glycol or polyethylene glycol may be included. The antibody (and other ingredients, if desired) can also be enclosed in a hard or soft shell gelatin capsule, compressed into tablets, or incorporated directly into the subject's diet. For oral therapeutic administration, the active ingredient can be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation.

For intravenous injection, or injection at the site of affliction, the active ingredient will be in the form of a parenterally acceptable aqueous solution which is pyrogen-free and has suitable pK, isotonicity and stability. Those of relevant skill in the art are well able to prepare suitable solutions using, for example, isotonic vehicles, such as Sodium Chloride Injection, Ringer's Injection, and/or Lactated Ringer's Injection. Preservatives, stabilisers, buffers, antioxidants and/or other additives may be included, as required.

A composition may be administered alone or in combination with other treatments, either simultaneously or sequentially dependent upon the condition to be treated.

Antibodies may be formulated in liquid, semi-solid or solid forms, such as liquid solutions (e.g., injectable and infusible solutions), dispersions or suspensions, tablets, pills, powders, liposomes and suppositories. The preferred form depends on the intended mode of administration, therapeutic application, the physicochemical properties of the molecule and the route of delivery. Formulations may include excipients, or combinations of excipients, for example: sugars, amino acids and surfactants. Liquid formulations may include a wide range of antibody concentrations and pH. Solid formulations may be produced by, for example, lyophilization, spray drying, or drying by supercritical fluid technology.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating, such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, active compound of the antibody compositions may be prepared with a carrier that will protect the antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems (J. R. Robinson, ed., Marcel Dekker, Inc., New York, 1978).

In various embodiments, other therapeutic regimens may be combined with the administration of an anti-TGF-β antibody. The combined administration includes co-administration, using separate formulations or a single pharmaceutical formulation, and consecutive administration in either order, wherein preferably there is a time period while both (or all) active agents simultaneously exert their biological activities.

For the prevention or treatment of consequences of myocardial infarction, the appropriate dosage of a TGF-β antagonist will depend on the condition of the patient, the severity and course of the infarction, whether the antibody is administered for preventive or therapeutic purposes, previous therapy, the patient's clinical history and response to the antibody, and the discretion of the attending physician. The antagonist may be administered to the patient at one time or over a series of treatments initiating during day 0 (e.g., within about 8, 12 or 24 hours), day 1, day 2, day 3, day 4, or day 5 after an ischemic event, preferably at day 0, day 3, or day 5. That is, in some embodiments, administration of the antagonist of TGF-β is commenced within about 120 hours, about 96 hours, about 72 hours, about 48 hours, within about 24 hours, about 12 hours or even within about 8 or fewer hours of onset of acute myocardial ischemia. Depending on the type and severity of the condition, about 5 mg/kg of antibody is an initial candidate dosage for administration to the patient, whether, for example, by one or more separate administrations, or by continuous infusion post-MI. A typical daily dosage might be equal to 5 mg/kg or less, depending on the factors mentioned above. For repeated administrations over several days or longer, depending on the condition, the treatment is sustained until a desired suppression of disease symptoms occurs. The preferred dosage of the antibody will be 5 mg/kg or less administered intravenously. Thus, one or more doses of about 5 mg/kg or less (or any combination thereof) may be administered to the patient. However, other dosage regimens may be useful. The progress of this therapy is easily monitored by conventional techniques and assays.

Anti-TGF-β antibodies are useful to treat AMI when combined with antagonists of the renin-angiotensin-aldosterone system including but not limited to: renin inhibitors, angiotensin-converting enzyme (ACE) inhibitors, Ang II receptor antagonists (also known as "Ang II receptor blockers"), and aldosterone antagonists. Anti-TGF-β antibodies are also useful to treat AMI when combined with antagonists of the beta-adrenergic system including but not limited to the group consisting of alprenolol, bucindolol, carteolol, carvedilol, labetalol, nadolol, oxprenolol, penbutolol, pindolol, propranolol, sotalol, timolol, atenolol, betaxolol, bisoprolol, celiprolol, esmolol, metoprolol, and nebivolol. Furthermore, anti-TGF-β antibodies are useful to treat AMI when combined with lipid management agents including but not limited to the group of statins consisting of lovastatin, pravastatin, simvastatin, fluvastatin, atorvastatin, cerivastatin, resuvastatin, the group of bile acid sequestrants consisting of chlestyramine, celestipol, colesevalam, the group of fibric acids consisting of gemfibrozil, fenofibrate, clofibrate, the group including nicotinic acid and niaspan, the group including the cholesterol lowering agent ezetimibe and the combination of ezetimibe and simvastatin. In another aspect, anti-TGF-β antibodies are useful to treat AMI when combined with antiplatelet agents/anticoagulants including but not limited to aspirin, the group of ADP receptor inhibitors consisting of clopidogrel, prasugrel, ticagrelor, ticlopidine, and the anticoagulant warfarin.

Therapeutic formulations of antibodies used in treatment may be provided in a container available for intravenous treatment. The formulations may also be prepared for storage by mixing an antibody having the desired degree of purity with optional pharmaceutically-acceptable carriers, excipients, or stabilizers including, but not limited to those in Remington's Pharmaceutical Sciences 16th edition, Osol, A. Ed. (1980) and in the form of lyophilized formulations or aqueous solutions. Acceptable carriers, excipients, or stabilizers are nontoxic to recipients at the dosages and concentrations employed, and include buffers, such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low-molecular-weight (less than about 10 residues) polypeptides; proteins, such as serum albumin, gelatin, or immunoglobulins; hydrophilic polymers, such as polyvinylpyrrolidone; amino acids, such as glycine, glutamine, asparagine, histidine, arginine, or lysine; monosaccharides, disaccharides, and other carbohydrates including glucose, mannose, or dextrins; chelating agents, such as EDTA; sugars, such as sucrose, mannitol, trehalose or sorbitol; salt-forming counter-ions, such as sodium; metal complexes; and/or non-ionic surfactants.

The formulation may also contain more than one active compound as necessary for the particular indication being treated. Preferably, the compounds with complementary activities do not adversely affect each other. Alternatively, or additionally, the composition may further comprise a cytokine, growth-inhibitory agent, anti-hormonal agent, TGF-β-targeted drug, anti-angiogenic agent, and/or cardioprotectant. Such molecules are suitably present in combination in amounts that are effective for the purpose intended.

"Cytokine" is a generic term for proteins released by one cell population that act on another cell as intercellular mediators. Examples of such cytokines are lymphokines, monokines, and traditional polypeptide hormones. Included among the cytokines are growth hormone, such as human growth hormone, N-methionyl human growth hormone, and bovine growth hormone; parathyroid hormone; thyroxine; insulin; proinsulin; relaxin; prorelaxin; glycoprotein hormones, such as follicle-stimulating hormone (FSH), thyroid-stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors, such as NGF-.β.; platelet-growth factor; insulin-like growth factor-I and -II; erythropoietin (EPO); osteoinductive factors; interferons, such as interferon-α, β, and -γ; colony-stimulating factors (CSFs), such as macrophage-CSF (M-CSF); granulocyte-macrophage-CSF (GM-CSF); and granulocyte-CSF (G-CSF); interleukins (ILs), such as IL-1, IL-1α, IL-2, IL-3, IL-4, IL-5, IL-6, IL-7, IL-8, IL-9, IL-10, IL-11, IL-12; a tumor necrosis factor, such as TNF-α or TNF-β; and other polypeptide factors including LIF and kit ligand (KL). As used herein, the term cytokine includes proteins from natural sources or from recombinant cell culture and biologically active equivalents of the native-sequence cytokines.

A "cardioprotectant" is a compound or composition that prevents or reduces myocardial dysfunction (i e., cardiomyopathy and/or congestive heart failure) associated with administration of a drug, such as an anti-TGF-β antibody, to a patient. The cardioprotectant may, for example, block or reduce a free-radical-mediated cardiotoxic effect and/or prevent or reduce oxidative-stress injury.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug-delivery systems (for example, liposomes, albumin microspheres, microemulsions, nano-particles and nanocapsules) or in macroemulsions. These techniques are disclosed in Remington's Pharmaceutical Sciences 16th edition, Osol, A. Ed. (1980).

Sustained-release preparations may be prepared. Suitable examples of sustained-release preparations may include semipermeable matrices of solid hydrophobic polymers containing the antibody, which matrices are in the form of shaped articles, e.g., films, or microcapsules. Examples of sustained-release matrices include but are not limited to, polyesters, hydrogels (for example, poly(2-hydroxyethyl-methacrylate), or poly(vinylalcohol)), polylactides, copolymers of L-glutamic acid and γ ethyl-L-glutamate, non-degradable ethylene-vinyl acetate, degradable lactic acid-glycolic acid copolymers, and poly-D-(−)-3-hydroxybutyric acid. The formulations to be used for in vivo administration must be sterile. This is readily accomplished by filtration through sterile filtration membranes.

An article of manufacture containing materials useful for the treatment of the MI as described above may be provided, generally comprising a container and a label or package insert on or associated with the container. A "package insert" comprises instructions customarily included in commercial packages of therapeutic products, that contain information about the indications, usage, dosage, administration, contraindications, and/or warnings concerning the use of such therapeutic products.

Suitable containers include, but are not limited to, bottles, vials, IV solution bags, vessels, syringes, etc. The containers may be formed from a variety of materials, such as glass or plastic. The container holds a composition that is effective for inhibition of TGF-β signaling and may have a sterile access port (for example, the container may be an intravenous solution bag or a vial having a stopper pierceable by a hypodermic injection needle). At least one active ingredient in the composition may be an anti-TGF-β antibody. The label or package insert may indicate that the composition is used for treating myocardial infarction, acute myocardial infarction, or the reduction of a consequence of myocardial infarction, In one embodiment, the label or package insert indicates that the composition comprising the antibody can be administered during the acute phase of a myocardial infarction.

Furthermore, the article of manufacture may comprise a container comprising a composition of an anti-TGF-β antibody, and a therapeutic agent other than the antibody. The article of manufacture may further comprise a package insert indicating that the first and second compositions can be used in combination to treat a myocardial infarction. This therapeutic agent may be any of the adjunct therapies described in the preceding section (e.g., an anti-angiogenic agent, an anti-hormonal compound, a cardioprotectant, and/or a regulator of immune function in a mammal, including a cytokine). Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

As a matter of convenience, anti-TGF-β antibodies can be provided in a kit, i.e., a packaged combination of reagents in predetermined amounts with instructions. In addition, other additives may be included, such as stabilizers, buffers (e.g., a block buffer or lysis buffer). Particularly, the antibodies may be provided as dry powders, usually lyophilized, including excipients that on dissolution will provide a solution having the appropriate concentration.

In addition to the methods described in the summary and detailed description above, the following embodiments are also among those contemplated. A method of treating a patient suffering from myocardial infarction, acute myocardial infarction or of reducing adverse consequences of an acute myocardial infarction in a patient may comprise administering an antagonist of TGF-β to a patient during the acute stage of the myocardial infarction. The TGF-β antagonist may be selected from a group consisting of: an antibody or protein comprising an antibody fragment directed against one or more isoforms of TGF-β; a TGF-β receptor; an antibody or protein comprising an antibody fragment directed against one or more TGF-β receptors; latency associated peptide; large latent TGF-β, a TGF-β inhibiting proteoglycan; somatostatin; mannose-6-phosphate; mannose-1-phosphate; prolactin; insulin-like growth factor II; IP-10; an arg-gly-asp containing peptide; a plant, fungal, or bacterial extract; an antisense or interfering RNA oligonucleotide; and a protein involved in TGF-β signaling.

In preferred embodiments, the antagonist of TGF-β is a humanized anti-TGF-β antibody or a fragment or antigen-binding site of an anti-TGF-β antibody. The TGF-β antagonist may be an antibody or antibody fragment capable of binding and neutralizing more than one isoform of TGF-β. The antibody may be a chimeric monoclonal antibody comprising a TGF-β binding portion and a remainder portion, said TGF-β binding portion comprising the antigen-binding portion of monoclonal antibody 1D11.16, and the remainder portion derived from one or more human antibodies. An antibody that is directed against more than one isoform of TGF-β may be a human or humanized form of monoclonal antibody 1D11.16, The antagonist of TGF-β may be an antibody or antibody fragment that neutralizes human TGF-β1, TGF-β2 and TGF-β3

The administration of the antagonist of TGF-β may be commenced within about 120, about 80, about 72, about 48, or about 24 hours of onset of acute myocardial ischemia. In some instances, administration of the antagonist of TGF-β is commenced within about 12 hours of onset of acute myocardial ischemia. Administration of the antagonist of TGF-β may be commenced prior to substantial macrophage and mononuclear infiltration of tissue affected by the myocardial infarction. In other instances, administration of the antagonist of TGF-β is commenced during a period characterized by neutrophilic infiltration of tissue affected by the myocardial infarction. Further, in some instances administration of the antagonist of TGF-β is commenced during a period characterized by necrosis of tissue affected by the myocardial infarction.

The method can also comprise administering a compound capable of selectively restoring a desirable function of TGF-β to a patient diagnosed with an acute myocardial infarction during the acute stage of the myocardial infarction, for example, an anti-inflammatory drug and/or an antagonist of TNF-α. The method may be used in human and veterinary medicine so that the patient may be a human or a non-human mammal.

With respect to the antagonist of TGF-β, in some embodiments the antagonist is an antibody that neutralizes human TGF-β1, TGF-β2 and TGF-β3, and comprises an antigen-binding domain of an antibody, wherein said antigen-binding domain comprises a set of CDRs HCDR1, HCDR2 and HCDR3, and wherein said antigen-binding domain utilizes a human VH1 family gene and wherein said HCDR3 has an amino acid sequence selected from the group consisting of SEQ ID NO: 5, SEQ ID NO: 15 and SEQ ID NO: 25. The human VH1 family gene can be a human VH1-2 gene, which in some instances may be a DP-10 or a DP-88 gene. The antigen-binding domain may further comprise a set of CDRs LCDR1, LCDR2 and LCDR3, and wherein said antigen-binding domain utilizes a human $V_\kappa 3$ family gene and wherein said LCDR3 has an amino acid sequence selected from the group consisting of SEQ ID NO: 10, SEQ ID NO: 20 and SEQ ID NO: 30. The HCDR3 and LCDR3 can be selected from the group consisting of: (a) SEQ ID NO: 5 and SEQ ID NO: 10, respectively; (b) SEQ ID NO: 15 and SEQ ID NO: 20, respectively; and (c) SEQ ID NO: 25 and SEQ ID NO: 30, respectively.

In some embodiments, the human $V_\kappa 3$ family gene may be a human VK DPK22 gene. The HCDR1, HCDR2 and HCDR3 of the VH domain may be comprised within a germline heavy chain framework, or the HCDR1, HCDR2 and HCDR3 of the VH domain are within a framework that comprises up to 12 mutations from the germline amino acid sequence. The LCDR1, LCDR2 and LCDR3 of the VK domain may be comprised within a germline heavy chain framework. In some instances, the LCDR1, LCDR2 and LCDR3 of the VK domain may be within a framework that comprises up to 5 mutations from the germline VK amino acid sequence.

The antagonist of TGF-β may be an antibody that neutralizes human TGF-β1, TGF-β2 and TGF-β3, and comprises an antigen-binding domain of an antibody, wherein said antigen-binding domain utilizes a human VH DP-10 gene or a human VH DP-88 gene and comprises an FR4 amino acid sequence comprising the amino acid sequence in SEQ ID NO: 31, The antigen-binding domain may utilize a human VH DP-10 gene or a human VH DP-88 gene, and comprises a set of CDRs HCDR1, HCDR2 and HCDR3, wherein said HCDR3 has an amino acid sequence selected from the group consisting of SEQ ID NO: 5, SEQ ID NO: 15 and SEQ ID NO: 25, and further comprises an FR4 amino acid sequence comprising the amino acid sequence in SEQ ID NO: 31. The antigen-binding domain may further utilize a human $V_\kappa 3$ family gene and a human $J_\kappa 5$ gene. An antigen-binding domain utilizing a human $V_\kappa 3$ family gene and a human $J_\kappa 5$ gene may comprise a set of CDRs LCDR1, LCDR2 and LCDR3, wherein said LCDR3 has an amino acid sequence selected from the group consisting of SEQ ID NO: 10, SEQ ID NO: 20 and SEQ ID NO: 30.

In some embodiments, the antagonist of TGF-β neutralizes human TGF-β1, TGF-β2 and TGF-β3, and comprises an antigen-binding domain of an antibody, wherein said antigen-binding domain comprises: (a) the HCDR1 of amino acid sequence of SEQ ID NO: 3, HCDR2 of amino acid sequence of SEQ ID NO: 4, HCDR3 of amino acid sequence of SEQ ID NO: 5; (b) the HCDR1 of amino acid sequence of SEQ ID NO: 13, HCDR2 of amino acid sequence of SEQ ID NO: 14, HCDR3 of amino acid sequence of SEQ ID NO: 15; or (c) the HCDR1 of amino acid sequence of SEQ ID NO: 23, HCDR2 of amino acid sequence of SEQ ID NO: 24, HCDR3 of amino acid sequence of SEQ ID NO: 25. The antigen-binding domain may further comprise an antibody VL domain. The antigen-binding domain may comprise LCDRs selected from the group consisting of: (a) the LCDR1 of amino acid sequence of SEQ ID NO: 8, LCDR2 of amino acid sequence of SEQ ID NO: 9, LCDR3 of amino acid sequence of SEQ ID NO: 10; (b) the LCDR1 of amino acid sequence of SEQ ID NO: 18, LCDR2 of amino acid sequence of SEQ ID NO: 19, LCDR3 of amino acid sequence of SEQ ID NO: 20; and (c) the LCDR1 of amino acid sequence of SEQ ID NO: 28, LCDR2 of amino acid sequence of SEQ ID NO: 29, LCDR3 of amino acid sequence of SEQ ID NO: 30. In some instances, the HCDR1, HCDR2 and HCDR3 of the VH domain may be comprised within a germline heavy chain framework, for example, a human VH1 family framework. The HCDR1, HCDR2 and HCDR3 of the VH domain may be within germline human heavy chain framework VH1 DP-10 or DP-88. The LCDR1, LCDR2 and LCDR3 of the VL domain may be within a germline light chain framework. The germline light chain framework may be a human $V_\kappa 3$ family framework. The antigen-binding domain may further comprise a human $J_\kappa 5$ gene. The human $V_\kappa 3$ family gene may be a $V_\kappa$ DPK22 gene.

In some variations, the antagonist of TGF-β may be an antibody comprising the PET1073G12 VH domain (SEQ ID NO: 2) with up to 5 mutations, or an antigen-binding portion thereof. The antagonist of TGF-β may be an antibody comprising the PET1074B9 VH domain (SEQ ID NO: 12) with up to 5 mutations, or an antigen-binding portion thereof. The antagonist of TGF-β may be an antibody comprising the PET1287A10 VH domain (SEQ ID NO: 22) with up to 5 mutations, or an antigen-binding portion thereof. The antagonist of TGF-β may be an antibody comprising the PET1073G12 VL domain (SEQ ID NO: 7) with up to 5 mutations, or an antigen-binding portion thereof. The antagonist of TGF-β may be an antibody comprising the PET1074B9 VL domain (SEQ ID NO: 17) with up to 5 mutations, or an antigen-binding portion thereof. The antagonist of TGF-β may be an antibody comprising the PET1287A10 VL domain (SEQ ID NO: 27) with up to 5 mutations, or an antigen-binding portion thereof. The antagonist of TGF-β may be an antibody comprising the PET 1073G12 VH domain (SEQ ID NO: 2) and the PET 1073G12 VL domain (SEQ ID NO: 7). The antagonist of TGF-β may be an antibody comprising the PET 1074B9 VH domain (SEQ ID NO: 12) and the PET 1074B9 VL domain (SEQ ID NO: 17). Alternatively, the antagonist of TGF-β may be an antibody comprising the PET 1287A10 VH domain (SEQ ID NO: 22) and the PET 1287A10 VL domain (SEQ ID NO: 27). Further variations as described herein are also contemplated.

The SEQ ID NOs refer to the sequences found in the attached sequence listing, which forms part of this disclosure. While the methods have been described in detail with reference to certain embodiments thereof, it will be apparent to one skilled in the art that various changes can be made, and equivalents employed, without departing from the scope of this disclosure or the claims which follow. Moreover, the following examples are presented as illustrations of aspects of the methods and should not be construed as limiting.

Example 1—Antibody Purification

Monoclonal antibodies 1D11 and GC 1008 were purified either from culture supernatant or ascites by protein A-Sepharose chromatography (Goding, J Immunol Meth (1976) 42; 17) (Pharmacia Fien Chemicals, Uppsala, Sweden). The binding of the gamma (γ)1 subclass and gamma (γ)4 subclass monoclonal antibodies, 1D11 and GC 1008, to protein A were enhanced by addition of a commercially prepared binding buffer (BioRad, Richmond, Calif.). Antibodies were eluted from the protein A-Sepharose with 0.05 M glycine-HCl plus 0.15 M NaCl buffer (pH 2.3), dialyzed overnight versus PBS and NaCl buffer (pH 2.3), dialyzed overnight versus PBS and stored at −20 degrees Celsius. The gamma (γ) 1 and gamma (γ) 4 subclass antibodies purified from supernatants were concentrated and partially purified by ammonium sulfate precipitation (50% saturated) prior to protein A-chromatography.

Example 2—Effect of a TGF-β Inhibitor in a Rat Model of Cardiac Ischemia Reperfusion Twelve to fourteen-week-old female Lewis rats were assigned to five treatment groups. At day 0 (D0), all animals underwent a cardiac ischemia followed by reperfusion procedure (I/R). The cardiac ischemia was created by temporarily ligating the left anterior descending coronary artery on the left ventricle of the heart for 60 minutes. The ligation was then released allowing for reperfusion of the ischemic part of the heart. Starting 3 or 5 days post I/R, 5 mg/kg of 1D11 or control article (negative-control antibody 13C4 or vehicle) was administered by intravenous (IV) injection, and then readministered every third day until day 28.

In order to analyze the area at risk (AAR), 15 μm diameter microspheres labeled with a yellow fluorochrome and were injected into the left ventricle of the heart immediately before releasing the temporary ligation of the left descending coronary artery (D0). The microspheres distributed homogenously in the blood and lodged in capillaries of the heart and other organs and tissues. The AAR in the heart was defined as the area of the myocardial tissue that did not receive any microspheres (or blood) during the ligation period. At day 28 the animal was lightly anesthetized with isoflurane and the heart rate was maintained at 350±50 bpm. An echocardiograph was then performed in the long axis view in order to assess regional and global cardiac function. Following the echocardiography examination, the animal was euthanized with an overdose of sodium pentobarbital. The heart was then excised for histological analysis.

The AAR was assessed and subsequently assigned a qualitative score. Animals with small AAR (<~20% of the LV) or no AAR were removed from study analysis Cardiac fibrosis in the LV was assessed histologically and using heart weight and expressed as a percentage of fibrosis weight/total LV weight. Regional cardiac function was then assessed by an evaluation of the anterior wall thickening (AWT) and as compared to the posterior wall thickening (PWT) in the area at risk. Wall thickening is the difference in the wall thickness at systole and the wall thickness at diastole. Global function was also assessed by evaluation of ejection fraction (EF) and fractional shortening (FS).

Daily visual clinical observations were unremarkable throughout the study duration. In FIG. 1, 1D11 administration markedly reduced the percentage of fibrosis in the LV in comparison to the vehicle and the negative-control antibody, 13C4. This decrease in fibrosis occurred whether 1D11 treatment began 3 days after I/R (D3) [1D11-D3] or 5 days after I/R (D5) [1D11-D5]. The group that began treatment of 1D11 at D5 reached statistical significance ($P<0.05$) as compared to the control 13C4-treated group.

Cardiac function parameters were assessed by echocardiography at 4 weeks following I/R, as seen in Table 1. Ejection fraction and fractional shortening represent global cardiac function. AWT, PWT and AWT/PWT (regional wall motion score) represent regional cardiac function. In the normal rodent, AWT is approximately equal to, and can be greater than, PWT. It follows then that the ratio of AWT/PWT, what we have termed regional wall motion score, in a normal animal would be ≥1. In Table 1, the normal animal group showed AWT greater than PWT, and regional wall motion score (AWT/PWT) of 1.7±0.2.

TABLE 1

| 4 Week Echocardigraphy Results | | | | | |
|---|---|---|---|---|---|
| | Vehicle | 1D11-D3 | 1D11-D5 | 13C4 | Normal |
| Ejection Fraction (%) | 61.3 ± 3.4 | 57.1 ± 2.9 | 59.9 ± 3.8 | 66.3 ± 2.7 | 83.9 ± 0.7 |
| Fractional Shortening (%) | 27.7 ± 2.0 | 24.9 ± 1.7 | 27.1 ± 2.3 | 30.9 ± 2.0 | 45.9 ± 0.7 |
| AWT(cm) | 0.04 ± 0.01 | 0.06 ± 0.01 | 0.07 ± 0.13 | 0.07 ± 0.01 | 0.12 ± 0.004 |
| PWT(cm) | 0.097 ± 0.01 | 0.08 ± 0.01+ | 0.07 ± 0.01+ | 0.1 ± 0.01 | 0.09 ± 0.004 |
| AWT/PWT | 0.51 ± 0.2 | 0.91 ± 0.20 | 1.01 ± 0.15 | 0.7 ± 0.1 | 1.7 ± 0.2 |

+p < 0.05 vs. 13C4

Figure 2:
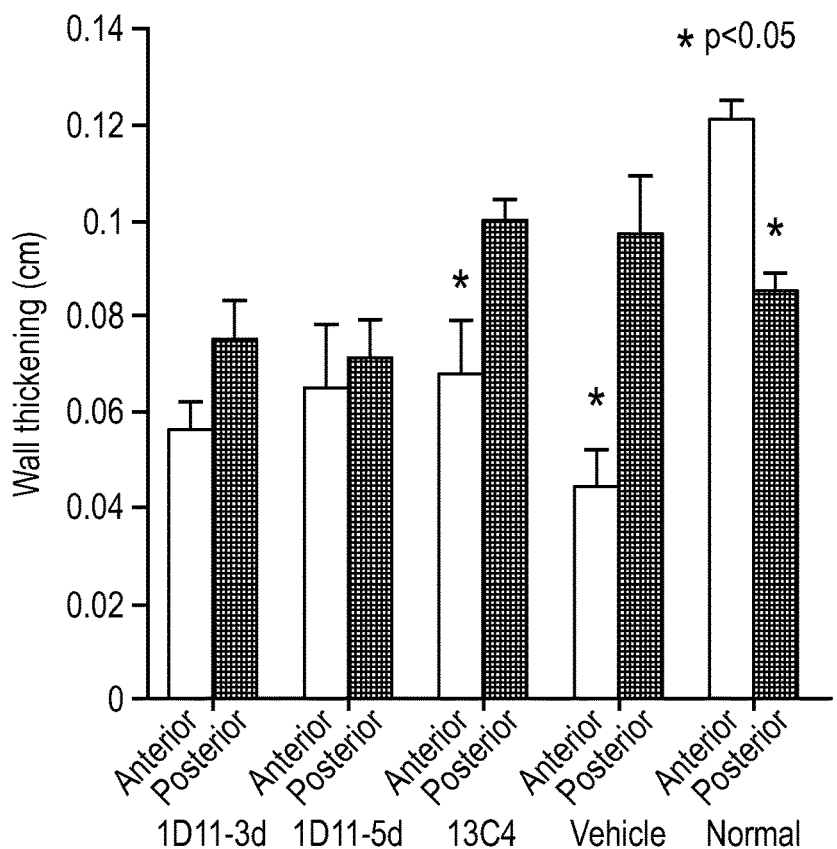
FIG. 2 shows anterior wall thickening and posterior wall thickening in an echocardiogram analysis.
Figure 3:
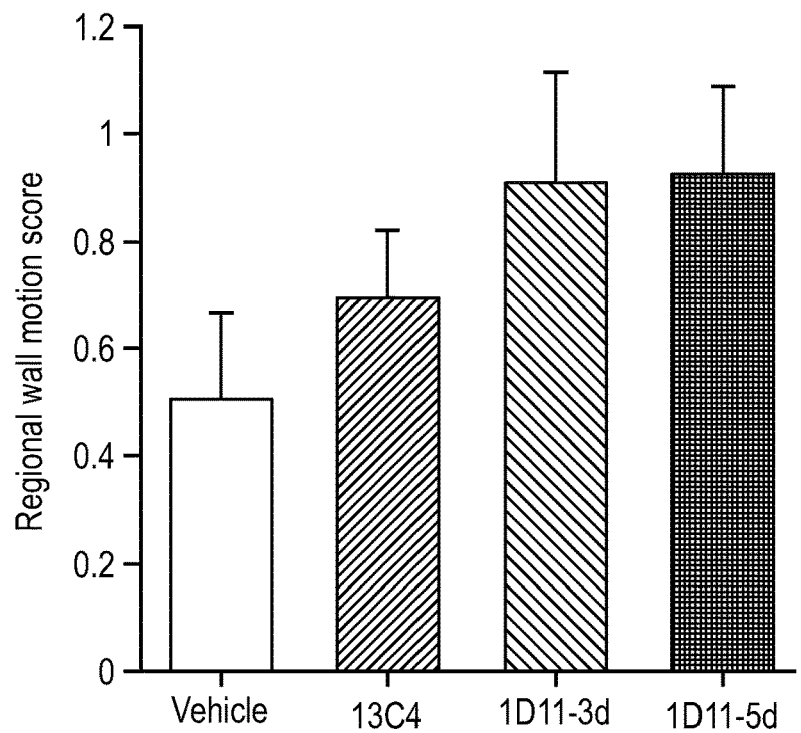
FIG. 3 shows a regional wall motion score in an echocardiogram analysis.

At 4 weeks following I/R, cardiac function in all groups that underwent I/R was less than that observed in the normal animal group. AWT and PWT were similar in the 1D11-D3 and 1D11-D5 groups (Table 1 and FIG. 2) and regional wall motion scores were 0.91±0.2 and 1.01±0.15 in the 1D11-D3 and 1D11-D5 groups, respectively (Table 1 and FIG. 3). It was further noted that the regional wall motion scores were compatible with minimal impairment in regional function as compared to a normal animal value of ≥1. In contrast, AWT is markedly less than PWT in the negative-control 13C4 and vehicle groups (Table 1 and FIG. 2) and regional wall motion scores were 0.7±0.1 and 0.51±0.2 in the 13C4 and vehicle groups, respectively, compatible with significant impairment as compared to the 1D11-treated groups and normal animals. Notably, the relative lack of impairment in regional cardiac function in the 1D11-treated groups was consistent with the reductions in fibrosis observed in these groups as compared to the vehicle and negative-control antibody 13C4 groups.

Although regional function in the 1D11-treated groups was improved as compared to the vehicle and 13C4 groups, ejection fraction and fractional shortening were similar between these groups. This is likely attributable to compensation in function of the LV that was not infarcted in the 13C4 and vehicle groups. The increase in PWT, compatible with hypertrophy, observed in these groups is consistent with this interpretation, This example allowed for the evaluation of whether initiation of TGF-β antagonism at either day 3 or day 5 following I/R would result in reduced fibrosis in the infarct and improved cardiac function. There was a marked reduction in the percentage of fibrosis in the LV in both 1D11-treated groups as compared to vehicle and 13C4-treated groups. While the level of fibrosis in 1D11-D3 and 1D11-D5 groups were similar, the 1D11-D5 group reached statistical significance as compared to the negative-control 13C4 group (p<0.05). It has been shown in MI models that the development of fibrosis post-MI is associated with upregulation of TGF-β, TGF-β signaling through the smad pathway and TGF-β regulated genes. Administration of 1D11 in rodent cardiac I/R model blunts the upregulation of TGF-β and TGF-β associated genes following I/R, including collagen 3 and fibronectin which are associated with fibrosis. The observed reduction in fibrosis with 1D11 administration is consistent with 1D11 blunting of TGF-β mediated fibrosis in this model.

The reduction in fibrosis in the 1D11-treated groups corresponded with minimal impairments in cardiac regional function, whereas the negative-control, 13C4, and vehicle groups showed marked impairment in regional function. AWT, PWT, and regional wall motion scores, were similar in both 1D11-D3 and 1D11-5 groups. This suggests that the reduction in fibrosis in 1D11-treated animals resulted in sparing or salvaging of myocardium which contributed to sparing of regional cardiac function following MI. While 1D11-treated groups had improved regional function as compared to the 13C4 and vehicle groups, ejection fraction and fractional shortening were similar between groups. This is consistent with the ability of the heart to functionally compensate for the impairment in regional function in the 13C4 and vehicle groups. The end point of this study was 28 days after I/R. It is possible that compensation in the 13C4 and vehicle groups would not be maintained over a long term in this model, and differences in global function between 1D11, 13C4 and vehicle treated animals would become apparent over long term.

1D11-mediated TGF-β antagonism beginning at either day 3 or day 5 post I/R resulted in reductions in cardiac fibrosis which reached significance in the 1D11-D5 group. The reductions in fibrosis corresponded with improved regional cardiac function as compared to animals that received the negative-control antibody, 13C4, or vehicle, and suggested sparing or salvage of myocardium in the 1D11-treated animals.

Example 3 Effect of Timing of Administration of a TGF-β Inhibitor in a Rat Model of Cardiac Ischemia Reperfusion The effect of different timing of administration of 1D11, a TGF-β inhibitor antibody, on myocardial fibrosis in a rat model of cardiac ischemia followed by reperfusion (I/R) was observed. 1D11 administration was initiated at either 0, 1 or 5 days after cardiac I/R. The effect of a reduction in myocardial fibrosis resulted in improved heart function as measured by echocardiography.

Twelve to fourteen week old female Lewis rats were assigned to seven different treatment groups. All animals underwent a cardiac ischemia followed by a reperfusion procedure (I/R). Cardiac ischemia was created by temporarily ligating the left anterior descending coronary artery on the left ventricle of the heart for 60 minutes. The ligation was then released allowing for reperfusion of the ischemic part of the heart, Starting 0 (2 hours post-reperfusion), 1 or 5 days post I/R, 5 mg/kg of 1D11 or control article (negative-control antibody 13C4 or vehicle) was administered by intravenous (IV) injection, and then readministered every 3rd day until day 28, In order to analyze the area at risk, 15 micron diameter microspheres were labeled with a yellow fluorochrome and were then injected into the LV of the heart. This was done immediately before releasing the temporary ligation of the left descending coronary artery. The microspheres distributed homogenously in the blood and lodged in capillaries of the heart, and other organs and tissues. The AAR in the heart was defined as the area of the myocardial tissue that did not receive any microspheres (or blood) during the ligation period.

At day 28, the animal was lightly anesthetized with isoflurane and the heart rate was maintained at 350±50 bpm. Echocardiography was then performed in the long axis view for regional and global cardiac function. Following the echocardiography examination, the animal was euthanized with an overdose of sodium pentobarbital. The heart was then excised, weighed and then processed for histological analysis. The AAR was assigned a qualitative score. Animals with small AAR (<~20% of the LV) or no AAR were removed from study analysis Cardiac fibrosis in the LV was assessed histologically and using heart weight and expressed as a percentage of fibrosis weight/total LV weight. Regional cardiac function was assessed by evaluation of the anterior wall thickening (AWT) as compared to posterior wall thickening (PWT) in the area at risk. Wall thickening is the difference in the wall thickness at systole and the wall thickness at diastole. Global function was assessed by evaluation of ejection fraction (EF) and fractional shortening (FS).

Figure 4:
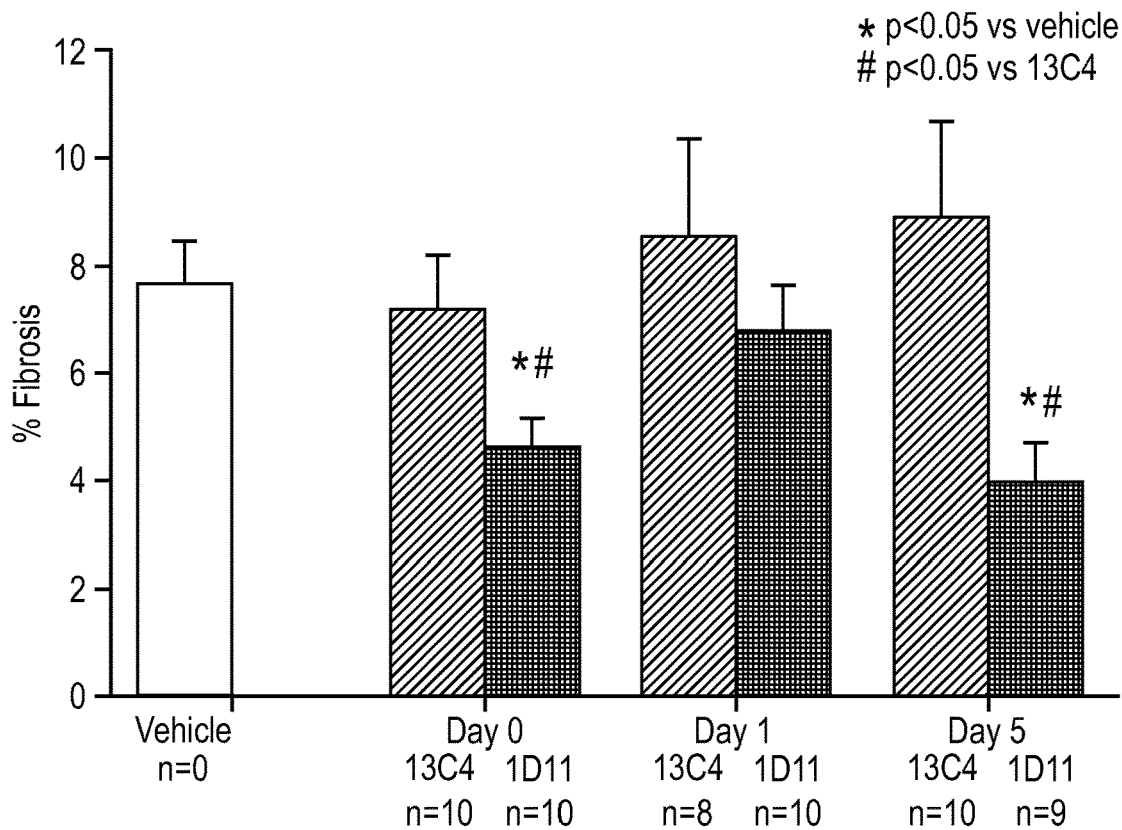
FIG. 4 shows a reduction in fibrosis with administration of 1D11 and 13C4.

1D11 administration starting at either day 0 or day 5 significantly reduced the percentage of fibrosis in the LV as compared to the vehicle and negative-control antibody, 13C4-treated groups (FIG. 4). 1D11 administration beginning at D1 showed a trend for reduction in fibrosis as compared to matched 13C4 or vehicle control.

Table 2 shows cardiac function parameters that were assessed by echocardiography at 4 weeks following I/R. The ejection fraction and fractional shortening represent global cardiac function. AWT, PWT and AWT/PWT (regional wall motion score) represent regional cardiac function. In the normal rodent, AWT is approximately equal to, and can be greater than, PWT. It follows then that the ratio of AWT/PWT, what we have termed regional wall motion score, in a normal animal would be ≥1. In table 2, the normal animal group showed AWT greater than PWT, and regional wall motion score (AWT/PWT) of 1.7±0.2.

and compatible with significant impairment as compared to the 1D11-treated groups and normal animals. The relative lack of impairment in regional cardiac function in the 1D11-treated groups was consistent with the reductions in fibrosis observed in these groups as compared to the vehicle and matched negative-control antibody 13C4 groups.

The 1D11-D5 group also showed significant improvements in the global cardiac function parameters of ejection fraction and fractional shortening as compared to the vehicle control (Table 2), which is consistent with the fibrosis and regional cardiac function assessments. However, the other 1D11-treated groups did not demonstrate changes in global function as compared to the vehicle and matched 13C4 groups. Reduction in fibrosis with relative lack of impairment in regional function in 1D11-treated animals without significant improvements in global cardiac function was also observed in a previous study and is likely attributable to compensation in function of the LV that was not infarcted in the matched 13C4 and vehicle groups making it difficult to detect changes between the groups at this time point. The increase in PWT, compatible with hypertrophy, observed in these groups is consistent with this interpretation.

This example compared the bioactivity of the anti-TGF-β antibody, 1D11, starting at different time points post-myocardial infarction in a rat model of myocardial infarction where animals underwent cardiac ischemia followed by reperfusion. It is possible that TGF-β plays different roles in the repair response at D0, D1 and at D5, and that TGF-β antagonism initiating at these different time points results in a differential response. The 1D11-D1 group showed trends towards reduction in fibrosis and improvement in cardiac function.

1D11-mediated TGF-β antagonism beginning at either day 0, day 1, or day 5 post I/R resulted in reductions in cardiac fibrosis which reached significance in the 1D11-D0 and 1D11-D5 group as compared to vehicle and matched

TABLE 2

4 Week Echocardiography Results

| | EF (%) | FS (%) | AWT(cm) | PWT(cm) | AWT/PWT |
|---|---|---|---|---|---|
| Vehicle | 50.5 ± 2.6 | 21.1 ± 1.4 | 0.03 ± 0.01 | 0.06 ± 0.01$ | 0.6 ± 0.13+ |
| 1D11-D0 | 51.2 ± 2.9 | 21.5 ± 1.5 | 0.06 ± 0.01*+ | 0.04 ± 0.01* | 1.38 ± 0.2* |
| 1D11-D1 | 52.3 ± 3.3 | 22.3 ± 1.9 | 0.05 ± 0.01* | 0.07 ± 0.01$ | 0.79 ± 0.1 |
| 1D11-D5 | 59.2 ± 2.7* | 26.1 ± 1.7* | 0.06 ± 0.01*+ | 0.06 ± 0.01 | 0.92 ± 0.18 |
| 13C4-D0 | 48.4 ± 1.1 | 19.8 ± 0.6 | 0.04 ± 0.01 | 0.06 ± 0.01$ | 0.52 ± 0.08 |
| 13C4-D1 | 53.0 ± 2.9 | 22.5 ± 1.6 | 0.04 ± 0.01 | 0.06 ± 0.01 | 0.58 ± 0.19 |
| 13C4-D5 | 52.9 ± 2.3 | 22.3 ± 1.2 | 0.04 ± 0.01 | 0.08 ± 0.01$ | 0.54 ± 0.12 |
| Normal | 83.9 ± 0.7 | 45.9 ± 0.7 | 0.12 ± 0.004 | 0.09 ± 0.004 | 1.7 ± 0.2 |

*$p < 0.05$ vs. vehicle,
+$p < 0.05$ vs. 13C4,
$$p < 0.05$ AWT vs PWT

Figure 5:
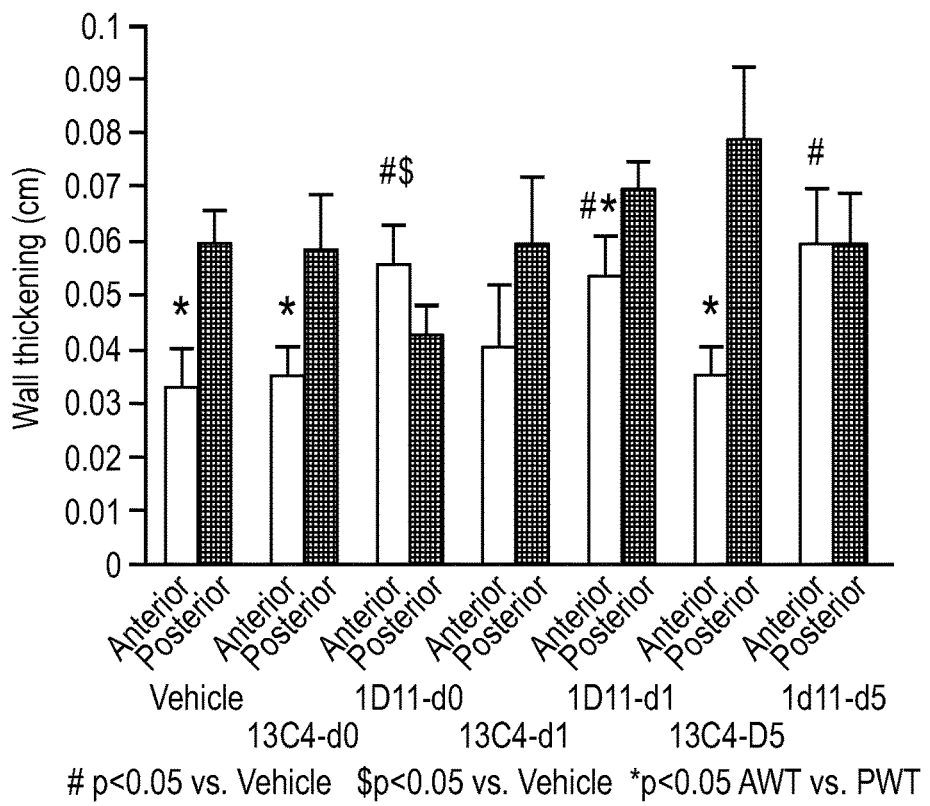
FIG. 5 shows anterior wall thickening and posterior wall thickening in an echocardiogram analysis for 13C4-D0, 1D11-D0, 13C4-D1, 1D11-D1, 13C4-D5 and 1D11-D5 treated groups.

At four weeks following I/R, cardiac function in all groups that underwent I/R was less than that observed in the normal animal group. AWT and PWT were similar in the 1D11-D0, 1D11-D3 and 1D11-D5 groups (Table 2 and FIG. 5). Regional wall motion scores were 1.38±0.2, 0.79±0.1 and 0.92±0.18 in the 1D11-D0, 1D11-D1 and 1D11-D5 groups, respectively (Table 2 and FIG. 3). The regional wall motion scores were compatible with minimal impairment in regional function as compared to a normal animal value of ≥1. In contrast, AWT is markedly less than PWT in the negative-control 13C4 and vehicle groups (Table 2 and FIG. 5). Regional wall motion scores were 0.52±0.08, 0.58±0.19, 0.54±0.12 and 0.6±0.13 in the 13C4-D0, 13C4-D1, 13C4-D5 and vehicle groups, respectively (Table 2 and FIG. 6), 13C4 control antibody groups. In the 1D11-D0 and 1D11-D5 groups, the reductions in fibrosis corresponded with significantly improved regional cardiac function as compared to animals that received the negative-control antibody, 13C4, or vehicle, as well as significantly improved global cardiac function as compared to the vehicle control in the 1D11-D5 group. These results suggested sparing or salvage of myocardium in the 1D11-treated animals.

Example 4—Effects of TGF-B Inhibitor, 1D11, in a Rodent Model of Myocardial Remodeling Following Myocardial Ischemia Administration of 1D11, a TGF-β inhibitor, reduced the development of fibrosis and subsequently improved cardiac function in a dose-dependent manner. On Day 0, the left ascending coronary artery was ligated for 60 minutes (coronary artery occlusion or CAO) and then released to allow for reperfusion (coronary artery reperfusion or CAR). At day 5, vehicle, 1D11 and 13C4 (control antibody) were administrated via IV and continued every 3 days until sacrifice on day 28 (week 4). Echocardiography was performed at 2 weeks and 4 weeks following CAR in order to determine left ventricular function. At 4 weeks after CAR, a terminal surgical procedure was performed to directly measure LV function using pressure-volume (PV) hemodynamics. A dobutamine stress test was also performed. After completing all of the above procedures, the rats were euthanized, and myocardial tissues from ischemic and non-ischemic zones were collected for pathological analysis. A subgroup of nine rats was used for the assessment of infarct size was and euthanized at seven days after CAO/CAR. The hearts were then perfused and stained. The area at risk and infarct size were measured and compared between the vehicle and 1D11 (25 mg/kg) groups.

Figure 6:
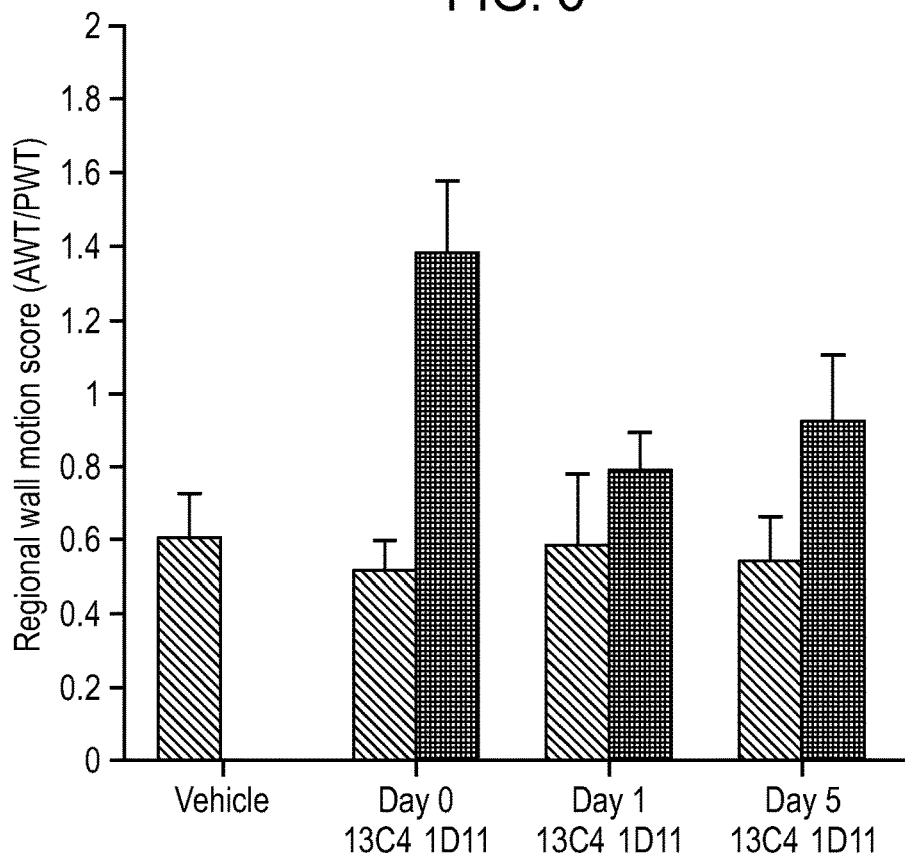
FIG. 6 shows a regional wall motion score in an echocardiogram analysis for vehicle, 13C4-D0, 1D11-D0, 13C4-D1, 1D11-D1, 13C4-D5 and 1D11-D5 treated groups.
Figure 7:
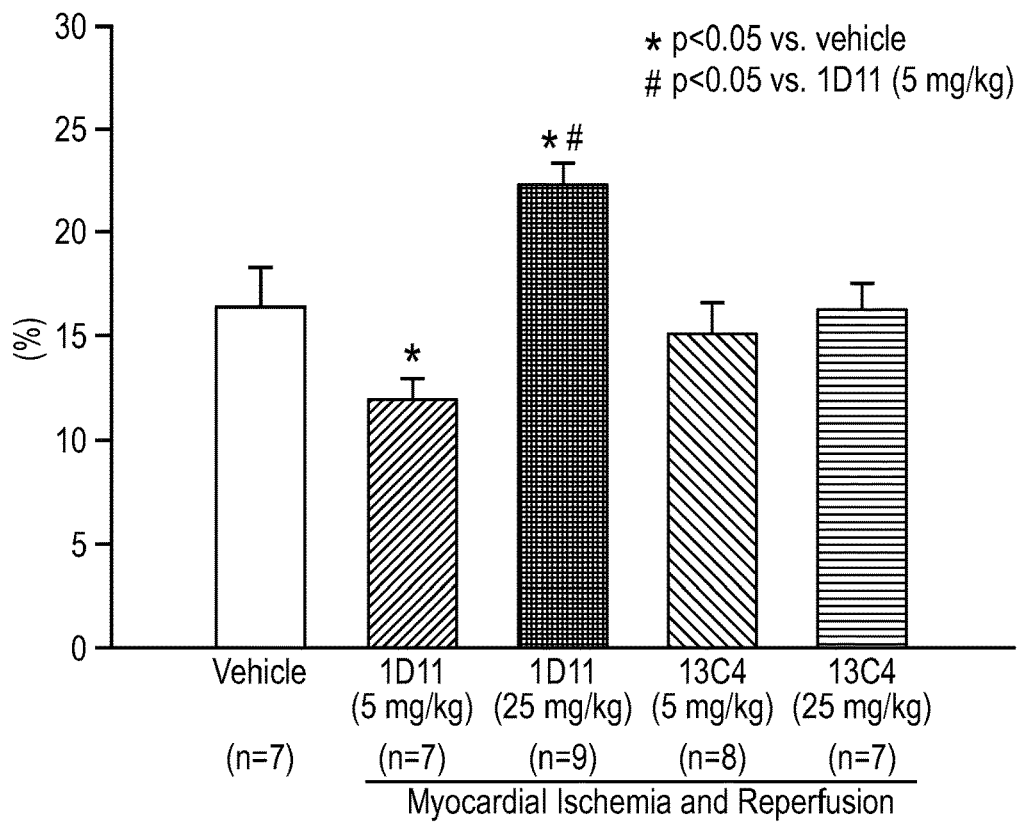
FIG. 7 shows LV scar volume as compared to vehicle-treated groups.

The results of this example indicate that 1D11 significantly reduced left ventricular scar volume at the 5 mg/kg dose as compared to vehicle. Interestingly, at the 25 mg/kg dose, LV scar volume was increased as compared to controls (FIG. 6). Histological analysis demonstrated a significant decrease in apoptosis in the area adjacent to the scar with 1D11 at the 5 mg/kg dose. There was increased apoptosis in the group that received 25 mg/kg of 1D11 (FIG. 7). There were no differences in subepicardial interstitial fibrosis in the area adjacent to the scar between all the groups (data not shown).

Figure 8:
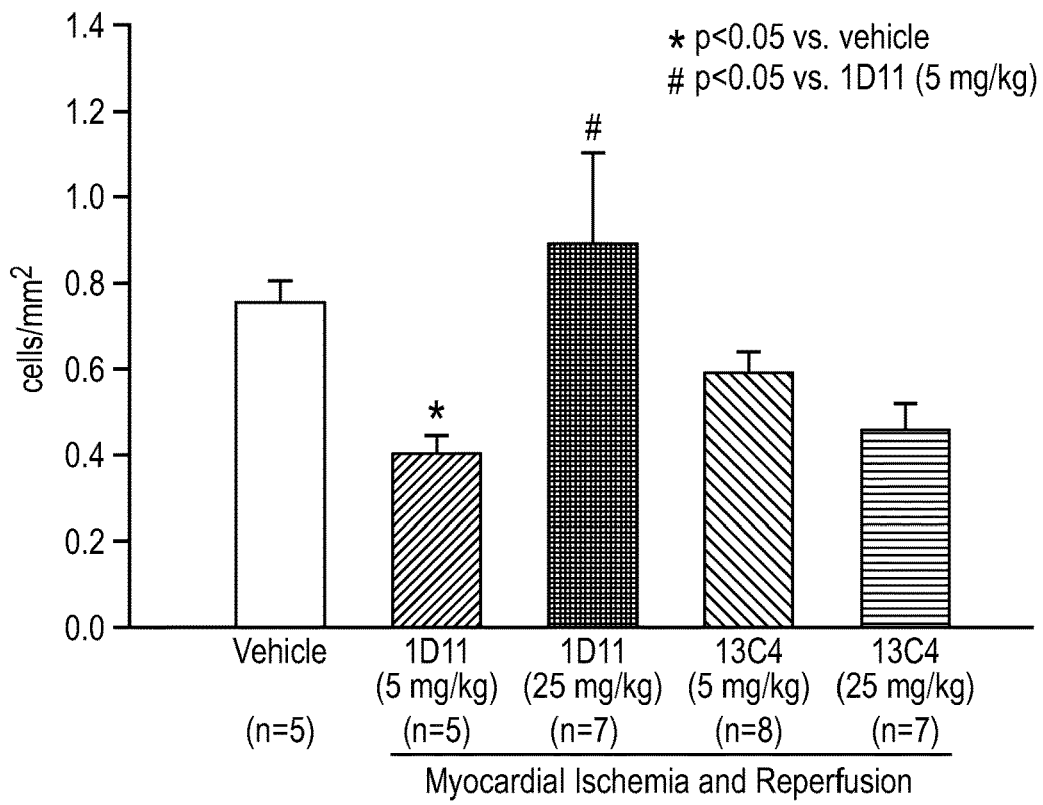
FIG. 8 shows the number of TUNEL positive cells in the area adjacent to the scar.
Figure 9:
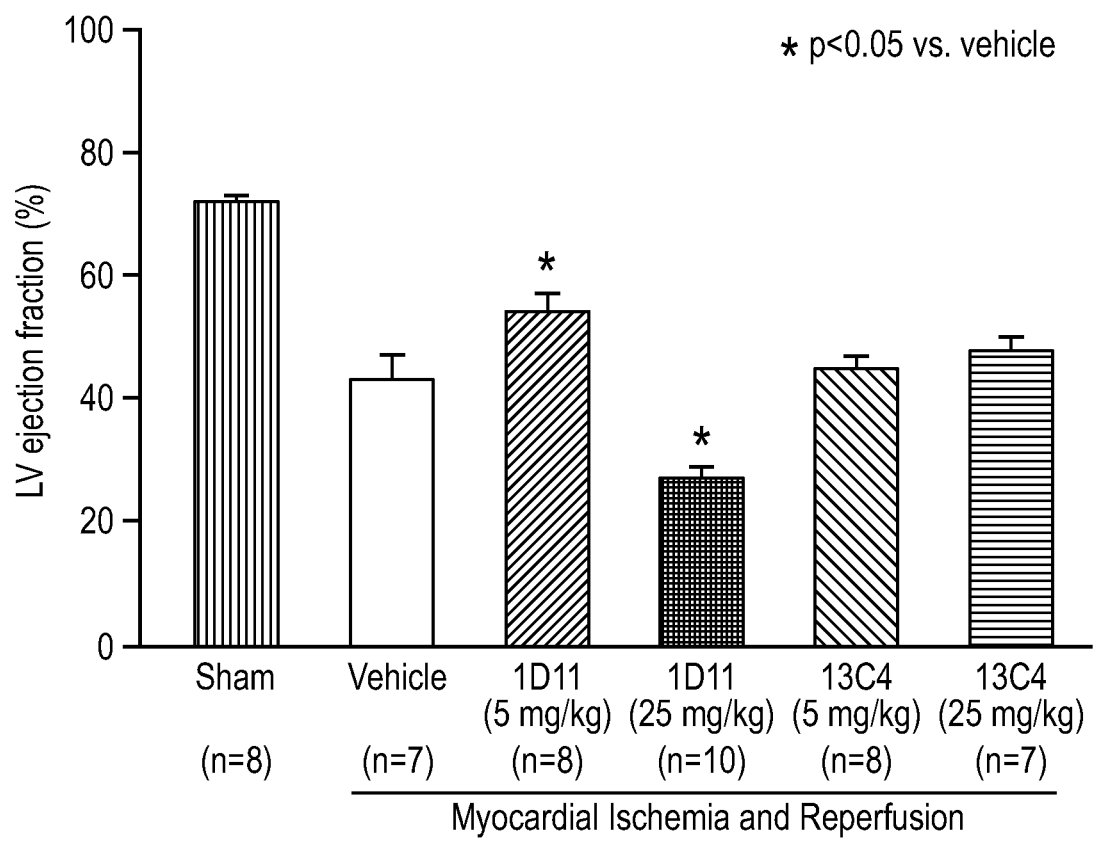
FIG. 9 shows the LV ejection fraction (LVEF), measured at 4 weeks after coronary artery occlusion/coronary artery reperfusion (CAO/CAR).

Left ventricular ejection fraction (LVEF), a measure of global systolic function, was reported at week 2 and week 4 (FIG. 8). LVEF at 4 weeks was significantly improved with 1D11 at the 5 mg/kg dose as compared to vehicle-treated animals. However, treatment with 1D11 at 25 mg/kg led to a significant decrease in EF. This is consistent with the scar volume data reported in FIG. 6. From week 2 to week 4, there was a significant improvement in the percent change in LVEF in the 1D11 5 mg/kg group (FIG. 9).

Figure 10:
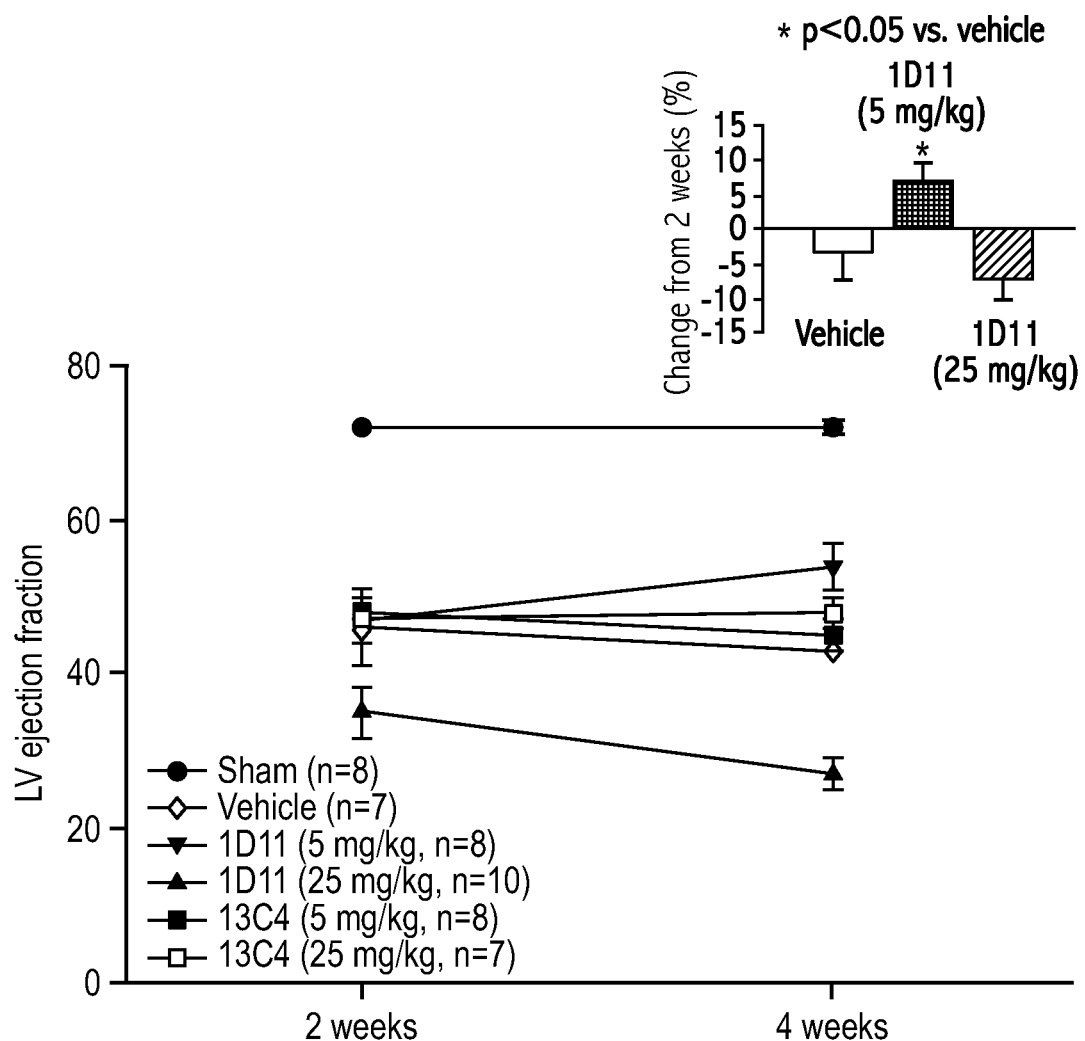
FIG. 10 shows the LVEF measured at 2-4 weeks after CAO/CAR.
Figure 11:
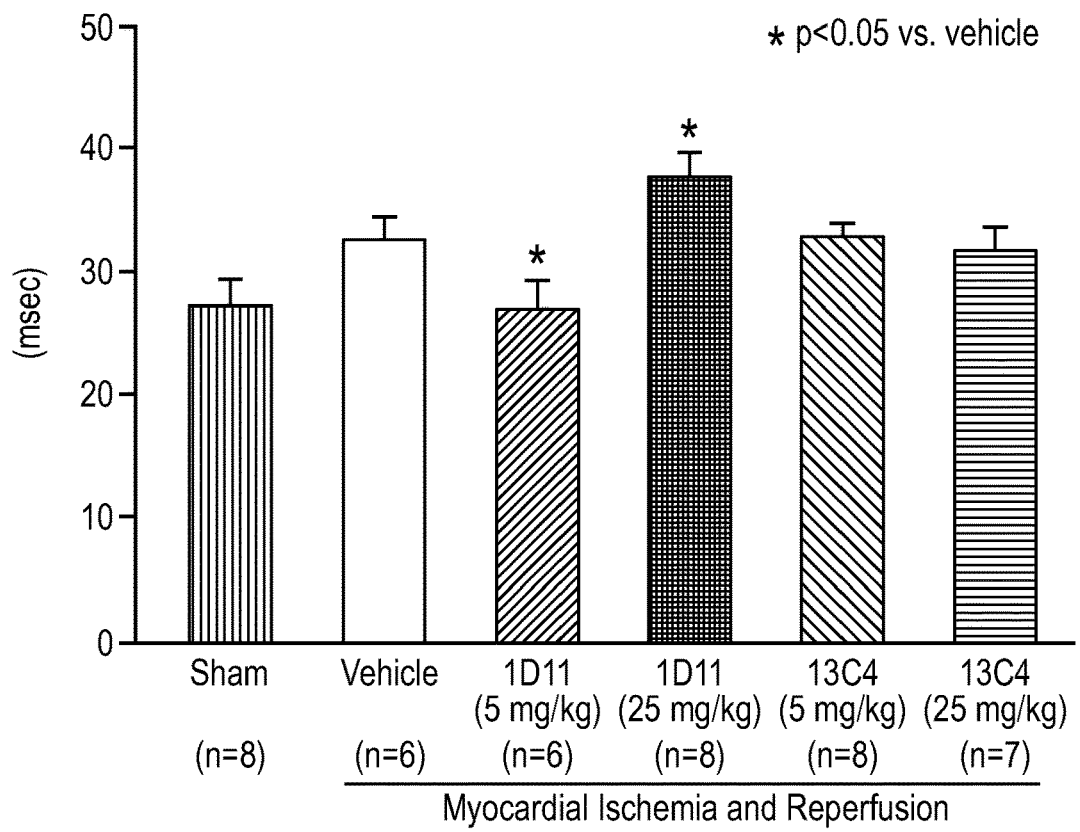
FIG. 11 shows LV isovolumetric relaxation time.

LV isovolumic relaxation time (IVRT), a measure of diastolic function, was also significantly improved in the 1D11 5 mg/kg group as compared to control groups and the high dose of 1D11. There was apparent normalization of diastolic function as compared to sham animals (FIG. 10). Regional wall motion shown as a percentage thickening in the anterior wall demonstrated a significant improvement in the 1D11 5 mg/kg group as compared to vehicle group (FIG. 11).

Figure 12:
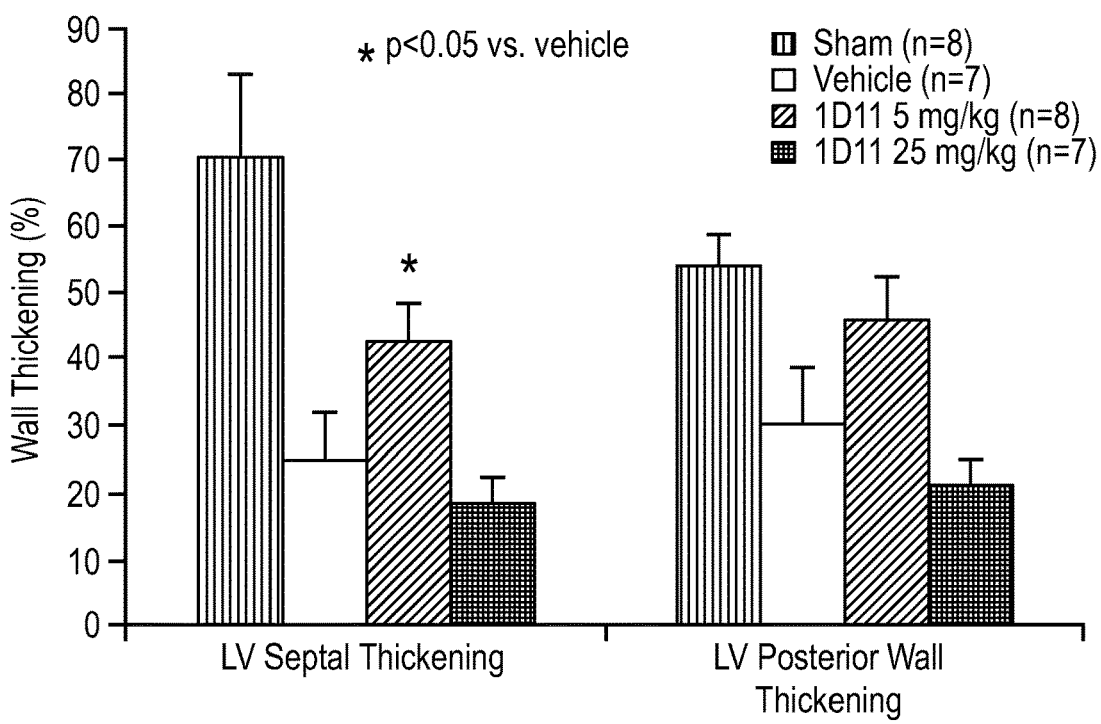
FIG. 12 shows regional wall thickening as compared to vehicle.
Figure 13:
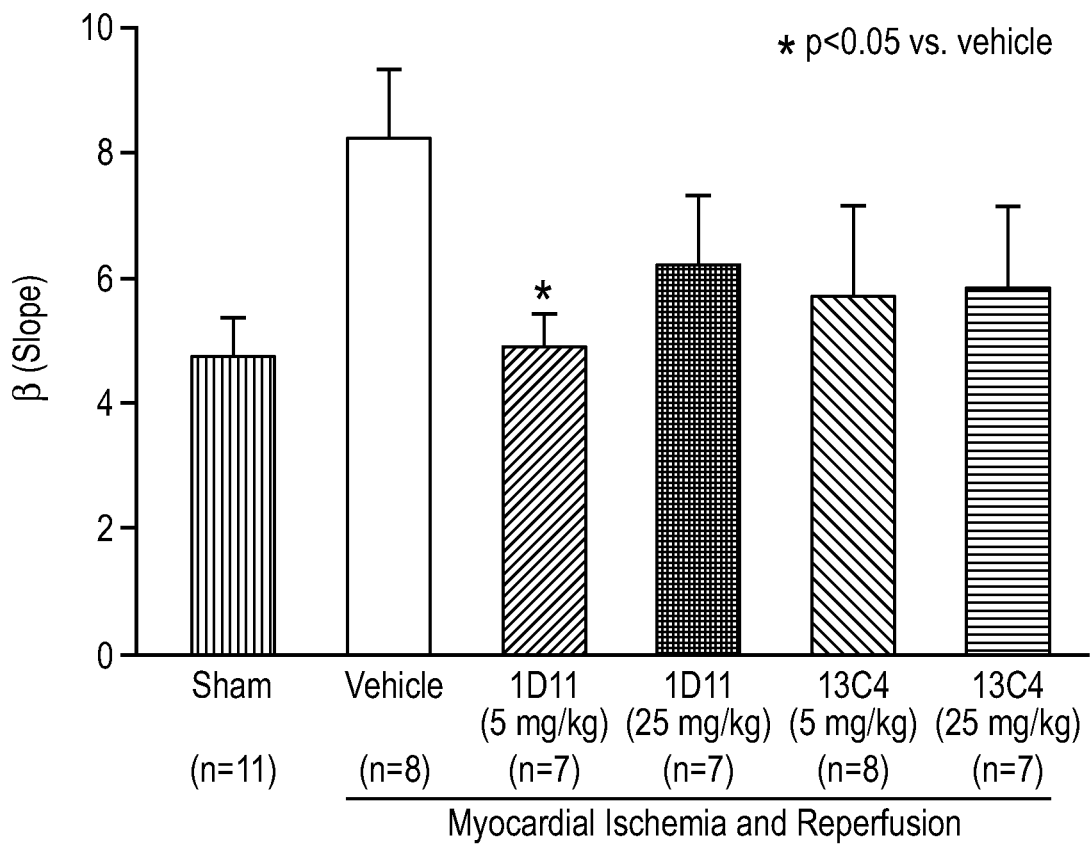
FIG. 13 shows the slopes of LV-end-diastolic pressure-volume relationship.

Left ventricular end diastolic pressure volume relationships, a measure of diastolic function assessed by PV hemodynamics demonstrated significant improvement in the 1D11 5 mg/kg group where the data are comparable to the sham animals (FIG. 12). The dobutamine stress test indicated that a trend towards improvement in the 1D11 5 mg/kg group (data not shown) exists.

The lower dose (5 mg/kg) of 1D11 demonstrated clear and significant salutary effects. First, LV scar volume at 4 weeks was lowest, indicating that there was less residual damage from the infarct. Second, there was significantly less apoptosis in the area adjacent to the scar as compared to the other groups. Third, LV function assessed by LV ejection fraction was significantly higher in this group than the other groups indicating the best salvage of LV function. Finally, this group was unique in demonstrating an improvement between 2 an 4 weeks in LV ejection fraction. The slope of the LV end-diastolic pressure-volume relationship at 4 weeks was the lowest in this group indicating reduced LV stiffness and improved LV diastolic function. This corroborated the IVRT results, an echocardiographic measure of diastolic function, which showed that this group was the only one to demonstrate preservation of diastolic function at 4 weeks. The dobutamine stress test showed a trend toward an improvement in cardiac function, although the inherent issues with anesthesia and catheterization contributed to variability and less reliance on this data as opposed to the echo data, The control antibody experiments did not show much difference from vehicle-treated rats.

On the other hand, the high dose of 1D11 demonstrated adverse effects. The scar at 4 weeks was larger than the other groups, including the vehicle-treated group. There was more apoptosis in the adjacent area. When LV function was assessed by LV ejection fraction, it was lower than all the other groups at 4 weeks. Therefore, TGF-β antagonism, utilizing 1D11 at the 5 mg/kg dose, was effective in preventing the adverse effects of remodeling following myocardial infarction in the rat. The significant reductions of LV scar volume and apoptosis were consistent with the improvements in cardiac systolic and diastolic function in this model. However, the high dose of the drug elicited opposite, adverse effects on histological and functional endpoints.

Example 5—Effects of TGF-B Inhibitor, 1D11, on Myocardial Preservation in a Rodent Model of Myocardial Ischemia Followed by Reperfusion Administration of 1D11, a TGF-β inhibitor, reduced fibrosis, preserved myocardium and improved cardiac function at 2 different doses. On Day 0, the left ascending coronary artery was ligated for 60 minutes and then released to allow for reperfusion (I/R). At day 5, two different doses (1 or 5 mg/kg) of one of either two different formulations of 1D11 (first and second formulations), vehicle, and 13C4 (negative-control antibody) were administrated via IV and continued every 3 days until day 28.

In order to analyze the area at risk, 15 micron diameter microspheres that were labeled with a yellow fluorochrome were injected into the LV of the heart. This was done immediately before releasing the temporary ligation of the left descending coronary artery. The microspheres distributed homogenously in the blood and lodged in capillaries of the heart, and other organs and tissues. The AAR in the heart was defined as the area of the myocardial tissue that did not receive any microspheres (or blood) during the ligation period.

At day 28, the animal was lightly anesthetized with isoflurane and the heart rate was maintained at 350±50 bpm. Echocardiography was then performed in the long axis view for regional cardiac function. Following the echocardiography examination, the animal was euthanized with an overdose of sodium pentobarbital. The heart was then excised, weighed and then processed for histological analysis. The AAR was assessed morphometrically on heart sections and using heart weight and expressed as a percentage of AAR weight/total LV weight. Animals with small AAR (<20%) or no AAR were removed from study analysis.

Cardiac fibrosis in the LV was assessed histologically and using heart weight and expressed as a percentage of fibrosis weight/total LV weight. Regional cardiac function was assessed by evaluation of the anterior wall thickening (AWT) as compared to posterior wall thickening (PWT) in the area at risk. Wall thickening is the difference in the wall thickness at systole and the wall thickness at diastole.

Figure 14:
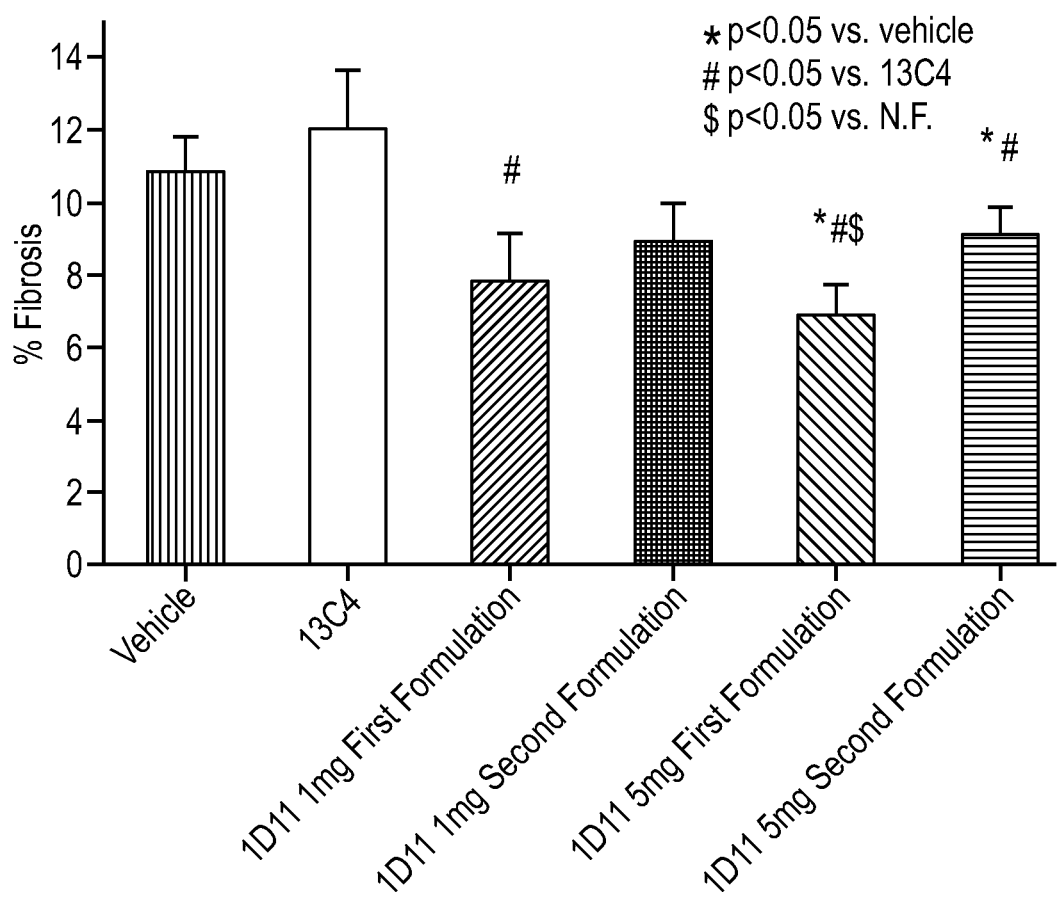
FIG. 14 shows a reduction in fibrosis in the LV with administration of 1D11 at doses of 1 and 5 mg/kg from two different formulations.
Figure 15:
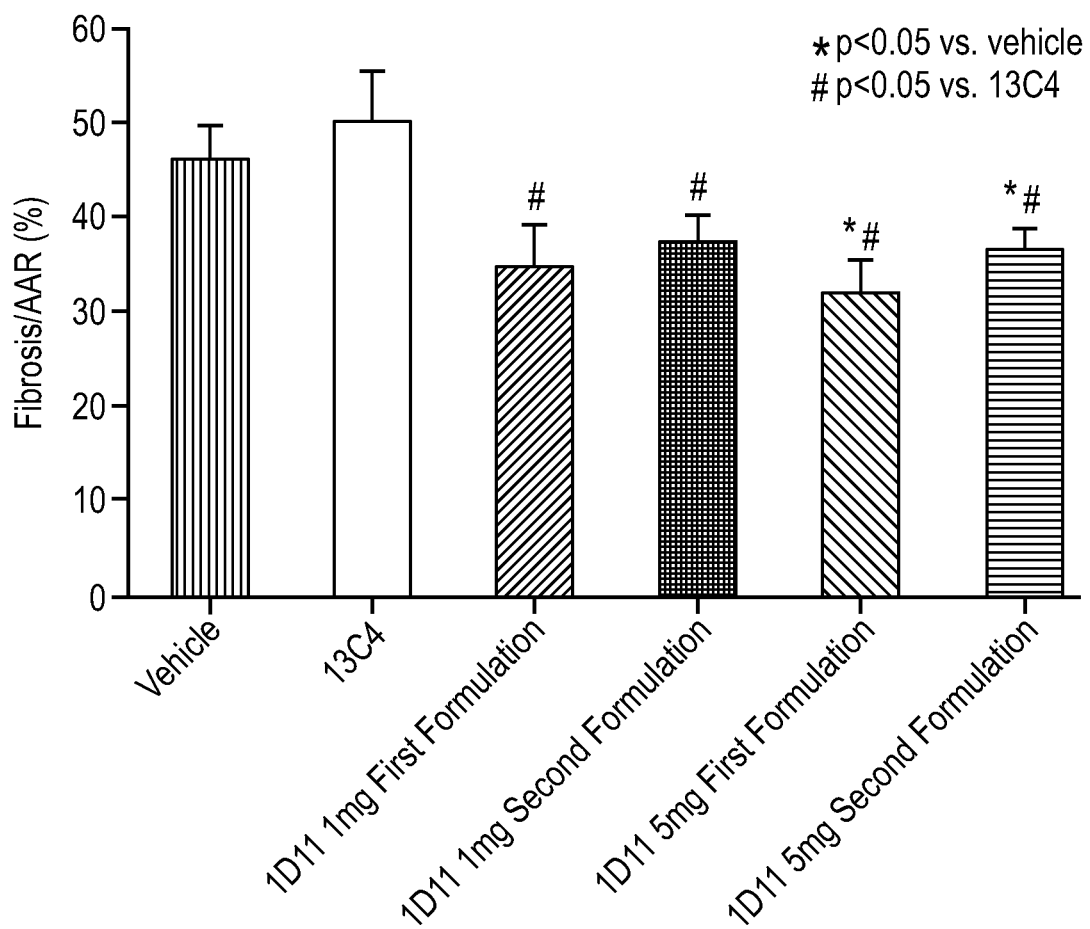
FIG. 15 shows a reduction in fibrosis with in the area at risk with administration of 1D11 at doses of 1 and 5 mg/kg from two different formulations.
Figure 16:
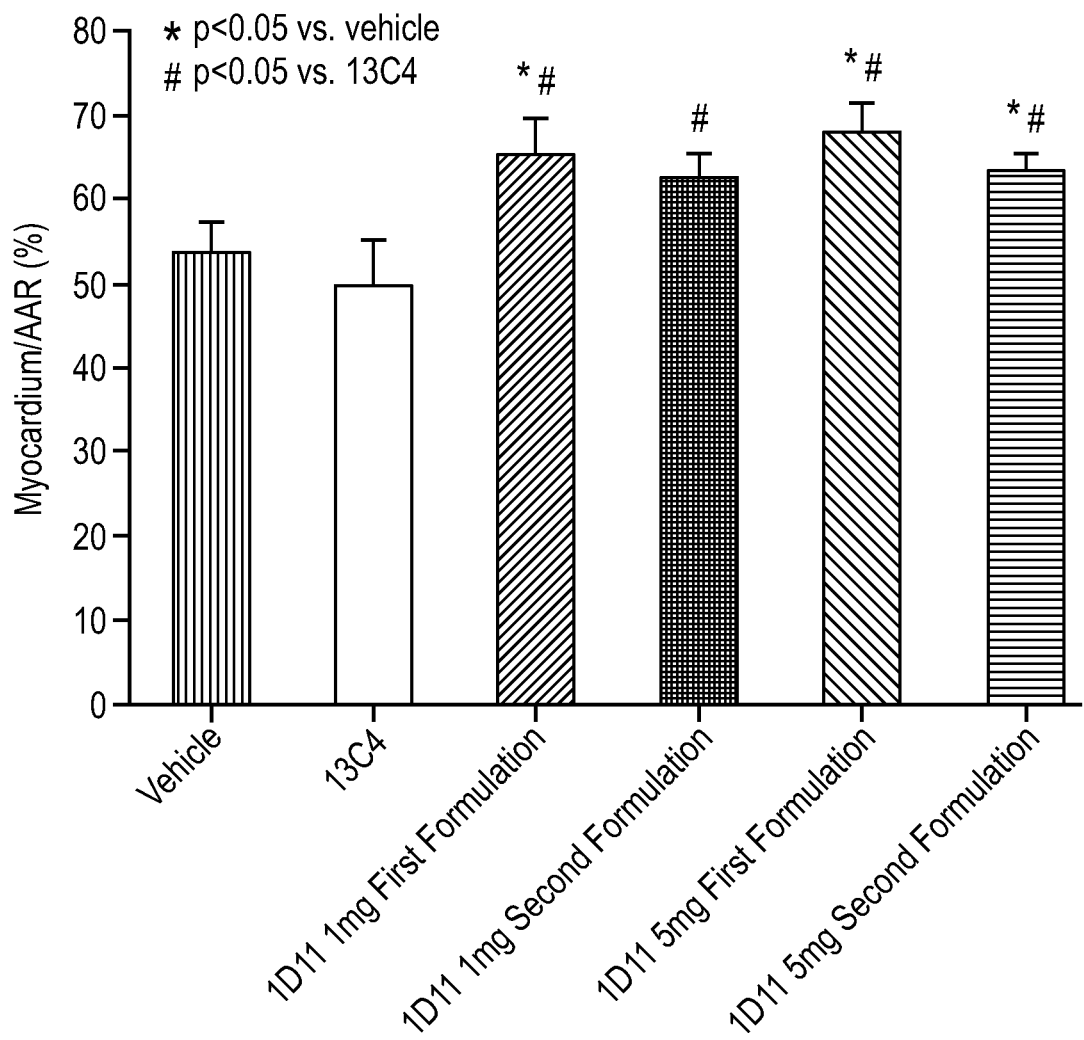
FIG. 16 shows an increase of myocardium in the area at risk with administration of 1D11 at doses of 1 and 5 mg/kg from two different formulations.

The results in this example demonstrate that at 4 weeks following I/R, 1D11 at the 1 and 5 mg/kg doses from the two different formulations significantly reduced the percentage fibrosis in the LV as compared to the 13C4 and vehicle controls (FIG. 14). In addition, both 1D11 doses from both formulations significantly reduced the percent fibrosis in the AAR as compared to the 13C4 and vehicle controls (FIG. 15). Importantly, both 1D11 doses from both formulations significantly increased the percentage of myocardium in the AAR as compared to controls (FIG. 16). This result indicates that 1D11 treatment following I/R not only reduced fibrosis but also preserved myocardium in the AAR.

Figure 17:
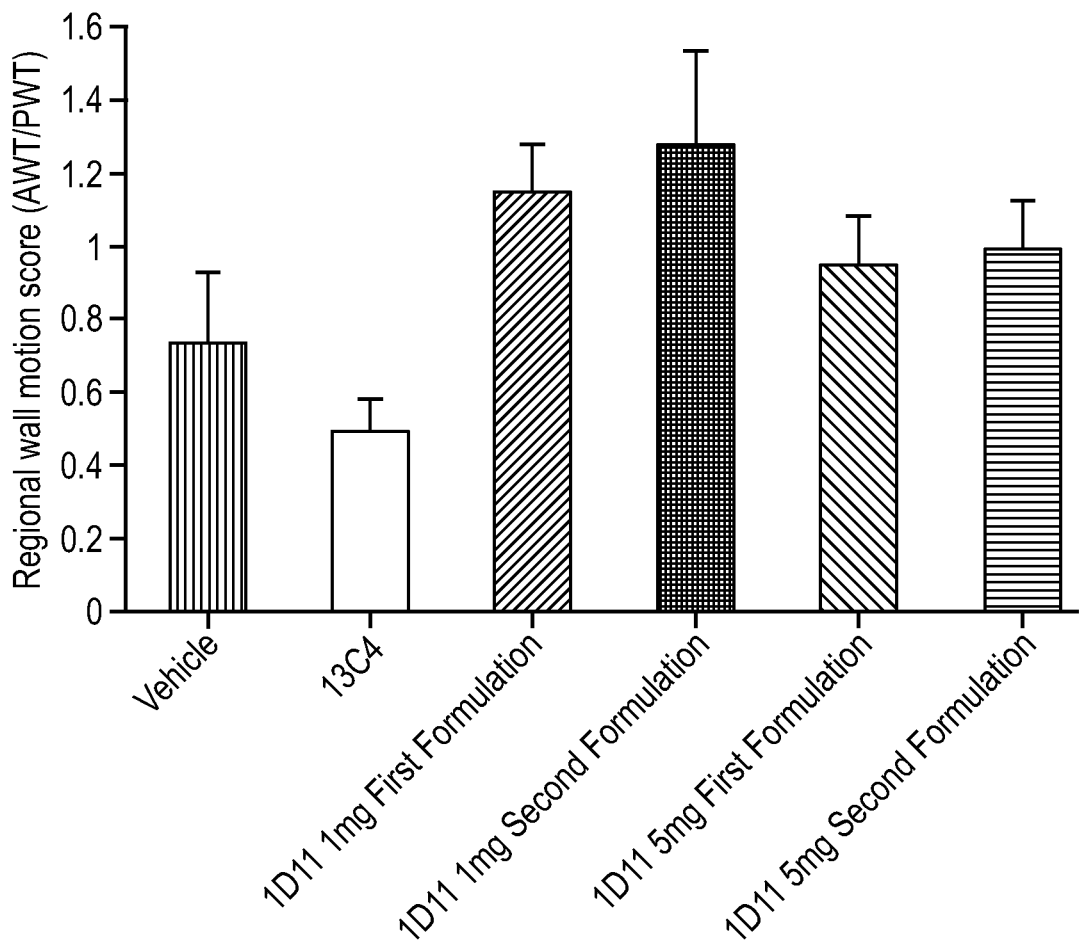
FIG. 17 shows the regional wall motion score in an echocardiogram analysis for vehicle, 13C4 and 1D11 at 1 and 5 mg/kg for both formulations.

At 4 weeks following I/R, cardiac function expressed as regional wall motion score (AWT/PWT) showed less impairment in all 1D11-treated groups (1 and 5 mg/kg doses from both formulations) as compared to the 13C4 and vehicle controls (FIG. 17).

This example evaluated the bioactivity of the TGF-β antagonist antibody, 1D11, at two doses (1 and 5 mg/kg) and from two different formulations, initiated 5 days following myocardial ischemia followed by reperfusion. Both the 1 and 5 mg/kg 1D11 doses from both formulations significantly reduced fibrosis and more importantly, preserved myocardium in the AAR as compared to the negative controls. Consistent with these improvements, regional cardiac function was also improved as compared to the negative controls.

Example 6—Effects of TGF-B Inhibitor, 1D11, on Cardiac Expression of TGF-B and Related Genes in a Rodent Model of Myocardial Ischemia Followed by Reperfusion Administration of 1D11, a TGF-β inhibitor, reduced cardiac expression of TGF-β and related genes, consistent with its effects on myocardial remodeling, myocardial preservation and myocardial function as observed in the previous examples. On Day 0, the left ascending coronary artery was ligated for 60 minutes and then released to allow for reperfusion (I/R). At day 3, two different doses (5 or 50 mg/kg) of 1D11 were administered via IV and continued every 3 days until either day 7 or day 12 for animals that received 5 mg/kg 1D11, or until day 12 for animals that received 50 mg/kg 1D11. Another group of animals that underwent I/R did not receive any treatment.

Depending on the study group, on either day 7 or day 12 the animal was euthanized by an overdose of sodium pentobarbital. Blood was collected into a serum separator tube and the serum collected for analysis of levels of 1D11 and osteopontin (a potential serum biomarker of 1D11 effects on fibrosis reduction), using 1D11 or osteopontin ELISAs, respectively. The heart was then excised, the atria and right ventricled trimmed away, and the left ventricle sectioned longitudinally through the center of the area at risk (the area of the heart that did not receive blood during the ligation of the left ascending coronary artery). One half of the ventricle was flash frozen for analysis of TGF-β and related gene expression by reverse transcriptase-polymerase chain reaction (RT-PCR). For RT-PCR analysis this portion of the ventricle was further subdivided into an apical portion, which included the area at risk, and a basal portion that was not subject to ischemia. The other half of the ventricle was fixed in formalin for later analysis. A group of normal rats were euthanized by an overdose of sodium pentobarbital and subjected to serum and heart collection as described above.

Figure 18:
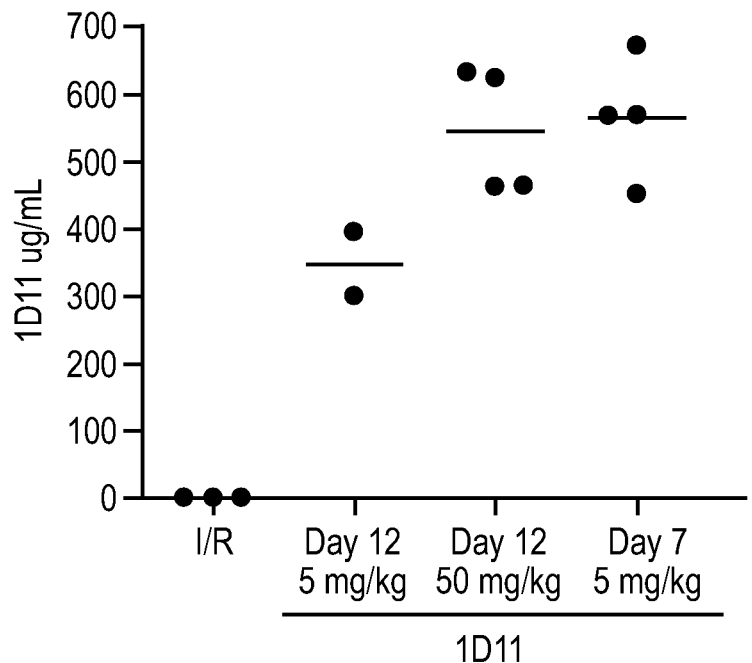
FIG. 18 shows dose-dependent serum levels of 1D11 following IV administration of the antibody.

Animals that received 1D11 demonstrated 1D11 in their sera while the I/R group that did not receive 1D11 did not have detectable 1D11 in their sera (FIG. 18). In the animals that received 5 mg/kg 1D11, the animals euthanized on day 7 had higher 1D11 serum levels than that observed in the animals euthanized on day 12. This was anticipated since animals euthanized on day 7 had their sera collected one day after their last dose of 1D11 whereas animals euthanized on day 12 had their sera collected 3 days after their last dose of 1D11. The serum 1D11 level in animals that received the 50 mg/kg 1D11 dose and was euthanized on day 12 was approximately 1.5 times that of the animals that received 5 mg/kg 1D11 and were euthanized on the same day. The lack of proportionality in the 1D11 serum levels as compared to dose may be attributable to faster clearance of 1D11 in animals that received the high dose (50 mg/kg) of 1D11. These data indicate that IV delivery of 1D11 results in dose-dependent levels of 1D11 in circulation and presumably, 1D11 exposure to the heart.

Figure 19:
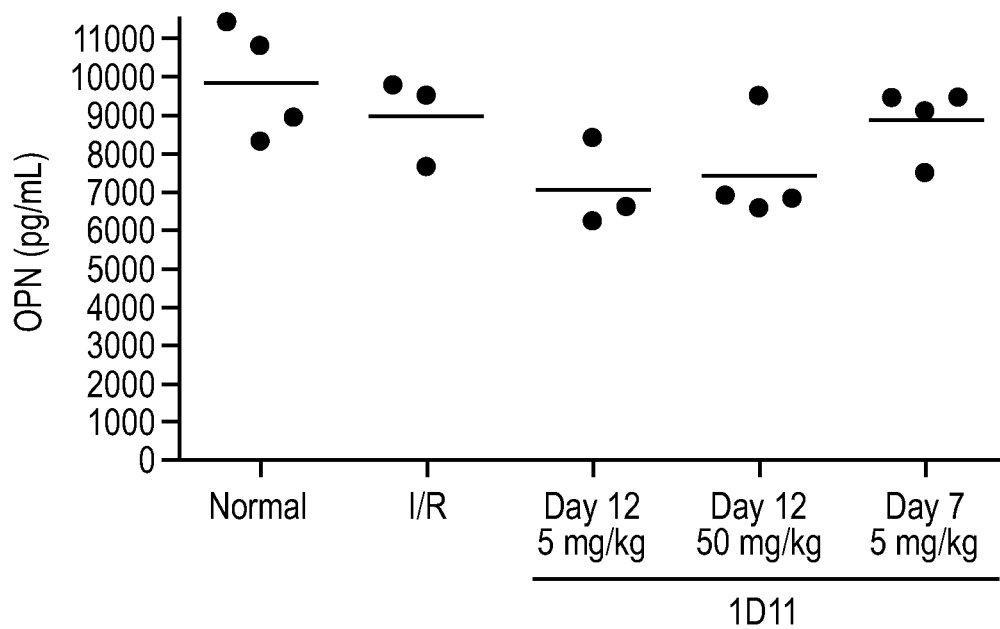
FIG. 19 shows reductions in serum osteopontin with administration of 1D11 post I/R.

Osteopontin is a potential serum marker of 1D11-mediated modulation of fibrosis in cardiac I/R. Serum osteopontin levels were similar in normal animals, I/R animals that did not receive any treatment and were euthanized on day 12, and I/R animals that received two 5 mg/kg doses of 1D11 and were euthanized on day 7 (FIG. 19). There were trends towards decreases in osteopontin levels in I/R animals that received either three 5 mg/kg 1D11 doses and were euthanized on day 12, or three 50 mg/kg doses of 1D11 and were euthanized on day 12.

The expression of TGF-β and related genes was analyzed by RT-PCR in the apical portion of the left ventricle, which included the area at risk and the basal portion of the LV that was not subject to ischemia. In the basal portion of the LV the expression levels of all the genes evaluated were similar to that observed in normal animals. The remainder of the descriptions of cardiac gene expression focuses on changes observed in the apical portion of the ventricle.

Figure 20:
FIG. 20 shows induction of TGF-β1 following IR and dose-dependent 1D11-mediated reduction of TGF-β1 following I/R.
Figure 21:
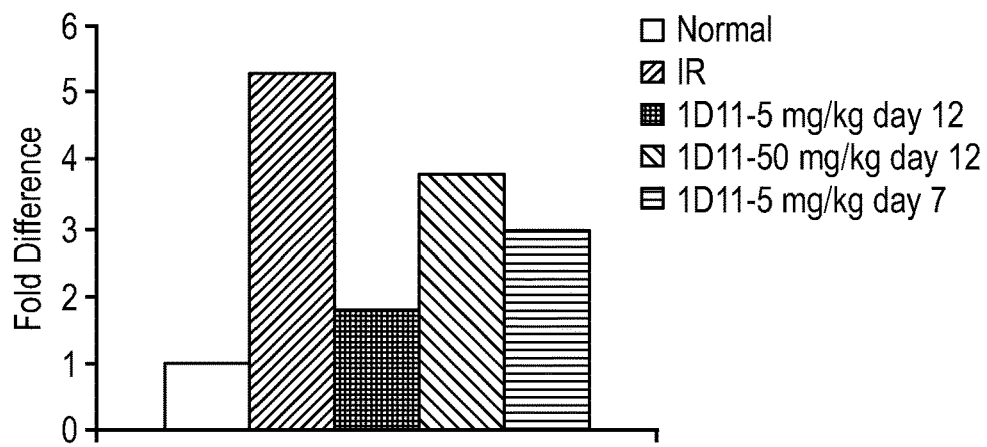
FIG. 21 shows induction of TGF-β2 following IR and dose-dependent 1D11-mediated reduction of TGF-β21 following I/R.
Figure 22:
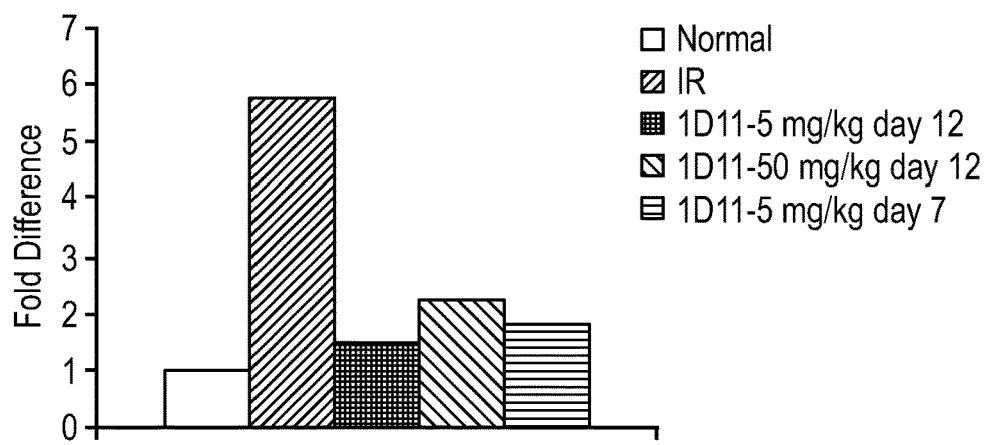
FIG. 22 shows induction of TGF-β3 following IR and dose-dependent 1D11-mediated reduction of TGF-b3 following I/R.

The cardiac expression of all TGF-β isoforms, TGF-β1, TGF-β2 and TGF-β3, were elevated in I/R animals that did not receive any treatment and were euthanized on day 12. Compared to normal animals expression of TGF-β1, TGF-β2 and TGF-β3 were increased approximately 2.3-fold, 5-fold, and 6-fold, respectively (FIGS. 20-22). Administration of 1D11 at 5 mg/kg reduced expression of TGF-β1, TGF-β2 and TGF-β3 (FIGS. 20-22). Animals that received three 5 mg/kg doses of 1D11 and were euthanized on day 12 had greater reductions in the expression of TGF-β1 and TGF-β2 as compared to animals that received 2 doses and were euthanized on day 7 (FIGS. 20, 21). There were similar reductions in the expression of TGF-β3 in animals that received two or three 5 mg/kg doses of 1D11 (FIG. 22). Animals that received three 50 mg/kg 1D11 doses and were euthanized on day 12 also showed reduction in the expression of all three TGF-β isoforms. However, the reductions in TGF-β1 and TGF-β2 expression were somewhat less robust than that observed in animals that received 2 doses of 5 mg/kg 1D11 and were euthanized on day 7 (FIGS. 19-21). These results demonstrate dose-dependent suppression of the expression of all TGF-β isoforms by 1D11. Interestingly, the higher 1D11 dose (50 mg/kg) appeared to result in less suppression of TGF-β expression compared to the 5 mg/kg dose.

Figure 23:
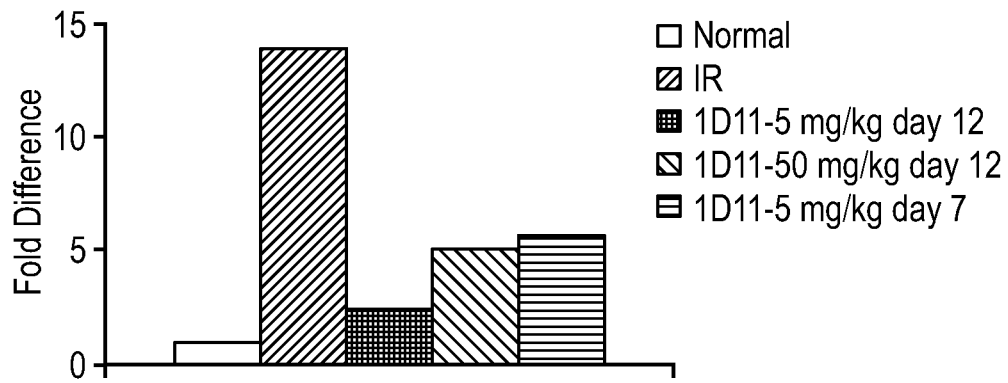
FIG. 23 shows induction of collagen 3 following IR and dose-dependent 1D11-mediated reduction of collagen 3 following I/R.

Collagen is a prominent component of fibrosis and its expression is known to be regulated by TGF-β. Cardiac expression of collagen 3 was elevated approximately 14-fold in I/R animals that did not receive any treatment compared to normal animals. Administration of 5 mg/kg 1D11 reduced the expression of collagen 3 where animals that received 3 doses of 1D11 had greater reduction in collagen 3 expression compared to animals that received 2 doses of 1D11 (FIG. 23). Animals that received 50 mg/kg 1D11 also demonstrated a reduction in collagen 3 expression that was comparable to that observed in animals that received two 5 mg/kg 1D11 doses. Consistent with the 1D11-mediated reduction in cardiac fibrosis following I/R, there was a 1D11-mediated dose-dependent reduction in cardiac collagen 3 expression. Similar to 1D11-mediated suppression of TGF-β expression, the higher 1D11 dose (50 mg/kg) appeared to result in less suppression of collagen 3 compared to the 5 mg/kg dose.

Figure 24:
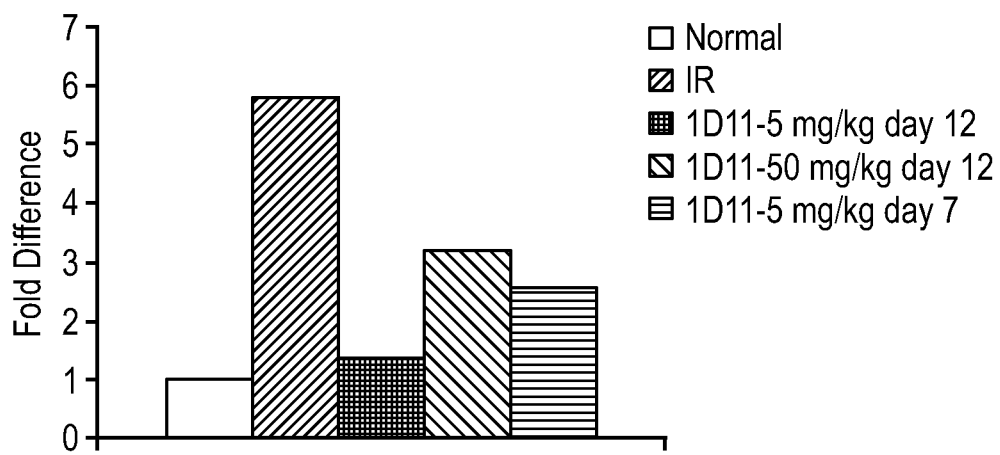
FIG. 24 shows induction of endothelin-1 following IR and dose-dependent 1D11-mediated reduction of endothelin-1 following I/R.

Endothelin-1 (ET-1) is potent vasoconstrictor whose expression is regulated by TGF-β. Cardiac expression of ET-1 was increased approximately 5.5-fold in I/R animals that did not receive any treatment compared to normal animals. Administration of 5 mg/kg 1D11 reduced the expression of ET-1 where animals that received 3 doses of 1D11 had greater reduction in ET-1 expression compared to animals that received 2 doses of 1D11 (FIG. 24). Three 5 mg/kg 1D11 doses nearly normalized ET-1 expression. Animals that received 50 mg/kg 1D11 also demonstrated a reduction in ET-1 expression that was comparable to that observed in animals that received two 5 mg/kg 1D11 doses. 1D11-mediated inhibition of ET-1 expression following I/R may contribute to improved perfusion in the injured myocardium and contribute to the myocardial preservation and reduced remodeling following I/R. Interestingly, the 50 mg/kg 1D11 appeared to have resulted in less suppression of ET-1 expression compared to the 5 mg/kg dose.

Figure 25:
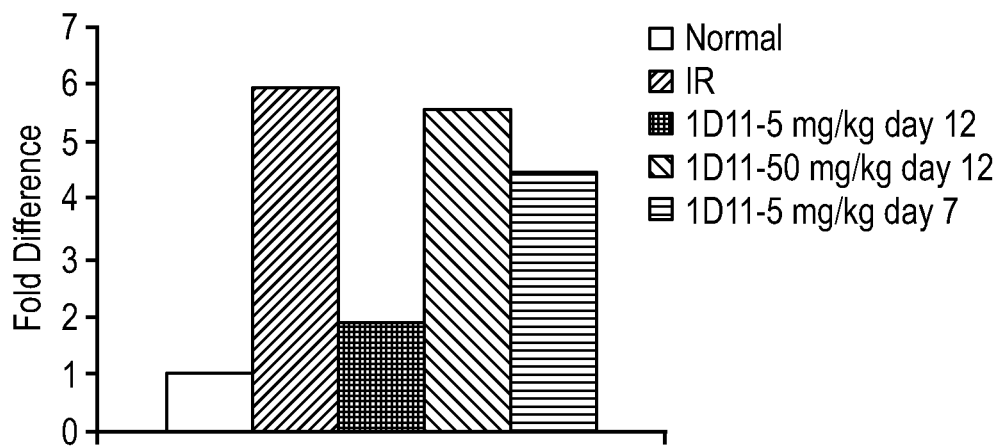
FIG. 25 shows induction of plasminogen activator inhibitor-1 following IR and dose-dependent 1D11-mediated reduction of plasminogen activator inhibitor-1 following I/R.

Plasminogen activator inhibitor-1 (PAI-1) is the major inhibitor of tissue-type plasminogen activator and is regulated by TGF-β. Elevated levels of PAI-1 has been associated with increased atherothrombotic events and vascular disease. Cardiac expression of PAI-1 was increased approximately 6-fold in I/R animals that did not receive any treatment as compared to normal animals. Administration of 5 mg/kg 1D11 reduced the expression of PAI-1 where animals that received 3 doses of 1D11 had much greater reduction in PAI-1 expression as compared to animals that received 2 doses of 1D11 (FIG. 25). Animals that received 50 mg/kg 1D11 showed marginal reduction in PAI-1 expression. It is likely the 1D11-mediated reduction in PAI-1 expression following I/R contributed to the improvements in remodeling and myocardial preservation. The 50 mg/kg 1D11 dose appeared to have a much less robust effect on reducing PAI-1 expression compared to the 5 mg/kg dose.

Figure 26:
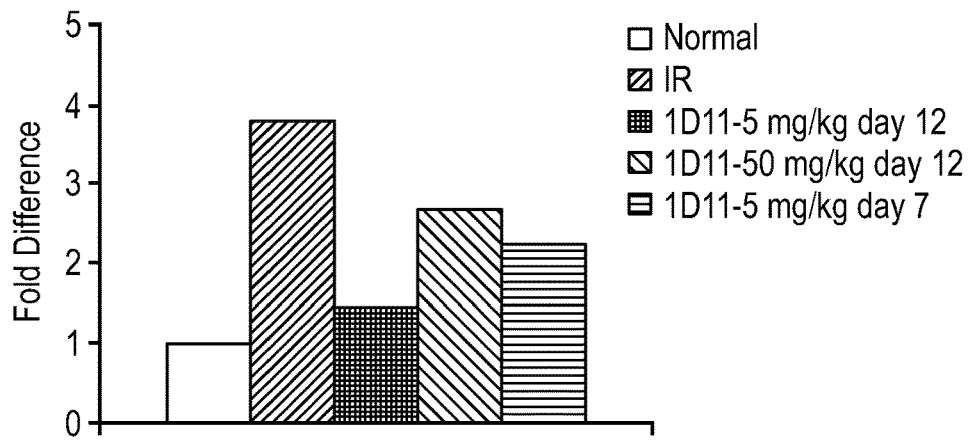
FIG. 26 shows induction of Snail1 following IR and dose-dependent 1D11-mediated reduction of Snail1 following I/R.
Figure 27:
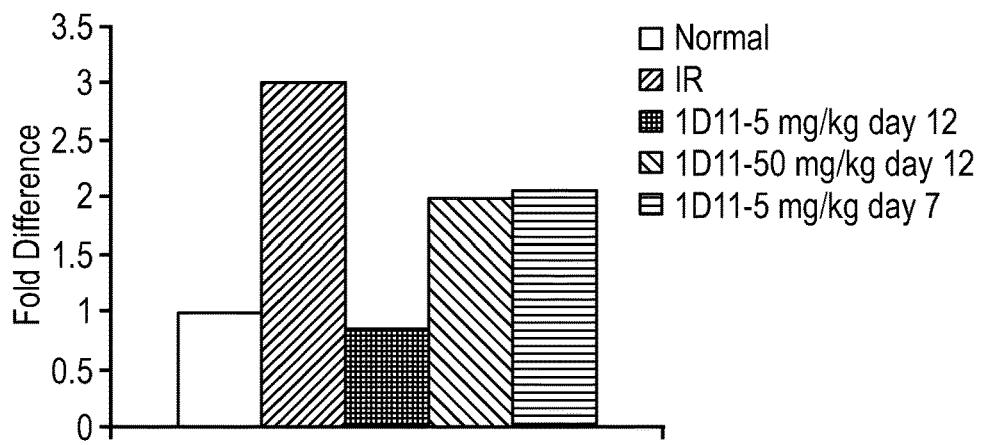
FIG. 27 shows induction of Snail2 following IR and dose-dependent 1D11-mediated reduction of Snail2 following I/R.

Recently it has been recognized that endothelial-mesenchymal transition can contribute to cardiac fibrosis. Transcription factors Snail1 and Snail2 (Slug) are involved in endothelial-mesenchymal transition and these transcription factors are induced by TGF-β. Cardiac expression of Snail1 and Snail2 were increased approximately 4-fold and 3-fold, respectively, in I/R animals that did not receive any treatment as compared to normal animals. Administration of 5 mg/kg 1D11 reduced the expression of both Snail1 and Snail2 where animals that received 3 doses of 1D11 had much greater reduction in Snail1 and Snail2 expression as compared to animals that received 2 doses of 1D11 (FIGS. 26 and 27). Three 5 mg/kg doses of 1D11 apparently normalized Snail2 expression. Animals that received 50 mg/kg 1D11 also demonstrated reductions in Snail1 and Snail2 expression that were comparable to that observed in animals that received two 5 mg/kg 1D11 doses. Increased expression of Snail1 and Snail2 following I/R strongly suggest that endothelial-mesenchymal transition is contributing to cardiac fibrosis in the repair response to I/R. The 1D11-mediated reductions in Snail1 and Snail2 expression following I/R are likely a contributing mechanism to the observed reduction in cardiac fibrosis and improvement in remodeling. Interestingly, the 50 mg/kg 1D11 dose appeared to have a less robust effect on reducing Snail1 and Snail2 expression as compared to the 5 mg/kg dose.

Figure 28:
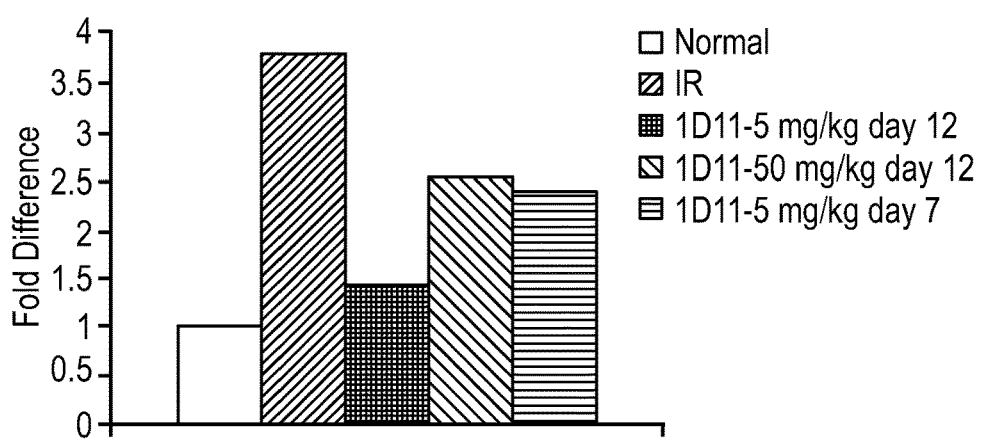
FIG. 28 shows induction of α-smooth muscle actin following IR and dose-dependent 1D11-mediated reduction of α-smooth muscle actin following I/R.

A marker of mesenchymal cells that is observed in endothelial-mesenchymal transition a-smooth muscle actin (α-SMA). Cardiac expression α-SMA was elevated approximately 4-fold in I/R animals that did not receive any treatment as compared to normal animals. Administration of 5 mg/kg 1D11 reduced the expression of α-SMA where animals that received 3 doses of 1D11 had much greater reduction α-SMA expression as compared to animals that received 2 doses of 1D11 (FIG. 28). Animals that received 50 mg/kg 1D11 also demonstrated reduction in α-SMA expression that was comparable to that observed in animals that received two 5 mg/kg 1D11 doses. Consistent with the 1D11-mediated reduction in Snail1 and Snail 2 following I/R, 1D11 reduced expression of α-SMA. The 50 mg/kg 1D11 dose appeared to have a less robust effect on reducing α-SMA expression as compared to the 5 mg/kg dose.

Figure 29:
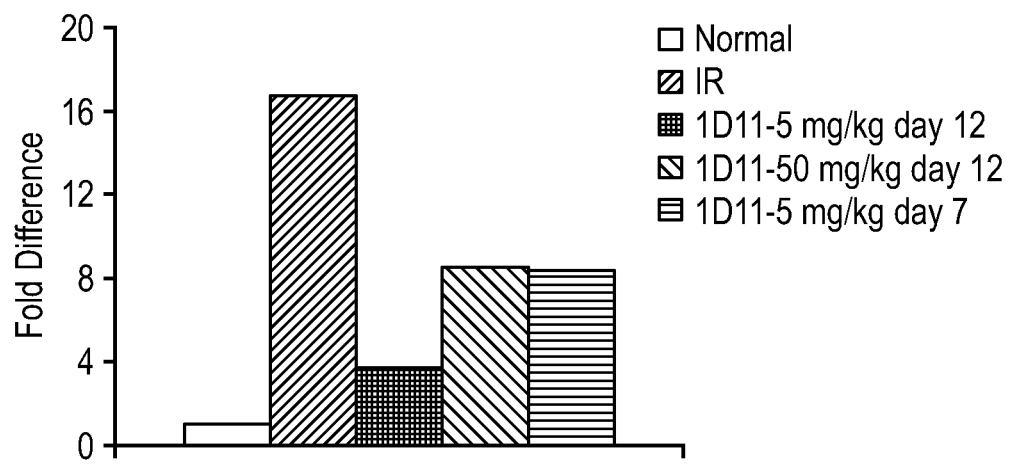
FIG. 29 shows induction of fibronectin following IR and dose-dependent 1D11-mediated reduction of fibronectin following I/R.

Fibronectin is considered to be a marker of epithelial-mesenchymal transition and likely is a marker endothelial-mesenchymal transition. Cardiac expression fibronectin was increased approximately 16-fold in I/R animals that did not receive any treatment as compared to normal animals. Administration of 5 mg/kg 1D11 reduced the expression of fibronectin where animals that received 3 doses of 1D11 had much greater reduction fibronectin expression as compared to animals that received 2 doses of 1D11 (FIG. 29). Animals that received 50 mg/kg 1D11 also demonstrated reduction in fibronectin expression that was comparable to that observed in animals that received two 5 mg/kg 1D11 doses. The 1D11-mediated reduction in fibronectin was compatible with the 1D11 medicated reductions in endothelial-mesenchymal transition markers Snail1, Snail2 and α-SMA. The 50 mg/kg 1D11 dose appeared to have a less robust effect on reducing fibronectin expression as compared to the 5 mg/kg dose.

Figure 30:
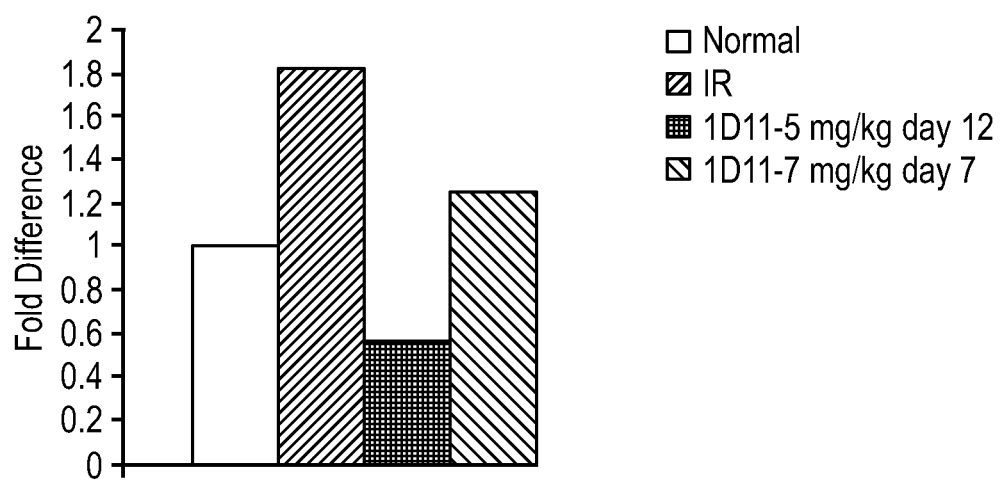
FIG. 30 shows effect of administration of 5 mg/kg 1D11 on the expression of Bax.

Apoptosis contributes to loss of cardiac myocytes during cardiac remodeling. Bax is a well recognized pro-apoptotic gene and cardiac expression Bax was increased approximately 1.8-fold in I/R animals that did not receive any treatment as compared to normal animals. Administration of 5 mg/kg 1D11 reduced the expression of Bax where animals that received 3 doses of 1D11 had a greater reduction Bax expression as compared to animals that received 2 doses of 1D11 (FIG. 30). Due to sample limitations hearts from animals that received 50 mg/kg 1D11 were not analyzed for Bax expression. The 1D11-mediated reduction in Bax expression is consistent with observations in previous examples where there was reduction in apoptosis in hearts from I/R animals that received 5 mg/kg 1D11, and there was increased myocardial preservation in I/R animals that received 1 and 5 mg/kg 1D11.

The results described in this example demonstrate that IV administration of a TGF-β antagonist (e.g., an anti-TGF-β antibody) results in dose-dependent circulating levels of 1D11 and presumably, exposure to the heart. Serum level of osteopontin may be a marker of 1D11-mediated reduction of cardiac fibrosis. TGF-β and related genes are induced in I/R and are drivers of the cardiac fibrosis and remodeling that occurs following I/R. Administration of the TGF-β antagonist antibody, 1D11, following I/R mediates reduction in the expression of these genes which provides a mechanism for the reduction in cardiac fibrosis, myocardial preservation, improvements in remodeling and improvements in cardiac function that were observed with 1D11 treatment. The results also demonstrated that genes involved in endothelial-mesenchymal transition were induced following I/R and that endothelial-mesenchymal transition may contribute to cardiac fibrosis following I/R. To the best of our knowledge, this is a novel finding. 1D11 treatment following I/R down regulated these genes and down modulated any contribution of endothelial-mesenchymal transition to cardiac fibrosis following I/R. Interestingly, the 5 mg/kg 1D11 dose apparently resulted in more robust reductions in the expression of TGF-β and related genes following I/R when as compared to the 50 mg/kg 1D11 dose.

What is claimed is:

1. A method of treating myocardial infarction in a patient in need thereof, comprising
   administering to the patient an antibody or antigen-binding fragment that binds to one or more isoforms of transforming growth factor-β (TGF-β), wherein the antibody or antigen-binding fragment comprises the PET1073G12 VH domain (SEQ ID NO: 2) and the PET1073G12 VL domain (SEQ ID NO:7); and
   measuring the patient's level of Snail1, or
   measuring the patient's level of Snail2.

2. The method of claim 1, wherein the myocardial infarction is an acute myocardial infarction.

3. The method of claim 1, wherein administration of the antibody or antigen-binding fragment is commenced within 120 hours of onset of myocardial ischemia.

4. The method of claim 1, wherein administration of the antibody or antigen-binding fragment is commenced within 12 hours of onset of myocardial ischemia.

5. The method of claim 1, wherein administration of the antibody or antigen-binding fragment is commenced prior to substantial macrophage and mononuclear infiltration of tissue affected by the myocardial infarction.

6. The method of claim 1, wherein administration of the antibody or antigen-binding fragment is commenced during a period characterized by neutrophilic infiltration of tissue affected by the myocardial infarction.

7. The method of claim 1, wherein administration of the antibody or antigen-binding fragment is commenced during a period characterized by necrosis of tissue affected by the myocardial infarction.

8. The method of claim 1, wherein the patient is a human or a non-human mammal.

9. The method of claim 1, wherein the method preserves myocardium.

10. The method of claim 1, wherein the method further comprises administering a compound that is capable of selectively restoring a desirable function of TGF-β to the patient.

11. The method of claim 10, wherein the compound capable of selectively restoring a desirable function of TGF-β is an anti-inflammatory drug.

12. The method of claim 10, wherein the compound capable of selectively restoring a desirable function of TGF-β is an antagonist of TNF-α.

13. The method of claim 1, wherein the method further comprises administering an ACE inhibitor to the patient.

14. The method of claim 13, wherein the ACE inhibitor is selected from the group consisting of benazepril, captopril, fosinopril, moexipril, perindopril, quinapril, transdolapril, lisinopril, enalapril, and ramipril.

15. The method of claim 1, wherein the method further comprises administering an angiotensin II receptor antagonist to the patient.

16. The method of claim 15, wherein the angiotensin II receptor antagonist is selected from the group consisting of eprosartan, telmisartan, losartan, irbesartan, olmesartan, candesartan, and valsartan.

17. The method of claim 1, wherein the method further comprises administering a beta-adrenergic antagonist to the patient.

18. The method of claim 17, wherein the beta-adrenergic antagonist is selected from the group consisting of alprenolol, bucindolol, carteolol, carvedilol, labetalol, nadolol, oxprenolol, penbutolol, pindolol, propranolol, sotalol, timolol, atenolol, betaxolol, bisoprolol, celiprolol, esmolol, metoprolol, and nebivolol.

19. The method of claim 1, wherein the antibody or antigen-binding fragment is administered to the patient during an acute stage of myocardial infarction at a dose of about 1 mg per kilogram of patient body mass.

20. The method of claim 1, wherein the antibody or antigen-binding fragment is administered to the patient during an acute stage of myocardial infarction at a dose of about 5 mg per kilogram of patient body mass.

* * * * *